(12) United States Patent
Bowman et al.

(10) Patent No.: US 10,342,761 B2
(45) Date of Patent: Jul. 9, 2019

(54) METHOD OF ENCAPSULATING A NUCLEIC ACID IN A LIPID NANOPARTICLE HOST

(71) Applicant: Novartis AG, Basel (CH)

(72) Inventors: Keith A. Bowman, Harleysville, PA (US); Noah Gardner, Cambridge, MA (US); Travis Jeannotte, Nashua, NH (US); Chandra Vargeese, Schwenksville, PA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/326,291

(22) PCT Filed: Jul. 10, 2015

(86) PCT No.: PCT/US2015/039879
§ 371 (c)(1),
(2) Date: Jan. 13, 2017

(87) PCT Pub. No.: WO2016/010840
PCT Pub. Date: Jan. 21, 2016

(65) Prior Publication Data
US 2017/0196809 A1    Jul. 13, 2017

Related U.S. Application Data

(60) Provisional application No. 62/025,224, filed on Jul. 16, 2014.

(51) Int. Cl.
| | | |
|---|---|---|
| *A61K 9/127* | (2006.01) | |
| *C12N 15/88* | (2006.01) | |
| *C12N 15/113* | (2010.01) | |
| *A61K 31/7105* | (2006.01) | |
| *A61K 31/713* | (2006.01) | |
| *A61K 48/00* | (2006.01) | |

(52) U.S. Cl.
CPC .......... *A61K 9/1277* (2013.01); *A61K 9/1272* (2013.01); *A61K 31/713* (2013.01); *A61K 31/7105* (2013.01); *A61K 48/0008* (2013.01); *A61K 48/0091* (2013.01); *C12N 15/113* (2013.01); *C12N 15/88* (2013.01); *C12N 2310/14* (2013.01); *C12N 2320/32* (2013.01)

(58) Field of Classification Search
CPC   A61K 48/0091; A61K 9/1227; C12N 15/113; C12N 2310/14; C12N 15/88
USPC ............................................. 514/44; 435/6.1
See application file for complete search history.

(56) References Cited

U.S. PATENT DOCUMENTS

| | | |
|---|---|---|
| 4,438,131 A | 3/1984 | Ehrmann et al. |
| 4,723,039 A | 2/1988 | Seitz et al. |
| 4,987,071 A | 1/1991 | Cech et al. |
| 5,589,332 A | 12/1996 | Shih et al. |
| 5,705,188 A | 1/1998 | Junichi et al. |
| 5,741,679 A | 4/1998 | George et al. |
| 5,834,186 A | 11/1998 | George et al. |
| 5,837,282 A | 11/1998 | Fenske et al. |
| 5,849,902 A | 12/1998 | Arrow et al. |
| 5,871,914 A | 2/1999 | Nathan |
| 5,989,912 A | 11/1999 | Arrow et al. |
| 6,166,197 A | 12/2000 | Cook et al. |
| 7,348,314 B2 | 3/2008 | John et al. |
| 7,404,969 B2 | 7/2008 | Chen et al. |
| 7,811,602 B2 | 10/2010 | Cullis et al. |
| 8,084,600 B2 | 12/2011 | Natt et al. |
| 8,097,716 B2 | 1/2012 | Weiler et al. |
| 8,344,128 B2 | 1/2013 | Natt et al. |
| 8,404,831 B2 | 3/2013 | Natt et al. |
| 8,404,832 B2 | 3/2013 | Natt et al. |
| 9,301,923 B2 | 4/2016 | Baryza et al. |
| 2002/0157568 A1 | 10/2002 | Adachi et al. |
| 2004/0006061 A1 | 1/2004 | Haap et al. |
| 2004/0043952 A1 | 3/2004 | Niedzinski et al. |
| 2006/0240554 A1 | 10/2006 | Chen et al. |
| 2007/0235889 A1 | 10/2007 | Hartounian et al. |
| 2008/0020058 A1 | 1/2008 | Chen et al. |
| 2008/0188675 A1 | 8/2008 | Chen et al. |
| 2008/0214437 A1 | 9/2008 | Mohapatra et al. |
| 2009/0048197 A1 | 2/2009 | Chen et al. |
| 2009/0209626 A1 | 8/2009 | Khvorova et al. |
| 2011/0224447 A1 | 9/2011 | Bowman et al. |
| 2014/0172045 A1 | 6/2014 | Yip et al. |

(Continued)

FOREIGN PATENT DOCUMENTS

| | | |
|---|---|---|
| CN | 1311189 A | 9/2001 |
| CN | 101468203 | 7/2009 |

(Continued)

OTHER PUBLICATIONS

Walsh et al, Drug Delivery System, Chapter 6, Methods in Molec. Biology, vol. 1141, pp. 109-120 ((2014). (Year: 2014).*
Belliveau et al, Molecular Therapy—Nucleic Acids, e37, pp. 1-9 (2012). (Year: 2012).*
Delmas et al, J. Colloid Science and Biotechnology, vol. 1, pp. 16-25 (2012) (Year: 2012).*

(Continued)

*Primary Examiner* — Jane J Zara

(74) *Attorney, Agent, or Firm* — Brinks Gilson & Lione

(57) ABSTRACT

Encapsulated nucleic acid nanoparticles of uniformly small particle size are produced by intersecting one or more nucleic acid streams with one or more lipid streams. The encapsulated nucleic acid nanoparticles include a nucleic acid encapsulated within a lipid nanoparticle host. Uniformly small particle sizes are obtained by intersecting an aqueous nucleic acid stream and a stream of lipids in organic solvent at high linear velocities and with total organic solvent concentrations less than 33%.

17 Claims, 4 Drawing Sheets

Specification includes a Sequence Listing.

(56) References Cited

U.S. PATENT DOCUMENTS

| | | |
|---|---|---|
| 2014/0303232 A1 | 10/2014 | Baryza et al. |
| 2016/0244756 A1 | 8/2016 | Baryza et al. |
| 2018/0049991 A1* | 2/2018 | Lee |

FOREIGN PATENT DOCUMENTS

| | | |
|---|---|---|
| EP | 0064158 | 3/1982 |
| EP | 0187702 | 1/1986 |
| EP | 0188311 | 1/1986 |
| EP | 0225543 | 11/1986 |
| EP | 1927584 A1 | 6/2008 |
| GB | 2005248 A | 4/1979 |
| JP | 2000281569 A | 10/2000 |
| JP | 2002212477 A | 7/2002 |
| JP | 51-79734 | 3/2008 |
| JP | WO2008/096690 A1 | 5/2010 |
| WO | WO 1995/008986 | 4/1995 |
| WO | WO 1997/048712 | 12/1997 |
| WO | WO 1998/027104 | 6/1998 |
| WO | WO 1998/041214 | 9/1998 |
| WO | WO 1999/007409 | 2/1999 |
| WO | WO 1999/029842 | 6/1999 |
| WO | WO 1999/032619 | 7/1999 |
| WO | WO 1999/033791 | 7/1999 |
| WO | WO 2000/001846 | 1/2000 |
| WO | WO 2000/024931 | 5/2000 |
| WO | WO 2000/026226 | 5/2000 |
| WO | WO 2000/030444 | 6/2000 |
| WO | WO 2000/044895 | 8/2000 |
| WO | WO 2000/044914 | 8/2000 |
| WO | WO 2001/029058 A1 | 4/2001 |
| WO | WO 2001/036646 A1 | 5/2001 |
| WO | WO 2002/002606 A2 | 1/2002 |
| WO | WO 2002/034771 A2 | 5/2002 |
| WO | WO 2003/018054 A1 | 3/2003 |
| WO | WO 2005/002619 A2 | 1/2005 |
| WO | WO 2005/032582 A2 | 4/2005 |
| WO | WO 2005/111066 A2 | 11/2005 |
| WO | WO 2005/121348 A1 | 12/2005 |
| WO | WO 2006/007712 A1 | 1/2006 |
| WO | WO 2006/016097 A2 | 2/2006 |
| WO | WO 2006/089264 A2 | 8/2006 |
| WO | WO 2006/091517 A2 | 8/2006 |
| WO | WO 2006/110413 A2 | 10/2006 |
| WO | WO 2006/138004 A2 | 12/2006 |
| WO | WO 2007/049155 A2 | 5/2007 |
| WO | WO 2007/076328 A2 | 7/2007 |
| WO | WO 2007/107162 A2 | 9/2007 |
| WO | WO 2007/128477 A2 | 11/2007 |
| WO | WO 2008/020058 A2 | 2/2008 |
| WO | WO 2008/020330 A2 | 2/2008 |
| WO | WO 2008/103276 A2 | 8/2008 |
| WO | WO 2008/137758 A2 | 11/2008 |
| WO | WO 2008/147438 A2 | 12/2008 |
| WO | WO 2008/147824 A2 | 12/2008 |
| WO | WO 2009/016515 A2 | 2/2009 |
| WO | WO 2009/031043 A2 | 3/2009 |
| WO | WO 2009/082817 A1 | 7/2009 |
| WO | WO 2009/086558 A1 | 7/2009 |
| WO | WO 2009/104092 A2 | 8/2009 |
| WO | WO 2009/109860 A2 | 9/2009 |
| WO | WO 2009/127060 A1 | 10/2009 |
| WO | WO 2009/129387 A2 | 10/2009 |
| WO | WO 2009/129395 A1 | 10/2009 |
| WO | WO 2010/009065 A2 | 1/2010 |
| WO | WO 2010/054401 A1 | 5/2010 |
| WO | WO 2010/054405 A1 | 5/2010 |
| WO | WO 2010/054406 A1 | 5/2010 |
| WO | WO 2010/119343 A2 | 10/2010 |
| WO | WO 2011/000108 A1 | 1/2011 |
| WO | WO 2011/005799 A2 | 1/2011 |
| WO | WO 2011/022460 A1 | 2/2011 |
| WO | WO 2011/076807 A2 | 6/2011 |
| WO | WO 2011/140627 * | 11/2011 |
| WO | WO 2011/140627 A1 | 11/2011 |
| WO | WO 2011/141704 A1 | 11/2011 |
| WO | WO 2011/150347 A2 | 12/2011 |
| WO | WO 2012/006372 A1 | 1/2012 |
| WO | WO 2013/086354 A1 | 6/2013 |
| WO | WO 2014/172045 * | 3/2014 |
| WO | WO 2015/051044 A2 | 4/2015 |

OTHER PUBLICATIONS

Akhtar, S. et al., "Cellular Uptake and Intracellular Fate of Antisense Ologonucleotides," Trends in Cell Biology, vol. 2, (1992) pp. 139-144.

Akhtar, S., et al., "Nonviral delivery of synthetic siRNAs in vivo," The Journal of Clincal Investigation—Review series, 117, 12, 2007, pp. 3623-3632.

Allen, T.M. et al., "Liposomal Drug Delivery Systems: From Concept to Clinical Applications," Advanced Drug Delivery Reviews, 65 (2013) pp. 36-48.

Allshire, "RNAi and Heterochromatin—a Hushed-Up Affair," Science, 297, 2002, pp. 3623-3632.

Anonymous, "Manufacturing Technology," Precision Nanosystems, web.archive.org/web/20150921164410/http://www.nanoassemblr.com/technology/.

Bailey, et al., "Modulation of Membrane Fusion by Asymmetric Transbilayer Distributionsof Amino Lipids," Biochemistry, 33, 1994, pp. 12573-12580.

Bangham, A.D. et al., "Diffusion of Univalent Ions Across the Lamellae of Swollen Phospholipids," Journal of Molecular Biology, vol. 13, Issue 1, (1965) pp. 238-252. Abstract Only.

Bass, "The short anser," Nature-news and views, 411, 2001, pp. 428-429.

Behlke, "Progress Towards in Vivo Use of siRNAs," Molecular Therapy—Review Article, 13, 4, 2006, pp. 644-670.

Belliveau, Nathan M., et al., "Microfluidic Synthesis of Highly Potent Limit-size Lipid Nanoparticles for In Vivo Delivery of siRNA," Molecular Therapy Nucleic Acids, vol. 1, No. 8, Aug. 1, 2012, pp. e37-1.

Belliveau, Nathan M., et al., "Supplementary Information Microfluidic Synthesis of Highly Potent Limit-size Lipid Nanoparticles for in Vivo Delivery of siRNA,". Molecular Therapy Nucleic Acids (2012), pp. 1, e37.

Berdel, et al., "Lack of therapeutic activity of the lipoidal amine CP-46.665 in rodent tumors and human nonseminomatous germ cell tumors growing in nude mice," Cancer Letters, 38, 1-2, 1987, pp. 191-197, abstract only.

Berdel, et al., "Cylotoxicity of the Alkyl-linked Lipoidal Amine 4-Aminomethyl-1-[2,3-(di-n-decyloxy)-n-propyl]-4-phenylpiperidine (CP-46,665) in Cells from Human Tumors and Leukemias," Cancer Research 45, 1985, pp. 1206-1213.

Berdel, et al., "Ether lipid derivatives: antineoplastic activity in vitro and the structure-activity relationship," Lipids, 21, 4, 1986, pp. 301-304, abstract only.

Berdel, et al., "Studies on the Role of Ether Lipids as Purging Agents in Autologous Bone Marrow Transplantation," In the Pharmacological Efect of Lipids III (The American Oil Chemists' Society, Champaign, IL), 1989, pp. 338-360.

Berens, et al., "Effects of structural modifications of ether lipids on antiproliferative activity against human glioma cell lines," Anticancer Research, 13, 2, 1993, pp. 401-405, abstract only.

Brighham, K.L. et al., "Rapid Communication: In vivo Transfection of Murine Lungs with a Functioning Prokaryotic Gene Using a Liposome Vehicle," The American Journal of the Medical Sciences, vol. 298, No. 4, (1989) pp. 278-281.

Brody, et al., "Aptamers as therapeutic and diagnostic agents," J. Biotechnol, 74, 1, 2000, pp. 5-13, abstract only.

Cech, T.R., PhD., "Ribozymes and Their Medical Implications," JAMA, vol. 260, No. 20, (1988) pp. 3030-3034.

Chemical Abstracts Service, Columbus, Ohio, US; Sep. 19, 2008, 1050504-57-8.

Cook, "Medicinal chemistry of antisense oligonucleotides—future opportunities," Anticancer Drug Des., 6, 6, 1991, pp. 585-607, abstract only.

(56) References Cited

OTHER PUBLICATIONS

Crooke, "Advances in Understanding the Pharmacological Properties of Antisense Oligonucleotides," Adv. Pharmacal, 40, 1997, pp. 1-49, abstract only.
Crooke, "Antisense Therapeutics," Biotechnol. Genet. Eng. Ref.; 15, 1998, pp. 121-157.
Crooke, "Progress in Antisense Technology: The End of the Beginning," Methods in Enzymology, 313, 2000, pp. 3-45.
Danhauser, et al., "Structure-cyloloxicity studies on alkyl-lysophospolipids and some analogs in leukemic blasts of human orgin in vitro," Lipids, 22, 11, 1987, pp. 911-915, abstract only.
Databse: XP-002633768—RN: 1050504-57-8 (Compound) Registry (2008).
Databse: XP-002633767—Preparation and formulation of cholesteryl-containing cationic lipid nanoparticle used for deliveryvarous bioi. Active mols. To cells (2008).
Delgado, et al, "The uses and properties of PEG-linked proteins," Cril. Rev. Ther. Drug Carrier Syst., 9, 3-4, 1992, pp. 249-304, abstract only.
Delihas, et al., "Natural Antisense RNA/target RNA interactions: Possible models for antisense oligonucleotide drug design," Nature Biotechnology-Review, 15, 8, 1997, pp. 751-753.
Ding, et al., "Nonionic Surfactant Modified Cationic Liposomes Mediated Gene Transfection in Vitro and in the Mouse Lung," Bioi. Pharm. Bull, 32, 2, 2009, pp. 311-315.
Duda, et al., "Reversal of Chemotherapeutically Induced Defective Wound Healing With CP-46,665," Surgical Forum, 36, 1985, pp. 419-421.
Duval-Valentin, G. et al., "Specific inhibiition of Transcription by Triple Helix-Forming Oligonucleotides," Proc. Natl. Acad. Sci. USA, Biochemistry, vol. 89, (1992) pp. 504-508.
Egbe, Daniel, et al., "Supramolecular Ordering, Thermal Behavior, and Photophysical, Electrochemical, and Electroluminescent Properties of Alkoxy-Substituted Yne-Containing Poly(phenyiene-vinyiene)s," Macromolecules, vol. 37, No. 20, Oct. 1, 2004, pp. 7451-7463.
Egholm, M. et al., "PNA Hybridizes to Complementary Oligonucleotides Obeying the Watson-Crick Hydrogen-Bonding Rules," Nature, vol. 365 (1993) pp. 566-568.
Elbashir, et al., "Functional anatomy of siRNAs for mediating efficient RNAi in Drosophila melanogaster embryo lysate," EMBO J, 2001, pp. 6877-6888.
Elbashir, S.M. et al., "Duplexes of 21-Nucleotide RNAs Mediate RNA Interference in Cultured Mammalian Cells," Nature, vol. 411, (2001) pp. 494-498.
European Search Reprot dated Mar. 31, 2017.
Faisini, S. et al., "Advances in Lipid-Based Platforms for RNAi Therapeutics," J. Med. Chem., (2013) pp. A-I.
Felgner, P.L., "Particulate Systems and Polymers for In Vitro and In Vitvo Delivery of Polynucleotides," Advanced Drug Delivery Reviews, vol. 5, Issue 3, (1990) pp. 163-187, Abstract Only.
Felgner, P.L. PhD., "Cationic Lipid/Polynucleotide Condensates for In Vitro and In Vivo Polynucleotide Delivery—The Cytofectins," Journal of Liposome Research, 3 (1), (1993) pp. 3-16.
Felgner, P.L., "Lipofection: A Highly Efficient, Lipid-Mediated DNA-Transfection Procedure," Proc. Natl. Acad. Sci. USA, Biochemistry, vol. 84, (1987) pp. 7413-7417.
Freier, et al., "Improved free-energy parameters for predictions of RNA duplex stability," Proc. Natl. Acad. Sci. USA, 83, 1986, pp. 9373-9377.
Fox, K.R., "Targeting DNA with Triplexes," Current Medicinal Chemistry, 7, (2000), pp. 17-37.
Gallas, A. et al., "Chemistry and Formulations for siRNA Therapeutics," Chem. Soc. Rev., 42, (2013) pp. 7983-7997.
Geall, A.J. et al., "Nonviral Delivery of Self-Amplifying RNA Vaccines," PNAS, vol. 109, No. 36, (2012) pp. 14604-14609.
Giuliani, M.M. et al., "A Universal Vaccine for Serogroup B Meningococcus," PNAS, vol. 103, No. 29, (2006) pp. 10834-10839.
Gold, et al., "Diversity of Oligonucleotide Functions," Annual Review of Biochemistry, 67, 1995, pp. 763-797, abstract only.

Greenhalgh, et al., "Immunomodulators and wound healing," J. Trauma, 27, 5, 1987, pp. 510-514, abstract only.
Hall, et al., "Establishment and Maintenance of a Heterochromatin Domain," Science, 297, 2002, pp. 2232-2237.
Hammann, C. et al., "Length Variation of Helix III in a Hammerhead Ribozyme and Its Influence on Cleavage Activity," Antisense & Nucleic Acid Drug Development, 9 (1999) pp. 25-31.
Hassani, et al., "Lipid-mediated siRNA delivery down-regulates exogenous gene expression in the mouse brain at picomolar levels," J. Gene Med., 7, 2005, pp. 198-207.
Hegemann, et al., "Changes of epidermal cell morphology and keratin expression induced by inhibitors of protein kinase C," Journal of Dermatological Sicence, 3, 2, 1992, pp. 103-110, abstract only.
Hermann, et al., "Adaptive Recognition by Nucleic Acid Aptamers," Science-Review: Biochemistry, 287, 2000, pp. 820-825.
Heyes, et al., "Cationic lipid saturation influences intracellular delivery of encapsulated nucleic acids," Journal of Controlled Release, 107, 2005, pp. 276-287.
Huang, et al., "Sterol-Modified Phospholipids: Cholesterol and Phospholipid Chimeras with Improved Biomembrane Properties," J. Am. Chem. Soc., 130, 46, 2008, pp. 15702-15712.
Huang, et al., "Disterolphospholipids: Nonexchangeable Lipids and Their Application to Liposomal Drug Delivery," Agnew, Chem. Int. Ed.—Communications, Drug Nanocarriers, 48, 2009, pp. 4146-4149.
Hutvagner, et al., "A microRNA in a Multiple-Turnover RNAi Enzyme Complex," Science, 297, 2002, pp. 2056-2060.
International Search Report and Written Opinion for International Patent Application No. PCT/US2014/070882, dated May 7, 2015, 10 pages.
International Search Report for corresponding International Patent Application No. PCT/IB2014/059503 dated Jul. 30, 2014.
International Preliminary Report on Patentability for corresponding International Patent Application No. PCT/IB2014/059503 dated Sep. 8, 2015.
International Preliminary Report on Patentability for corresponding International Patent Application PCT/US2014/070891 dated Jun. 21, 2016.
International Search Report on Patentability for corresponding International Patent Application PCT/US2014/070882 dated Jul. 5, 2015.
International Search Report for corresponding International Patent Application PCT/US2014/070891 dated Feb. 24, 2015.
International Search Report for corresponding International Patent Application PCT/US2015/039879 dated Dec. 3, 2015.
International Search Report for corresponding International Patent Application PCT/US2015/048535 dated Nov. 6, 2015.
Jadhav, Vasant, et al., "Preparation and formulation of cholesteryl containing cationic lipid nanoparticle used for delivering various boil. Active mols. To cells," Chemical Abstracts Service, Columbus, Ohio, Aug. 29, 2008.
Janowski, B.A. et al., "Inhibiting Gene Expression at Transcription Start Sites in Chromosomal DNA with Antigene RNAs," Nature Chemical Biology, vol. 1, No. 4, (2005) pp. 216-222.
Jayaraman, M. et al., "Maximizing the Potency of siRNA Lipid Nanoparticles for Hepatic Gene Silencing In Vivo," Angew. Chem. Int. Ed., 51, (2012) pp. 8529-8533.
Jayasena, "Aptamers: An Emerging Class of Molecules That Rival Antibodies in Diagnostics," Clinical Chemistry, 45, 9, 1999, pp. 1628-1650.
Jeffs, L.B. et al., "A Scalable, Extrusion-Free Method for Efficient Liposomal Encapsulation of Plasmid DNA," Pharmaceutical Research, vol. 22, No. 3, (2005) pp. 362-372.
Jensen, et al., "Exploring the immunotherapeutic potential of two lipoidal amines," In Human Cancer Immunology: Nev. Immunomodulating agents and biological response modifiers, Serrou, et al., editors [NY: Elsevier Science Publishing Company Inc.], 3, 1982, pp. 55-63.
Jenuwein, "An RNA-Guided Pathway for the Epigenome," Science, 297, 2002, pp. 2215-2218.
Kitada, S., et al., "Hydrophobic tag-assisted liquid-phase synthesis of a growth hormone-inhibiting peptide somatostatin," Bioorganic

(56) References Cited

OTHER PUBLICATIONS

& Medicinal Chemistry Letters, Pergamon, Amsterdam, NL, vo. 21, No. 15, Jun. 1, 2011, pp. 4476-4479.
Kitada, S., et al., "Supporting information Hydrophobic tag-assisted solution-phase synthesis of a growth hormone-inhibiting peptide somatostatin 4 5," Bioorganic & Medicinal Chemistry Letters, vol. 21, 15, Aug. 1, 2011, pp. 4476-4479.
Kitada, S., et al., "Soluble-support-assisted Electrochemical Reactions: Application to Anodic Disulfide Bond Formation," Organic Letters, vol. 14, No. 23, Dec. 7, 2012, pp. 5960-5963.
Kraynack, B., et al., "Small interfering RNAs containing full 2'-O-methylribonucleotide-modified sense strands display Argonaute2/eIF2C2-dependent activity," Cold Spring Harbor Laboratory Press, RNA, 2006, 12, pp. 163-176.
Kusser, "Chemically modified nucleic acid aptamers for in vitro selections: evolving evolution," J. Biotechnol, 74, 1, 2000, pp. 27-38, abstract only.
Leinweber, "Possible Physiological Roles of Carboxylic Ester Hydrolases," Drug Metabolism Reviews, 18, 4, 1987, pp. 379-439.
Leung, A.K.K. et al., Lipid Nanoparticles Containing siRNA Synthesized by Microfluidic Mixing Exhibit an Electron-Dense Nanostructured Core, *J. Phys. Chem. C.* 116, (2012) pp. 18440-18450.
Livingston, et al., "The Serologic Response to Meth a Sarcoma Vaccines After Cyclophosphamide treatment is Additionally Increased by Varous Adjuvants," The Journal of Immunology, 135, 2, 1985, pp. 1505-1509.
Lorenz, et al., "Steroid and lipid conjugates of siRNAs to enhance cellular uptake and gene silencing in liver cells," Bioorganic & Medicinal Chemistry Letters, 14, 2004, pp. 4975-4977.
Maier, M.A. et al., "Biodegradable Lipids Enabling Rapidly Eliminated Lipid Nanoparticles for Systemic Delivery of RNAi Therapeutics," *Molecular Therapy*, vol. 21, No. 8, (2013) pp. 1570-1578.
Maurer, N. et al., "Spontaneous Entrapment of Polynucleotides Upon Electrostatic Interaction with Ethanol-Destabilized Cationic Liposomes," *Biophysical Journal*, vol. 80, (2001) pp. 2310-2326.
Maslov, et al., "Synthesis of alkyl glycerolipids with various cationic groups linked directly to the glycerol backbone," Russian Chemical Bulletin, 48, 7, 1999, pp. 1369-1372.
McManus, et al., "Gene silencing using micro-RNA designed hairpins," RNA, 8, 2002, pp. 842-850.
Mochizuki, S.; Kamikawa, Y.; Nishina, K.; Fujii, S.; Hamada, E.; Kusuki, S.; Matsuo, T.; Sakurai, K. "Relationship Between DNA-Transfection Efficiency and Chemical Structures of Aromatic Cationic Lipids," *Bull. Chem. Soc. Jpn.*, 2012, 85, 354-359.
Modest, et al., "Pharmacological Effects and Anticancer Activity of New Ether Phospholipid Analogs," In the Pharmacological Effect of Lipids III: Role of Lipids in Cancer Research; Kabara, et al., editors (The American Oil Chemists Society—Champaign, IL), 1989, pp. 330-337.
Morrissey, D. V. et al., "Potent and Persistent In Vivo Anti-HBV Activity of Chemically Modified siRNAs," *Nature Biotechnology*, vol. 23, No. 8, (2005) pp. 1002-1007.
Noseda, et al., "In Vitro Antiproliferative Activity of Combinations of Ether Lipid Analogues and DNA-interactive Agents against Human Tumor Cells," Cancer Research, 48, 1988, pp. 1788-1791.
Obika, S. et al., "Symmetrical Cationic Triglycerides: An Efficient Synthesis and Application to Gene Transfer," *Bioorganic & Medicinal Chemistry*, 9 (2001) pp. 245-254.
Okamoto, et al., "Elimination of Leukemic Cells by the Combined Use of Ether Lipids in Vitro," Cancer Research, 47, 1987, pp. 2599-2603, abstract.
Ouchi, et al., "Synthesis and antitumor activity of poly(ethylene glycol)s linked to 5-fluorouracil via a urethane or urea bond," Drug Des. Discov., 9, 1, 1992, pp. 93-105, (Abstract only).
Pal-Bhadra, et al., "Heterochromatic Silencing and HP1 Localization in *Drosophila* Are Dependent on the RNAi Machinery," Sicence Reports, 303, 2004, pp. 669-672.

Pettit, G.R.; Blonda D.S.; Harrington, E.C. "Antineoplastic Agents IX. N-Benzyl-N-Bis(2-Haloethyl)Amines," *Canadian Journal of Chemistry*, 1963, 41, 2962-2968.
Player, M.R. et al., "The 2-5A System: Modulation of Viral and Cellular Processes Through Acceleration of RNA Degradation," *Pharmacol. Ther.*, vol. 78, No. 2 (1998) pp. 55-113.
Praseuth, D. et al., "Triple Helix Formation and the Antigene Strategy for Sequence-Specific Control of Gene Expression," *Biochimica et Biophysica Acta*,1489, (1999) pp. 181-206.
Ravasio, et al., "Selective Hydrogenations Promoted by Copper Catalysts. 1. Chemoselectivity. Regioselectivity, and Steroselectivity in the Hydrogeneration of 3-Substituted Steriods," J. Org. Chem, 56, 1991, pp. 4329-4333.
Reinhart, et al., "MicroRNAs in plants," Genes Dev., 16, 2002, pp. 1616-1626.
Reinhart, et al., "Small RNAs Correspond to Centromere Heterochromatic Repeats," Science-Molecular Biology, 297, 2002, pp. 1831.
Rejman, J. et al., "Characterization and Transfection Properties of Lipoplexes Stabilized with Novel Exchangeable Polyethylene Glycol-Lipid Conjugates," *Biochimica et Biophysica Acta*, 1660 (2004) pp. 41-52.
Ren, T.; Liu D. "Synthesis of Targetable Cationic Amphiphiles," *Tetrahedron Letters*, 1999, 40, 7621-7625.
Ren, T.; Zhang, G.; Song, Y.K.; Liu, D. "Synthesis and Characterization of Aromatic Ring-Based Cationic Lipids for Gene Delivery In Vitro and In Vivo," *J. Drug Targeting*, 1999, 7, 285-292.
Romberg, B. et al., "Sheddable Coatings for Long-Circulating Nanoparticles," *Pharmaceutical Research*, vol. 25, No. 1., (2008) pp. 55-71.
Saalfrank, R.W.; Deutscher, C.; Sperner, S.; Nakajima, T.; Ako, A.M.; Uller, E.; Hampel, F.; Heinemann, F.W. "Six-Membered Metalla-coronands. Synthesis and Crystal Packing: Columns, Compartments, and 3D-Networks," *Inorg. Chem.*, 2004, 43, 4372-4382.
Schmajuk, et al., "Antisense Oligonucleotides with Different Backbones," The Journal of Biological Chemistry, 274, 31, 1999, pp. 21783-21789.
Semple As C., et al., "Efficient encapsulation of antisense oligonucleotides in lipid vesicles using ionizable aminolipids: formation of novel small multilamellar vesicle structures," Nature Biotechnoloogy, vol. 28, No. 2, Feb. 2010, pp. 172-176.
Semple, S.C. et al. "Rational Design of Cationic Lipids for siRNA Delivery," *Nature Biotechnology*, vol. 28, No. 2., (2010) pp. 172-178.
Shoji, et al., "Inhibition of phospholipid/Ca2+dependent protein kinase and phosphorylation of leukemic cell proteins by CP-46, 665-1, a novel antineoplastic lipoidal amine," Biochemical and Biophysical Research Communications, 127, 2,1985, pp. 590-595, abstract only.
Silverman, R.H. et al., "Selective RNA Cleavage by Isolated RNase L Activated with 2-5A Antisense Chimeric Oligonucleotides," *Methods of Enzymology*, vol. 313, (1999) pp. 522-533.
Spagnou, et al., "Lipidic Carriers of siRNA: Differences in the Formulation, Cellular Uptake, and Delivery with Plasmid DNA," Biochemistry, 43, 2004, pp. 13348-13356.
Stein, C.A. et al., "Antisense Oligonucleotides as Therapeutic Agents—Is the Bullet Really Magical," Science, vol. 261 (1993) pp. 1004-1012.
Stinnett, et al., "Synthetic Immunomodulators for Prevention of Fatal Infections in a Burned Guinea Pig Model," Annals of Surgery, 198, 1, 1983, pp. 53-57.
Storme, et al., "Effect of lipid derivatives on invasion in vitro and on surface glycoproteins of three rodent cell types," Lipids, 22, 11, 1987, pp. 847-850, abstract only.
Sullenger, et al., "Overexpression of TAR Sequences Renders Cells Resistant to Human Immunodeficiency Virus Replication," Cell, 63, 1990, pp. 601-608.
Sun, "Technology evaluation: SELEX, Gilead Sciences Inc.," Curr. Opin. Mol. Ther., 2, 1, 2009, pp. 100-105, abstract only.
Torrence, P.F. et al., "Targeting RNA for Degradation with a (2'-5') Oligoadenylate-Antisense Chimera," *Proc. Natl. Acad. Sci. USA*, Biochemistry, vol. 90, (1993) pp. 1300-1304.

(56) References Cited

OTHER PUBLICATIONS

Turner, et al., "Improved Parameters for Prediction of RNA Structure," Cold Spring Harbor Symposia on Quantitative Biology, Vo. LII, 1987, pp. 123-133.
Turner, et al., "Free Energy Increments for Hydrogen Bonds in Nucleic Acid Base Pairs," J. Am. Chern. Soc., 109, 1987, pp. 3783-3785.
Vaugn, et al., "It's a Small RNA World, After All," Science-Special Section, Viewpoint, 309, 2005, pp. 1525-1526.
Verdel, et al., "RNAi-Medialed Targeting of Heterochromatin by the RITS Complex," Science, 303, 2004, pp. 672-676.s.
Volger, et al., "Comparison of selective cytotoxicity of alkyl-lysophospholipids," Lipids, 26, 12, 1991, pp. 1418-1423, abstract only.
Volger, et al., "Experimental Studies on the Role of Alkyl Lysophospholpids in Autologous Bone Marrow Transplantation," Lipids, 22, 11, 1987, pp. 919-924.
Volpe, et al., "Regulation of Heterochromatic Silencing and Histone H3 Lysine-9 Methylation by RNAi," Science, 297, 2002, pp. 1833-1837.
Walsh, Colin et al., "Microfluidic-Based Manufacture of siRNA-Lipid Nanoparticles for Therapeutic Applications," Methods in molecular biology, Feb. 3, 2014, Humana Press, Inc., vol. 1141, pp. 109-120, abstract.
Waymack, et al., "Effect of Two New Immunomodulators on Normal and Burn Injury Neutrophils and Macrophages," Journal of Burn Care Reabilitation, 8, 1, 1987, pp. 9-14.
Waymack, et al., "Effect of Immunomodulators on Macrophage Function in Burned Animals," Surgical Forum, 36, 1985, pp. 110-112.
Waymack, et al., "Mechanisms of action of two new immunomodulators," Arch. Surg., 120, 1, 1985, pp. 43-48, abstract only.
Wermuth, "Designing Prodrugs and Bioprecursors," The Practice of Medicinal Chemistry, Designing Prodrugs and Bioprecursors [$2^{nd}$ Edition] [ISBN: 0-12-744481-5][Eisevier], 2003, pp. 561-585.
Werner, M. et al., "The Effect of Base Mismatches in the Substrate Recognition Helices of Hammerhead Ribozymes on Binding and Catalysis," *Nucleic Acids Research*, vol. 23, No. 12 (1995) pp. 2092-2096.
Wolff, et al., "CP-46,665-1: A Novel Lipoidal Amine with Antimetastatic and Immunomodulatory Properties," Cancer Immunol. Immunother: 12, 1982, pp. 97-103.
Xie, et al., "Harnessing in vivo siRNA delivery for drug discovery and therapeutic development," Drug Discovery Today, 11, 1-2, 2006, pp. 67-73.
Xu, Y. et al., "Mechanism of DNA Release from Cationic Liposome/DNA Complexes Used in Cell Transfection," *Biochemistry*, 35, (1996) pp. 5616-5623.
Zamore, P.D. et al., "Ribo-gnome: The Big World of Small RNAs," *Science*, 309 (2005) pp. 1519-1534.
Zamore, P.D. et al., "RNAi: Double-Stranded RNA Directs the ATP-Dependent Cleavage of mRNA at 21 to 23 Nucleotide Intervals," *Cell*, vol. 101, (2000), pp. 25-33.
Zhang, J. et al., "Interaction of Cholesterol-Conjugated Ionizable Amino Lipids with Biomembranes: Lipid Polymorphism, Structure-Activity Relationship, and Implications for siRNA Delivery," *Langmuir*, 27, (2011) pp. 9473-9483.
Zhang, Jingtao, et al., "Ionization behavior of amino lipids for siRNA delivery: determination of ionization constants, SAR, and the impact of lipid pKa on cationic lipid-biomembrane interactions," Langmuir: The ACS Journal of Surfaces and Colloids, vol. 27, No. 5, Mar. 1, 2011, pp. 1907-1914.
Zimmermann, T.S. et al., "RNAi-Mediated Gene Silencing in Non-Human Primates," *Nature*, vol. 441, 4, (2006) pp. 111-114.
Strickley, Robert G., "Solubilizing Excipients in Oral and Injectable Formulations," Pharmaceutical Research, vol. 21, No. 2, Feb. 2004, pp. 201-230.
Burgin, et al., "Chemically Modified Hammerhea Ribozymes with Improved Catalytic Rates," Biochemistry, 1996, 35, pp. 14090-14097.
Usman, et al., "Exploiting the chemical synthesis of RNA," TIBS 17, Sep. 1992, pp. 334-339.
Usman, et al., "Chemical modification of hammerhead ribozymes: activity and nuclease resistance," Oxford University Press, Nucleic Acids Symposium Series, No. 31, 1994, pp. 163-164.
Xu, et al., "Esterase-catalyzed dePEGylation of pH-sensitive vesicles modified with cleavable PEG-lipid derivatives," Journal of Controlled Release, Elsevier, 130, 2008, pp. 238-245.
Yamato, et al., "Enhanced specificity of HPV16 E6E7 siRNA by RNA-DNA chimera modification," Cancer Gene Therapy, Nature America, Inc., 18, 2011, pp. 587-597.

* cited by examiner

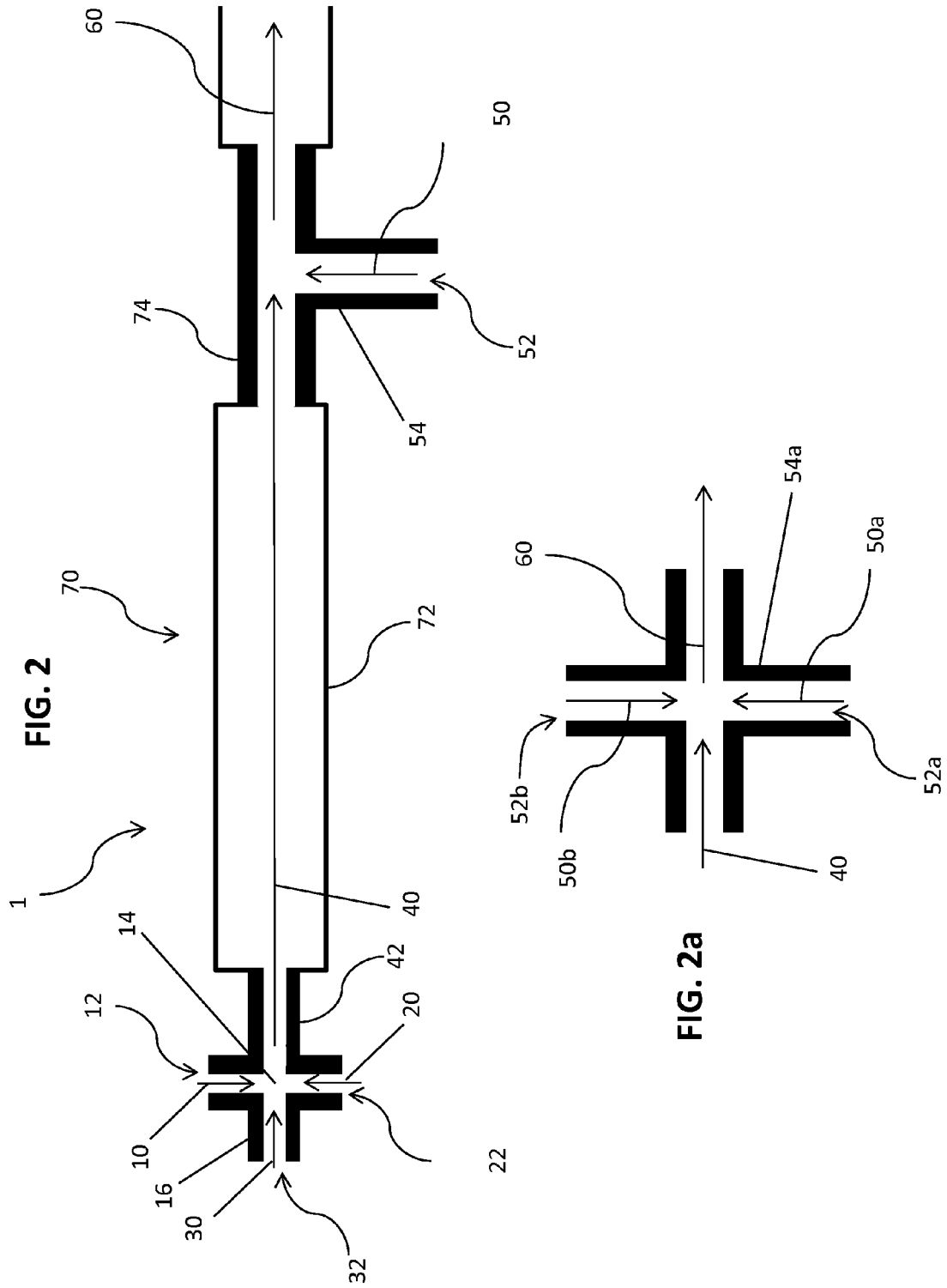

METHOD OF ENCAPSULATING A NUCLEIC ACID IN A LIPID NANOPARTICLE HOST

RELATED APPLICATIONS

This application is the U.S. National Phase under 35 U.S.C. § 371 of International Patent Application No. PCT/US2015/039879, filed Jul. 10, 2015, which claims priority to and the benefit of U.S. Provisional Application Ser. No. 62/025,224, filed Jul. 16, 2014. The entire disclosures of these applications are hereby incorporated by reference.

SEQUENCE LISTING

The instant application contains a Sequence Listing which has been submitted electronically in ASCII format and is hereby incorporated by reference in its entirety. Said ASCII copy, created on Sep. 24, 2015, is named EFS 15607-114 Sequence Listing ST25.txt and is 5 KB in size.

FIELD OF THE INVENTION

The invention generally relates to encapsulated nucleic acid nanoparticle compositions and processes and systems for producing encapsulated nucleic acid nanoparticles of uniformly small particle size.

BACKGROUND OF THE INVENTION

The delivery of biologically active agents (including therapeutically relevant compounds) to subjects is often hindered by difficulties in the compounds reaching the target cell or tissue. In particular, the trafficking of many biologically active agents into living cells is highly restricted by the complex membrane systems of the cells. These restrictions can result in the need to use much higher concentrations of biologically active agents than is desirable to achieve a result, which increases the risk of toxic effects and side effects. One solution to this problem is to utilize specific carrier molecules and carrier compositions which are allowed selective entry into the cell. Lipid carriers, biodegradable polymers and various conjugate systems can be used to improve delivery of biologically active agents to cells.

One class of biologically active agents that is particularly difficult to deliver to cells is a bio therapeutic (including nucleosides, nucleotides, polynucleotides, nucleic acids and derivatives, such as mRNA and RNAi agents). In general, nucleic acids are stable for only a limited duration in cells or plasma. The development of RNA interference, RNAi therapy, mRNA therapy, RNA drugs, antisense therapy and gene therapy, among others, has increased the need for an effective means of introducing active nucleic acid agents into cells. For these reasons, compositions that can stabilize and deliver nucleic acid-based agents into cells are of particular interest.

The most well-studied approaches for improving the transport of foreign nucleic acids into cells involve the use of viral vectors or formulations with cationic lipids. Viral vectors can be used to transfer genes efficiently into some cell types, but they generally cannot be used to introduce chemically synthesized molecules into cells.

An alternative approach is to use delivery compositions incorporating cationic lipids which interact with a biologically active agent at one part and interact with a membrane system at another part. Such compositions are reported to provide liposomes, miscelles, lipoplexes, or lipid nanoparticles, depending on the composition and method of preparation (for reviews, see Felgner, 1990, Advanced Drug Delivery Reviews, 5, 162-187; Felgner, 1993, J. Liposome Res., 3, 3-16; Gallas, 2013, Chem. Soc. Rev., 42, 7983-7997; Falsini, 2013, J. Med. Chem. dx.doi.org/10.1021/jm400791q; and references therein).

Since the first description of liposomes in 1965 by Bangham (J. Mol. Biol. 13, 238-252), there has been a sustained interest and effort in developing lipid-based carrier systems for the delivery of biologically active agents (Allen, 2013, Advanced Drug Delivery Reviews, 65, 36-48). The process of introducing functional nucleic acids into cultured cells by using positively charged liposomes was first described by Philip Felgner et al. *Proc. Natl. Acad. Sci.*, USA, 84, 7413-7417 (1987). The process was later demonstrated in vivo by K. L. Brigham et al., *Am. J. Med. Sci.*, 298, 278-281 (1989). More recently, lipid nanoparticle formulations have been developed with demonstrated efficacy in vitro and in vivo. (Falsini, 2013, J. Med. Chem. dx.doi.org/10.1021/jm400791q; Morrissey, 2005, Nat. Biotech., 23, 1002-1007; Zimmerman, 2006, Nature, 441, 111-114; Jayaraman, 2012, Angew. Chem. Int. Ed., 51, 8529-8533.)

Lipid formulations are attractive carriers since they can protect biological molecules from degradation while improving their cellular uptake. Out of the various classes of lipid formulations, formulations which contain cationic lipids are commonly used for delivering polyanions (e.g. nucleic acids). Such formulations can be formed using cationic lipids alone and optionally including other lipids and amphiphiles such as phosphatidylethanolamine. It is well known in the art that both the composition of the lipid formulation as well as its method of preparation affect the structure and size of the resultant aggregate (Leung, 2012, J. Phys Chem. C, 116, 18440-18450).

Several techniques have been reported to encapsulate a nucleic acid in a lipid nanoparticle, including detergent dialysis, extrusion, high speed mixing, and stepwise dilution. Existing approaches to nucleic acid encapsulation, however, suffer from low encapsulation rates or non-scalability, produce nanoparticles that lack a high degree of uniformity, and/or do not achieve average particle sizes less than 80 nm. There is a need, therefore, for new methods to encapsulate nucleic acids in a lipid nanoparticle that produces a high degree of encapsulation, is scalable, and produces nanoparticles of uniform size with an average particle diameter less than 80 nm.

SUMMARY OF THE INVENTION

The present invention relates to an improved method for encapsulating a nucleic acid in a lipid nanoparticle host. The method is scalable and provides for the formation of encapsulated nucleic acid nanoparticles having small average particle sizes (e.g., <80 nm), improved uniformity of particle size, and a high degree of nucleic acid encapsulation (e.g., >90%). Nanoparticles produced by the processes of the invention possess long term stability.

A first aspect of the invention provides a method of encapsulating a nucleic acid in a lipid nanoparticle host by joining one or more lipid streams with one or more nucleic acid streams and flowing the joined streams to provide a first outlet solution of encapsulated nucleic acid nanoparticles. Each lipid stream comprises a mixture of one or more lipids in an organic solvent (e.g., ethanol). Each nucleic acid stream comprises a mixture of one or more nucleic acids in an aqueous solution. At the intersection point of the lipid and nucleic acid streams, each stream is characterized by a linear velocity. The one or more lipid nanoparticle streams have a combined linear velocity of greater than or equal to about 1.5 meters/second. Likewise, the one or more nucleic acid streams have a combined linear velocity of greater than or equal to about 1.5 meters/second. The final concentration of organic solvent following joining and mixing of the lipid and nucleic acid streams is in an amount that minimizes aggregation (e.g., less than 33%). In certain embodiments, the final concentration of organic solvent in the first outlet solution is about 20% to about 25%. In certain embodiments according to the first aspect, the joined lipid and nucleic acid streams are diluted with a dilution solvent to provide the first outlet solution. In other embodiments according to the first aspect, the combined linear velocity of the combined nucleic acid stream(s) is about 3 to about 14 meters/second and the combined linear velocity of the lipid stream(s) is about 1.5 to about 7 meters/second.

In a second aspect of the invention, the first outlet solution is further processed by dilution, incubation, concentration, and dialysis. In certain embodiments according to the second aspect, the dialyzed solution may also be sterile filtered. Encapsulated nucleic acid nanoparticles produced by the processes of the second aspect have long-term stability.

In a third aspect of the invention, the encapsulated lipid nanoparticles produced by the processes of the invention have an average diameter less than about 80 nm. In certain embodiments the nanoparticles have an average diameter of about 30 to about 80 nM. In preferred embodiments, the nanoparticles have an average diameter of less than about 70 nm (e.g., about 40-70 nm).

A fourth aspect of the invention provides an encapsulated nucleic acid nanoparticle composition comprising a pharmaceutically acceptable carrier, a lipid nanoparticle host, and a nucleic acid, where the encapsulated nucleic acid nanoparticle has an average diameter from about 40 nm to about 70 nm.

BRIEF DESCRIPTION OF THE DRAWINGS

FIG. 2 illustrates a representative system for producing encapsulated nucleic acid nanoparticles.

FIG. 2a illustrates an alternate embodiment of a dilution chamber for use in the system of FIG. 2

DETAILED DESCRIPTION 1.0 General

Figure 1:
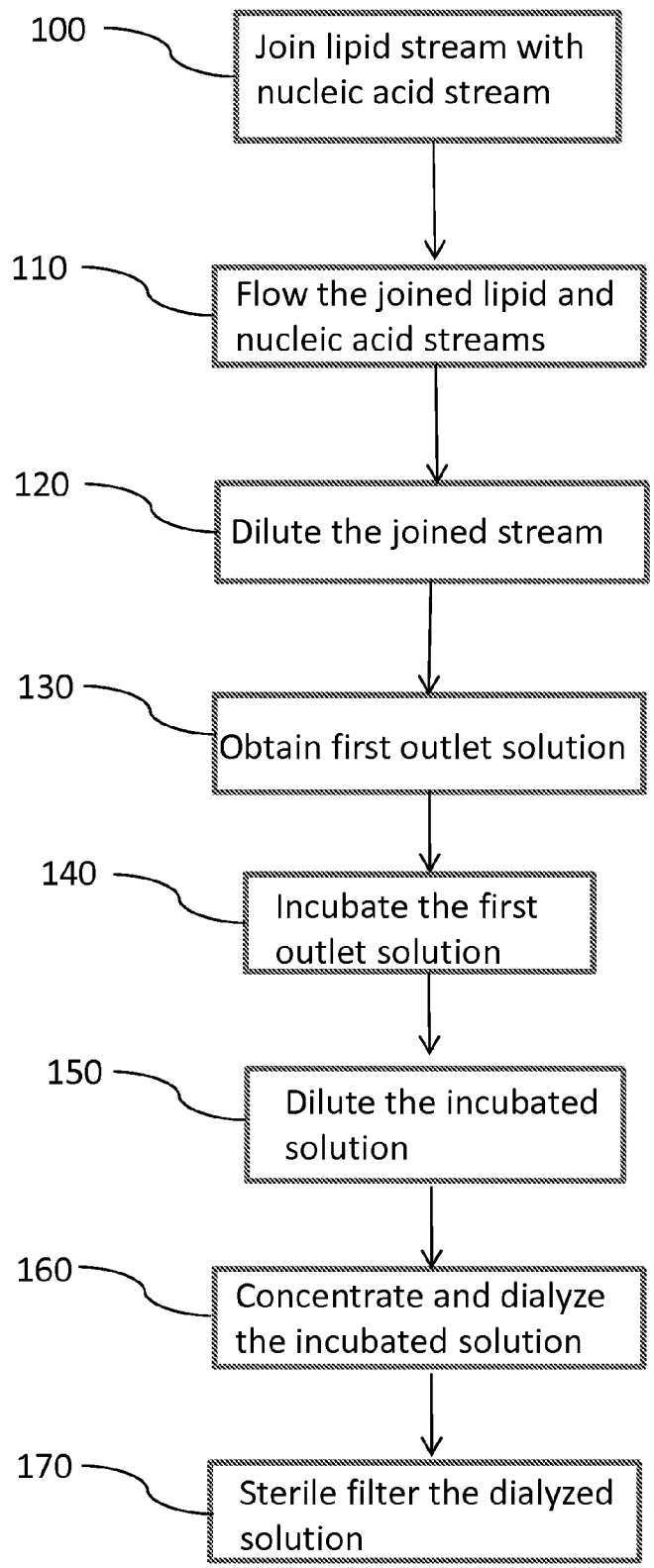
FIG. 1 illustrates a flow diagram of an exemplary process for preparing and processing encapsulated nucleic acid nanoparticles.

The present invention provides processes for producing encapsulated nucleic acid nanoparticles with uniformly small particle sizes. Shown in FIG. 1 is a representative flow chart generally outlining the steps of one embodiment of the invention. In step 100, one or more lipid streams are joined at a first intersection point with one or more nucleic acid streams to provide a first joined stream. The first joined stream is then flowed (step 110) to permit association of the individual streams of the joined stream, whereupon the process of lipid nanoparticle assembly and nucleic acid encapsulation takes place. Depending on the particular parameters chosen for the initial nucleic acid stream(s), the joined stream may be optionally further diluted with aqueous media (step 120) to obtain the first outlet solution (step 130). Alternatively, the optional dilution step 120 may be omitted and the first outlet stream obtained directly from the flowing joined stream by use of an appropriately diluted nucleic acid stream(s) in step 100. The first outlet solution obtained at step 130 contains encapsulated nucleic acid nanoparticles.

Further processing of the first outlet solution may be performed to remove organic solvent and thereby provide the encapsulated nucleic acid nanoparticles as a formulation having long-term stability. Initially, the first outlet solution is incubated (step 140) for a period of time (e.g., 60 minutes) at room temperature, followed by dilution with aqueous media (e.g. water, citrate buffer) (step 150), concentration and dialysis (step 160), and finally sterile filtration (step 170). The dilution step 150 may dilute the organic solvent concentration by two-fold. The concentration may be by tangential flow filtration.

Surprisingly, it has been found that small and uniform particles are obtained by joining/intersecting one or more lipid streams with one or more nucleic acid streams where the combined lipid streams and the combined nucleic acid streams, each, maintain a linear velocity of greater than 1.5 meters/second and the final concentration of organic solvent upon joining/mixing the streams is less than 33% by volume. Keeping the organic solvent less than 33% inhibits aggregation of the nanoparticles, whereas the high flow rates of the invention keep particle sizes small and uniform. The processes provide for efficient encapsulation of nucleic acids.

In some embodiments, the combined linear velocity of the one or more nucleic acid streams is about 1.5 to about 14 meters/second and the combined linear velocity of the one or more lipid streams is about 1.5 to about 7 meters/second. In other embodiments, the combined linear velocity of the one or more nucleic acid streams is about 3 to about 14 meters/second and the combined linear velocity of the one or more lipid streams is about 1.5 to about 4.5 meters/second. In other embodiments, the combined linear velocity of the one or more nucleic acid streams is about 8 to about 14 meters/second and the combined linear velocity of the one or more lipid streams is about 1.5 to about 4.5 meters/second. In other embodiments, the combined linear velocity of the one or more nucleic acid streams is about 3 to about 8 meters/second and the combined linear velocity of the one or more lipid streams is about 1.5 to about 4.5 meters/second. In other embodiments, the combined linear velocity of the one or more nucleic acid streams is about 9 to about 14 meters/second and the combined linear velocity of the one or more lipid streams is about 3 to about 4 meters/second. In other embodiments, the combined linear velocity of the one or more nucleic acid streams is about 11 to about 14 meters/second and the combined linear velocity of the one or more lipid streams is about 3 to about 4 meters/second. In other embodiments, the combined linear velocity of the one or more nucleic acid streams is about 9 to about 11 meters/second and the combined linear velocity of the one or more lipid streams is about 3 to about 4 meters/second. In other embodiments, the combined linear velocity of the one or more nucleic acid streams is about 6 to about 8 meters/second and the combined linear velocity of the one or more lipid streams is about 3 to about 4 meters/second. In still other embodiments, the combined linear velocity of the one or more nucleic acid streams is about 10.2 meters/second and the combined linear velocity of the one or more lipid streams is about 3.4 meters/second. In other embodiments, the combined linear velocity of the one or more nucleic acid streams is about 6.8 meters/second and the combined linear velocity of the one or more lipid streams is about 3.4 meters/second. In still other embodiments, the combined linear velocity of the one or more nucleic acid streams is about 13.6 meters/second and the combined linear velocity of the one or more lipid streams is about 3.4 meters/second. In still other embodiments, the combined linear velocity of the one or more nucleic acid streams is about 3.4 meters/second and the combined linear velocity of the one or more lipid streams is about 1.7 meters/second. In other embodiments, the combined linear velocity of the one or more nucleic acid streams is about 3 meters/second and the combined linear velocity of the one or more lipid streams is about 1.5 meters/second. In other embodiments, the combined linear velocity of the one or more nucleic acid streams is about 14 meters/second and the combined linear velocity of the one or more lipid streams is about 7 meters/second.

2.0 Nucleic Acids

Nucleic acids suitable for use with the invention include: antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), messenger ribonucleic acid" (messenger RNA, mRNA), double-stranded RNA (dsRNA), micro-RNA (miRNA), and short hairpin RNA (shRNA) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (assymetrical interfering RNA), and siRNA with 1, 2 or more mismatches between the sense and anti-sense strand to relevant cells and/or tissues, such as in a cell culture, subject or organism. Such compounds may be purified or partially purified, and may be naturally occuring or synthetic, and may be chemically modified. In one embodiment the biologically active agent is an RNAi agent, short interfering nucleic acid (siNA), short interfering RNA (siRNA), double-stranded RNA (dsRNA), micro-RNA (miRNA), or a short hairpin RNA (shRNA) molecule. In one embodiment the biologically active agent is a RNAi agent useful for mediating RNA interference (RNAi).

A "ribonucleic acid" (RNA) is a polymer of nucleotides linked by a phosphodiester bond, where each nucleotide contains ribose or a modification thereof as the sugar component. Each nucleotide contains an adenine (A), a guanine (G), a cytosine (C), a uracil (U) or a modification thereof as the base. The genetic information in a mRNA molecule is encoded in the sequence of the nucleotide bases of the mRNA molecule, which are arranged into codons consisting of three nucleotide bases each. Each codon encodes for a specific amino acid of the polypeptide, except for the stop codons, which terminate translation (protein synthesis). Within a living cell, mRNA is transported to a ribosome, the site of protein synthesis, where it provides the genetic information for protein synthesis synthesis (translation). For a fuller description, see, Alberts B et al. (2007) *Molecular Biology of the Cell, Fifth Edition*, Garland Science.

In eukaryotes, mRNA is transcribed in vivo at the chromosomes by the cellular enzyme RNA polymerase. During or after transcription in vivo, a 5' cap (also termed an RNA cap, an RNA 7-methylguanosine cap, or an RNA m7G cap) is added in vivo to the 5' end of the mRNA. The 5' cap is terminal 7-methylguanosine residue that is linked through a 5'-5'-triphosphate bond to the first transcribed nucleotide. In addition, most eukaryotic mRNA molecules have a polyadenylyl moiety ("poly(A) tail") at the 3' end of the mRNA molecule. In vivo, the eukaryotic cell adds the poly(A) tail after transcription, often at a length of about 250 adenosine residues. Thus, a typical mature eukaryotic mRNA has a structure that begins at the 5' end with an mRNA cap nucleotide followed by a 5' untranslated region (5'UTR) of nucleotides, then an open reading frame that begins with a start codon which is an AUG triplet of nucleotide bases, that is the coding sequence for a protein, and that ends with a stop codon that may be a UAA, UAG, or UGA triplet of nucleotide bases, then a 3' untranslated region (3'UTR) of nucleotides and ending with a poly-adenosine tail. While the features of the typical mature eukaryotic mRNA are made naturally in a eukaryotic cell in vivo, the same or structurally and functionally equivalent features can be made in vitro using the methods of molecular biology. Accordingly, any RNA having the structure similar to a typical mature eukaryotic mRNA can function as a mRNA and is within the scope of the term "messenger ribonucleic acid".

The mRNA molecule is generally of a size that it can be encapsulated in a lipid nanoparticle of the invention. While the size of a mRNA molecule varies in nature depending upon the identity of the mRNA species that encodes for a particular protein, an average size for a mRNA molecule is average mRNA size is 500-10,000 bases.

The term "deoxyribonucleic acid" (DNA) as used herein refers to a polymeric nucleic acid that carries the genetic information in the cells of living organisms and many viruses. In vivo, DNA is capable of self-replication and the synthesis of RNA. DNA consists of two long chains of nucleotides twisted into a double helix and joined by hydrogen bonds between the complementary bases adenine (A) and thymine (T) or cytosine (C) and guanine (G). The sequence of the nucleotides determines individual hereditary characteristics. See, *The American Heritage® Dictionary of the English Language, Fourth Edition* (Updated in 2009). Houghton Mifflin Company.

Each of the nucleotides of a DNA polymer is linked by a phosphodiester bond in a 5' to 3' directuion. Each nucleotide contains deoxyribose or a modification thereof as the sugar component. Each nucleotide contains an adenine (A), a guanine (G), a cytosine (C), a thymine (T) or a modification thereof as the base.

Most DNA molecules existing in vivo are double-stranded helices, consisting of two long polymers in anti-parallel formation, one backbone being 3' (three prime) and the other 5' (five prime). In this double stranded formation, the bases are paired by hydrogen bonding, with adenine bonding to thymine and guanine binding to cytosine, which results in a double helix structure. Other DNA molecules are single stranded, although single stranded DNA molecules have the potential to become double stranded if they match with another single stranded DNA or RNA molecule with a complementary nucleotide sequence. For a fuller description, see, Alberts B et al. (2007) *Molecular Biology of the Cell, Fifth Edition*, Garland Science.

The sequence of the nucleotide bases along the deoxyribose backbone that encodes the genetic information. For the synthesis of proteins, the genetic information is copied into the nucleotide sequence of a mRNA molecule in a process called transcription, when the mRNA molecule is created.

DNA can exist in at least two forms, which have different sizes. The first form of DNA is a very large-sized polymer called a chromosome. A chromosome contains the genetic information for many or most of the proteins in a cell and also contains information whereby the cell can control the replication of the DNA molecule. A bacterial cell may contain one or more chromosome. A eukaryotic cell usually contains more than one cell chromosome, each chromosome.

The second form of DNA is a shorter sized form. Many DNA molecules of the second form are of a size that it can be encapsulated in a lipid nanoparticle of the invention. Some of these shorter forms of DNA can be of a size to usefully encode for proteins. Examples of these second, shorter, useful forms of DNA include plasmids and other vectors. For a fuller description, see, Alberts B et al. (2007) *Molecular Biology of the Cell, Fifth Edition*, Garland Science.

A plasmid is a small DNA molecule that is physically separate from, and can replicate independently of, chromosomal DNA within a cell. Plasmids commonly exist in vivo as small circular, double-stranded DNA molecules. In nature, plasmids carry genes that can be transcribed and translated to proteins that may benefit survival of an organism (e.g. antibiotic resistance). In nature, plasmids can frequently be transmitted from one organism to another by horizontal gene transfer. Artificial or recombinant plasmids are widely used in molecular biology, serving to permit the replication of recombinant DNA sequences and the expression of useful proteins within host organisms. Plasmid sizes can vary from 1 to over 25 kilobase pairs. A recombinant plasmid can be recombinantly made to be of a size that it can be encapsulated in a lipid nanoparticle of the invention.

In molecular biology, a vector is a DNA molecule used as a vehicle to artificially carry genetic material from one cell or from a biochemical reaction in vitro into another cell, where the DNA can be replicated and/or expressed. A vector containing foreign DNA is termed recombinant. Among the types of useful vectors are plasmids and viral vectors. Insertion of a vector into the target cell is usually called transformation for bacterial cells, transfection for eukaryotic cells, although insertion of a viral vector is often called transduction.

Viral vectors are generally recombinant viruses carrying modified viral DNA or RNA that has been rendered noninfectious, but that still contain viral promoters and also the transgene, thus allowing for translation of the transgene through a viral promoter. Viral vectors are often designed for permanent incorporation of the insert into the host genome, and thus leave distinct genetic markers in the host genome after incorporating the transgene. A viral vector can be recombinantly made to be of a size that it can be encapsulated in a lipid nanoparticle of the invention.

An "RNAi agent" is a composition or compound capable of mediating RNA interference. The term "RNA interference" (RNAi) is a post-transcriptional, targeted gene-silencing technique that uses a RNAi agent to degrade messenger RNA (mRNA) containing a sequence which is the same as or very similar to the RNAi agent. See: Zamore and Haley 2005 Science 309: 1519-1524; Zamore et al. 2000 Cell 101: 25-33; Elbashir et al. 2001 Nature 411: 494-498; and Kreutzer et al., PCT Publication WO 00/44895; Fire, PCT Publication WO 99/32619; Mello and Fire, PCT Publication WO 01/29058; and the like.

As used herein, RNAi is equivalent to other terms used to describe sequence specific RNA interference, such as post transcriptional gene silencing, translational inhibition, transcriptional inhibition, or epigenetics. For example, the formulations containing lipids of the invention can be used in conjunction with siNA molecules to epigenetically silence genes at both the post-transcriptional level and/or the pre-transcriptional level. In a non-limiting example, modulation of gene expression by siNA molecules can result from siNA mediated cleavage of RNA (either coding or non-coding RNA) via RISC, or alternately, translational inhibition as is known in the art. In another embodiment, modulation of gene expression by siNA can result from transcriptional inhibition such as is reported e.g., in Janowski et al. 2005 Nature Chemical Biology 1: 216-222.

RNAi agents include, inter alia, siRNA or siNA, micro-RNA (miRNA), shRNA, short interfering oligonucleotide and chemically-modified short interfering nucleic acid molecules. The terms "short interfering RNA" (siRNA) or "short interfering nucleic acid" (siNA), or the like, as used herein, refer to any molecule capable of inhibiting or down regulating gene expression or viral replication by mediating RNA interference (RNAi) or gene silencing in a sequence-specific manner. siRNAs can be generated by ribonuclease III cleavage from longer double-stranded RNA (dsRNA) which are homologous to, or specific to, the silenced gene target. They can also be made artificially by various methods known in the art.

RNAi agents of the present disclosure can target any target gene and comprise any sequence, and can have any of several formats, components, substitutions and/or modifications.

RNAi agent generally comprise two strands, an anti-sense (or guide) strand and a sense (or passenger) strand; the anti-sense strand is incorporated into the RISC (RNA interference silencing complex) and targets the corresponding sequence of a target mRNA. The sequence (or a portion thereof) of the anti-sense strand matches that of the target mRNA. A few mismatches (generally no more than 1-3 per 15 nt sequence) can be present without preventing target-specific RNAi activity. The anti-sense and sense strand can be separate molecules, or connected by a linker or loop (to form, e.g., a shRNA). The anti-sense strand is generally a 49-mer or shorter, often a 19-mer to 25-mer. The sense strand can be the same length as, or shorter or longer than the anti-sense strand. As shown herein, the anti-sense strand can be as short as a 18-mer, and the sense strand can be as short as a 14-mer.

The canonical siRNA is two strands of RNA, each a 21-mer, with a 19-bp (basepair) double-stranded region and two 2-nt (nucleotide) overhangs. Elbashir et al. 2001 Nature 411: 494-498; Elbashir et al. 2001 EMBO J. 20: 6877-6888. The overhangs can be replaced by a dinucleotide such as dTdT, TT, UU, U (2'-OMe) dT, U (2'-OMe) U (2'-OMe), T(2'-OMe) T (2'-OMe), T(2'-OMe) dT, or the like. The overhang acts to protect the RNAi agent from cleavage by nucleases, while not interfering with RNAi activity or contributing to target recognition. Elbashir et al. 2001 Nature 411: 494-498; Elbashir et al. 2001 EMBO J. 20: 6877-6888; and Kraynack et al. 2006 RNA 12:163-176. Additional 3'-terminal nucleotide overhangs include dT (deoxythimidine), 2'-0,4'-C-ethylene thymidine (eT), and 2-hydroxyethyl phosphate (hp). 4-thiouracil and 5-bromouracil substitutions can also be made. Parrish et al. 2000 Molecular Cell 6: 1077-1087. Nucleotidic overhangs can be replaced by non-nucleotidic 3' end caps, provided that such caps are capable of protecting the ends from cleavage, and allowing RNAi activity of the molecule. See, for example, U.S. Pat. Nos. 8,097,716; 8,084,600; 8,404,831; 8,404,832; and 8,344,128; and U.S. Pat. App. No. 61/886,739, which is incorporated entirely by reference.

In either strand, one or more positions can be replaced by a spacer. These include, without limitation, a sugar, alkyl, cycloakyl, ribitol or other type of abasic nucleotide, 2'-deoxy-ribitol, diribitol, 2'-methoxyethoxy-ribitol (ribitol with 2'-MOE), $C_{3-6}$ alkyl, or 4-methoxybutane-1,3-diol (5300). In some molecules, a gap can be introduced into the sense strand, producing two shorter sense strands; this is called a sisiRNA. WO 2007/107162 to Wengels and Kjems. One or more mismatches and bulges between the sense and anti-sense strand can also be introduced. U.S. Patent App. No. 2009/0209626 to Khvorova.

RNAi agents can be constructed from RNA, as in the canonical siRNA. However, RNA nucleotides can be substituted or modified in various RNAi agents. At one or more positions, a RNA nucleotide can be replaced by DNA, a peptide nucleic acid (PNA), locked nucleic acid (LNA), morpholino nucleotide, threose nucleic acid (TNA), glycol nucleic acid (GNA), arabinose nucleic acid (ANA), 2"-fluoroarabinose nucleic acid (FANA), cyclohexene nucleic acid (CeNA), anhydrohexitol nucleic acid (HNA), or unlocked nucleic acid (UNA). Particularly in the seed region (approximately positions 2-7 of the anti-sense strand and the corresponding positions of the sense strand), the nucleotides in one or both strand can be replaced by DNA. The entire seed region can be replaced by DNA, forming a DNA-RNA hybrid capable of mediating RNA interference. Yamato et al. 2011. Cancer Gene Ther. 18: 587-597.

RNA nucleotides can be either substituted with other components (as described above) and/or modified. Modifications and/or substitutions can be made at the sugar, phosphate and/or base. In various aspects, the RNAi agent comprises a 2'-modification of the sugar, for example, 2'-amino, 2'-C-allyl, 2'-deoxy, 2'-deoxy-2'-fluoro (2'-F), 2'-O-methyl (2'-OMe), 2'-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA); other RNA modifications are known in the art. See, for example, Usman and Cedergren 1992 TIBS. 17: 34; Usman et al. 1994 Nucleic Acids Symp. Ser. 31: 163; Burgin et al. 1996 Biochemistry 35: 14090. In some embodiments, the two RNA nucleotides on the 3' end of either or both strands are modified with a 2'-MOE, forming a 2'-MOE clamp. U.S. Pat. Nos. 8,097, 716; and 8,084,600.

One or more phosphate of the sugar-phosphate backbone can be replaced, e.g., by a modified internucleoside linker. This can include, without limitation, phosphorothioate, phosphorodithioate, phosphoramidate, boranophosphonoate, an amide linker, and a compound of formula (Ia):

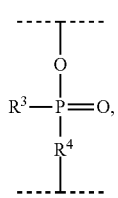

(Ia)

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

The base can also be modified or substituted, e.g., with 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. In certain aspects, the RNAi agent can comprise a non-natural nucleobase, wherein the non-natural nucleobase is difluorotolyl, nitroindolyl, nitropyrrolyl, or nitroimidazolyl. Many other modifications are known in the art. See, for example, Usman et al. 1992 TIBS 17:34; Usman et al. 1994 Nucl. Acids Symp. Ser. 31: 163; Burgin et al. 1996 Biochem. 35: 14090.

For example, one or more position can be represented by 2'-O-methylcytidine-5'-phosphate, 2'-O-methyluridine-5'-phosphate. In short, any one or more position can be represented by any modification or substitution known in the art, including, without limitation, 2'-O-methyl modified nucleotide, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, an unlocked ribonucleotide (e.g., an acyclic nucleotide monomer, as described in WO 2008/147824), a phosphoramidate or a non-natural base comprising nucleoside, or any combination thereof.

Any of these various formats, components, substitutions and/or modifications can be mixed and matched or combined in different ways to form RNAi agents to any target and comprising any sequence. For example, the present disclosure pertains to an RNAi agent which comprises two strands, wherein one or both strands is an 18-mer which terminates at the 3' end in a phosphate or modified internucleoside linker, and further comprises, in 5' to 3' order, a spacer, a second phosphate or modified internucleoside linker, and a 3' end cap. In another embodiment, the present disclosure pertains to an RNAi agent which comprises a sense and anti-sense strand, wherein the anti-sense strand comprises, in 5- to 3-order, an 18-mer which terminates at the 3' end in a phosphate or modified internucleoside linker, and further comprises, in 5' to 3' order, a spacer, a second phosphate or modified internucleoside linker, and 3' end cap; and wherein the sense strand comprises, in 5' to 3' order, a 14-mer (or longer) which terminates at the 3' end in a phosphate or modified internucleoside linker, and further comprises, in 5' to 3' order, a spacer, a second phosphate or modified internucleoside linker, and 3' end cap.

In various embodiments of the present disclosure, the RNAi agent can target any target gene and have any sequence and can have any format, component, substitution and/or modification as described herein or known in the art.

The term "RNAi inhibitor" is any molecule that can down modulate (e.g. reduce or inhibit) RNA interference function or activity in a cell or patient. An RNAi inhibitor can down regulate, reduce or inhibit RNAi (e.g. RNAi mediated cleavage of a target polynucleotide, translational inhibition, or transcriptional silencing) by interaction with or interfering with the function of any component of the RNAi pathway, including protein components such as RISC, or nucleic acid components such as miRNAs or siRNAs. An RNAi inhibitor can be a siNA molecule, an antisense molecule, an aptamer, or a small molecule that interacts with or interferes with the function of RISC, a miRNA, or a siRNA or any other component of the RNAi pathway in a cell or patient. By inhibiting RNAi (e.g. RNAi mediated cleavage of a target polynucleotide, translational inhibition, or transcriptional silencing), an RNAi inhibitor can be used to modulate (e.g, up-regulate or down-regulate) the expression of a target gene. In one embodiment, an RNA inhibitor is used to up-regulate gene expression by interfering with (e.g. reducing or preventing) endogenous down-regulation or inhibition of gene expression through translational inhibition, transcriptional silencing, or RISC mediated cleavage of a polynucleotide (e.g. mRNA). By interfering with mechanisms of endogenous repression, silencing, or inhibition of gene expression, RNAi inhibitors of the invention can therefore be used to up-regulate gene expression for the treatment of diseases or conditions resulting from a loss of function. The term "RNAi inhibitor" is used interchangeably with the term "siNA" in various embodiments herein.

The term "enzymatic nucleic acid" as used herein refers to a nucleic acid molecule that has complementarity in a substrate binding region to a specified gene target, and also has an enzymatic activity that acts to specifically cleave a target RNA, thereby inactivating the target RNA molecule. The complementary regions allow sufficient hybridization of the enzymatic nucleic acid molecule to the target RNA and thus permit cleavage. Complementarity of 100% is preferred, but complementarity as low as 50-75% can also be useful in this invention (see e.g., Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The key features of an enzymatic nucleic acid molecule are that it has a specific substrate binding site that is complementary to one or more of the target nucleic acid regions, and that it has nucleotide sequences within or surrounding that substrate binding site that impart a nucleic acid cleaving and/or ligation activity to the molecule (see, e.g., Cech et al., U.S. Pat. No. 4,987,071; Cech et al., 1988, 260 JAMA 3030). Ribozymes and enzymatic nucleic acid molecules of the invention can be chemically modified, e.g., as described in the art and elsewhere herein.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Antisense DNA can be synthesized chemically or expressed via the use of a single stranded DNA expression vector or equivalent thereof. Antisense molecules of the invention can be chemically modified, e.g. as described in the art.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see e.g., Arrow et al., U.S. Pat. No. 5,849,902; Arrow et al., U.S. Pat. No. 5,989,912). The RNase H enzyme binds to the nucleic acid molecule-target RNA complex and cleaves the target RNA sequence.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease that, in turn, cleaves the target RNA (Torrence et al., 1993 Proc. Natl. Acad. Sci. USA 90, 1300; Silverman et al., 2000, Methods Enzymol., 313, 522-533; Player and Torrence, 1998, Pharmacol. Ther., 78, 55-113). 2-5A antisense chimera molecules can be chemically modified, e.g. as described in the art.

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206). Triplex forming oligonucleotide molecules of the invention can be chemically modified, e.g. as described in the art.

The term "decoy RNA" as used herein, refers to an RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. Similarly, a decoy RNA can be designed to bind to a receptor and block the binding of an effector molecule, or can be designed to bind to receptor of interest and prevent interaction with the receptor. Decoy molecules of the invention can be chemically modified, e.g. as described in the art.

The term "single stranded DNA" (ssDNA) as used herein refers to a naturally occurring or synthetic deoxyribonucleic acid molecule comprising a linear single strand, e.g., a ssDNA can be a sense or antisense gene sequence or EST (Expressed Sequence Tag).

The term "allozyme" as used herein refers to an allosteric enzymatic nucleic acid molecule, including e.g., U.S. Pat. Nos. 5,834,186, 5,741,679, 5,589,332, 5,871,914, and PCT publication Nos. WO 00/24931, WO 00/26226, WO 98/27104, and WO 99/29842.

The term "aptamer" as used herein is meant a polynucleotide composition that binds specifically to a target molecule, wherein the polynucleotide has a sequence that differs from a sequence normally recognized by the target molecule in a cell. Alternately, an aptamer can be a nucleic acid molecule that binds to a target molecule where the target molecule does not naturally bind to a nucleic acid. The target molecule can be any molecule of interest. Aptamer molecules of the invention can be chemically modified, e.g. as described in the art.

3.0 Lipids

3.1 Cationic Lipids

Cationic lipids suitable for use in the lipid composition include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)N,N,N-trimethylammonium chloride (DOTAP), N-(1-(2,3dioleyloxy)propyl)-N,N,N-trimethylammonium chloride (DOTMA), N,N-dimethyl-2,3-dioleyloxy)propylamine (DODMA), 1,2-Dioleoyl-3-Dimethylammoniumpropane (DODAP), 1,2-Dioleoylcarbamyl-3-Dimethylammoniumpropane (DOCDAP), 1,2-Dilineoyl-3-Dimethylammoniumpropane (DLINDAP), Dioleoyloxy-N-[2-spenninecarboxamido)ethyl}-N,N-dimethyl-lpropanaminiumtrifluoroacetate (DOSPA), Dioctadecylamidoglycyl spennine (DOGS), DC-Chol, 1,2Dimyristyloxypropyl-3-dimethyl-hydroxyethyl ammonium bromide (DMRIE), 3-Dimethylamino-2-(Cholest-5-en-3beta-oxybutan-4-oxy)-1-(cis,cis-9,12-octadecadienoxy) propane (CLinDMA), 2-[5'-(cholest-5-en-3~-oxy)-3'-oxapentoxy)-3-dimethyl-1-(cis,cis-9',12'-octadecadienoxy) propane (CpLinDMA), N,N-Dimethyl-3,4-dioleyloxybenzylamine (DMOBA), 1,2-N,N'-Dioleylcarbamyl-3-dimethylaminopropane (DOcarbDAP), and/or mixtures thereof.

Other suitable cationic lipids are disclosed in U.S. Provisional App. Ser. No. 61/918,927 which is incorporated by reference herein in its entirety. A suitable lipid is a compound, or salt thereof, of formula (I):

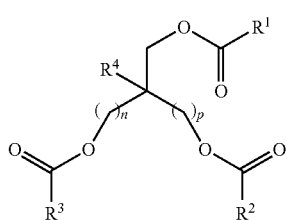
(I)

wherein n and p are each, independently, 1 or 2; $R^1$ is heterocyclyl, heterocyclyl-$C_{1-8}$-alkyl or heterocyclyl-$C_{1-8}$-alkoxyl, each of which may be optionally substituted with 1, 2 or 3 groups, independently selected from $C_{1-8}$-alkyl, $C_{3-7}$-cycloalkyl, $C_{3-7}$-cycloalkyl-$C_{1-8}$-alkyl, heterocyclyl, —[($C_1$-$C_4$)alkylene]$_v$-N(R')R", —O[($C_1$-$C_4$)alkylene]$_v$—N(R')R" or —N(H)—[($C_1$-$C_4$)alkylene]$_v$—N(R')R", where said ($C_1$-$C_4$)alkylene is optionally substituted with one or more R groups; v is 0, 1, 2, 3 or 4; R is hydrogen or —$C_{1-8}$-alkyl or when v is 0, R is absent; R' and R", are each, independently, hydrogen, —$C_{1-8}$-alkyl; or R' and R" combine with the nitrogen to which they are bound, and optionally including another heteroatom selected from N, O and S, to form a 5-8 membered heterocycle or heteroaryl, optionally substituted with an —$C_{1-8}$-alkyl, hydroxy or cycloalkyl-$C_{1-8}$—; $R^2$ and $R^3$ are each, independently, $C_{12-22}$ alkyl, $C_{12-22}$ alkenyl,

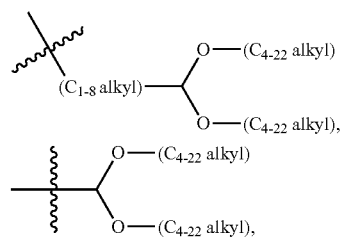

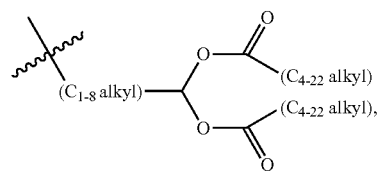

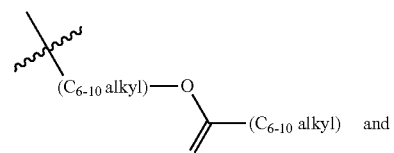

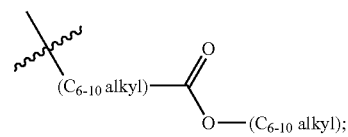

$R^4$ is selected from hydrogen, $C_{1-14}$ alkyl,

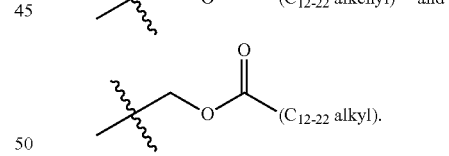

Other cationic lipids include a compound, or salt thereof, according to formula (II):

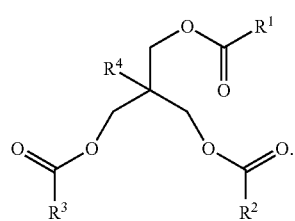
(II)

Other suitable cationic lipids include those of formulas (I) and (II) wherein R4 is hydrogen or where R4 is
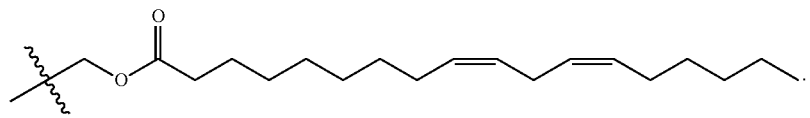 [SMILES: *COC(=O)CCCCCCC/C=C\C/C=C\CCCCC]
Other suitable cationic lipids include the foregoing lipids where $R^1$ is selected from:
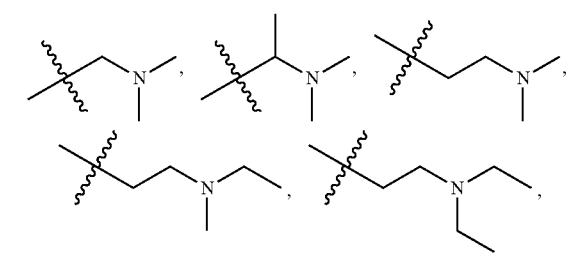
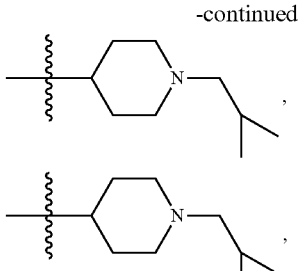
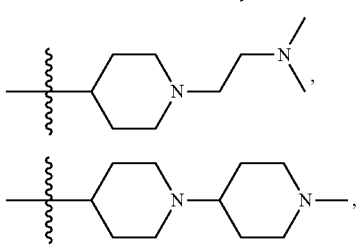
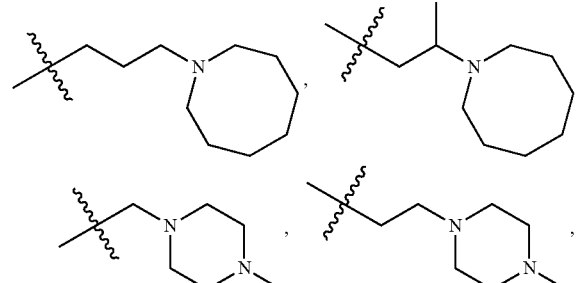
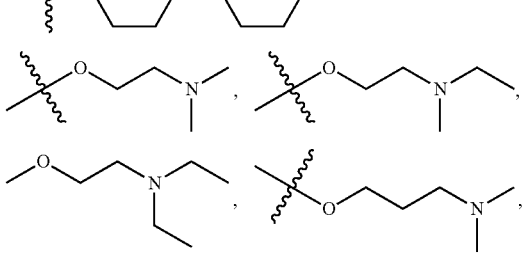
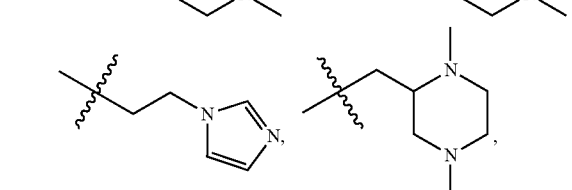
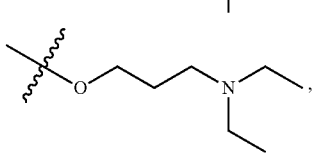
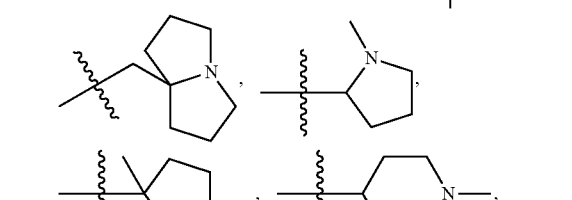
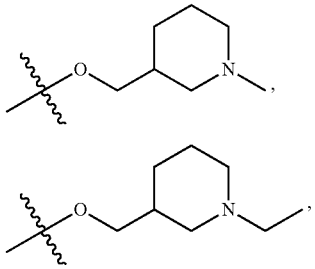
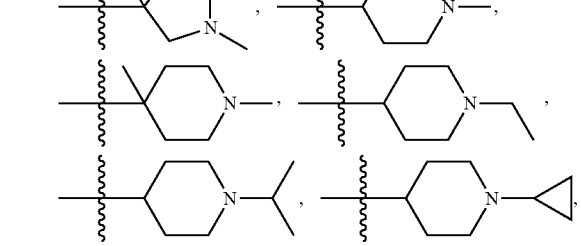
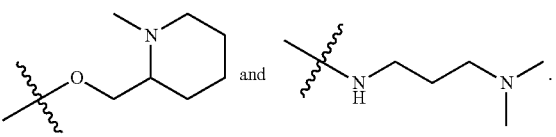

Other suitable cationic lipids include the foregoing lipids wherein $R^2$ is selected from:

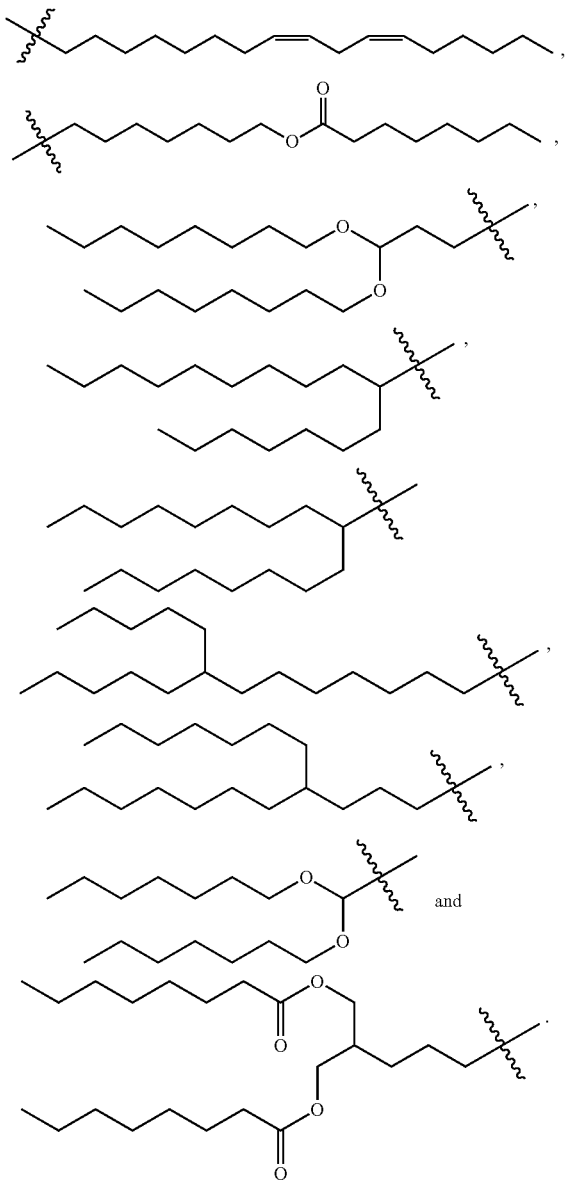

Other suitable cationic lipids include the foregoing lipids where $R^3$ is selected from

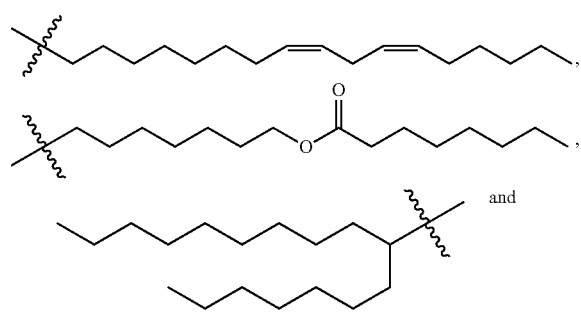

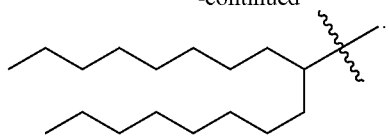

Other suitable lipids according to the foregoing lipids include those where $R^2$ and $R^3$ are identical.

Specific cationic lipids include a compound is selected from the group consisting of:
(9Z,9'Z,12Z,12'Z)-2-(((1,3-dimethylpyrrolidine-3-carbonyl)oxy)methyl)propane-1,3-diyl bis(octadeca-9,12-dienoate;
(9Z,9'Z,12Z,12'Z)-2-(((3-(4-methylpiperazin-1-yl)propanoyl)oxy)methyl)propane-1,3-diyl bis(octadeca-9,12-dienoate);
(9Z,9'Z,12Z,12'Z)-2-(((4-(pyrrolidin-1-yl)butanoyl)oxy)methyl)propane-1,3-diyl bis(octadeca-9,12-dienoate);
(9Z,9'Z,12Z,12'Z)-2-(((4-(piperidin-1-yl)butanoyl)oxy)methyl)propane-1,3-diylbis(octadeca-9,12-dienoate);
(9Z,9'Z,12Z,12'Z)-2-(((3-(dimethylamino)propanoyl)oxy)methyl)propane-1,3-diyl bis(octadeca-9,12-dienoate);
(9Z,9'Z,12Z,12'Z)-2-((2-(dimethylamino)acetoxy)methyl) propane-1,3-diyl bis(octadeca-9,12-dienoate);
(9Z,9'Z,12Z,12'Z)-2-(((3-(diethylamino)propanoyl)oxy)methyl) propane-1,3-diyl bis(octadeca-9,12-dienoate);
(9Z,9'Z,12Z,12'Z)-2-(((1,4-dimethylpiperidine-4-carbonyl)oxy)methyl)propane-1,3-diyl bis(octadeca-9,12-dienoate);
(9Z,9'Z,12Z,12'Z)-2-(((1-(cyclopropylmethyl)piperidine-4-carbonyl)oxy)methyl)propane-1,3-diyl bis(octadeca-9,12-dienoate);
(9Z,9'Z,12Z,12'Z)-2-(((3-morpholinopropanoyl)oxy)methyl)propane-1,3-diylbis(octadeca-9,12-dienoate);
(9Z,9'Z,12Z,12'Z)-2-(((4-(dimethylamino)butanoyl)oxy)methyl)propane-1,3-diyl bis(octadeca-9,12-dienoate);
2-(((1,3-dimethylpyrrolidine-3-carbonyl)oxy)methyl)propane-1,3-diyl bis(8-(octanoyloxy)octanoate);
(9Z,12Z)-3-((4,4-bis(octyloxy)butanoyl)oxy)-2-((((3-(diethylamino)propoxy)carbonyl)oxy)methyl)propyl octadeca-9,12-dienoate;
(9Z,12Z)-3-((4,4-bis(octyloxy)butanoyl)oxy)-2-((((3-(dimethylamino)propoxy)carbonyl)oxy)methyl)propyl octadeca-9,12-dienoate;
(9Z,12Z)-3-((4,4-bis(octyloxy)butanoyl)oxy)-2-(((((1-ethylpiperidin-3-yl)methoxy)carbonyl)oxy)methyl)propyl octadeca-9,12-dienoate;
2-((((2-(diethylamino)ethoxy)carbonyl)oxy)methyl)propane-1,3-diyl bis(2-heptylundecanoate);
(9Z,12Z)-3-(((2-(diethylamino)ethoxy)carbonyl)oxy)-2-(((2-heptylundecanoyl)oxy)methyl)propyl octadeca-9,12-dienoate;
2-((((3-(dimethylamino)propoxy)carbonyl)oxy)methyl)propane-1,3-diyl bis(2-heptylundecanoate);
(9Z,12Z)-3-(((3-(diethylamino)propoxy)carbonyl)oxy)-2-(((2-heptylundecanoyl)oxy)methyl)propyl octadeca-9,12-dienoate;
(9Z,12Z)-3-(((2-(dimethylamino)ethoxy)carbonyl)oxy)-2-(((3-octylundecanoyl)oxy)methyl)propyl octadeca-9,12-dienoate;
2-((((3-(diethylamino)propoxy)carbonyl)oxy)methyl)propane-1,3-diyl bis(3-octylundecanoate);
(9Z,12Z)-3-(((3-(diethylamino)propoxy)carbonyl)oxy)-2-(((3-octylundecanoyl)oxy)methyl)propyl octadeca-9,12-dienoate;

(9Z,12Z)-3-(((3-(diethylamino)propoxy)carbonyl)oxy)-2-(((9-pentyltetradecanoyl)oxy)methyl)propyl octadeca-9,12-dienoate;

(9Z,12Z)-3-(((3-(diethylamino)propoxy)carbonyl)oxy)-2-(((5-heptyldodecanoyl)oxy)methyl)propyl octadeca-9,12-dienoate;

(9Z,12Z)-3-(2,2-bis(heptyloxy)acetoxy)-2-((((2-(dimethylamino)ethoxy)carbonyl)oxy)methyl)propyl octadeca-9,12-dienoate; and (9Z,12Z)-3-((6,6-bis(octyloxy)hexanoyl)oxy)-2-((((3-(diethylamino)propoxy)carbonyl)oxy)methyl)propyl octadeca-9,12-dienoat.

Other suitable cationic lipids are disclosed in U.S. Provisional App. Ser. No. 61/918,941 which is incorporated by reference herein in its entirety. A suitable lipid is a compound, or salt thereof, of formula (III):

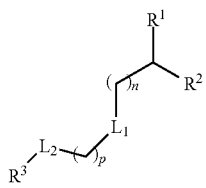

Wherein n is 0, 1, 2, 3 or 4; p is 0, 1, 2, 3, 4, 5, 6, 7 or 8; $L_1$ is —O— or a bond; $L_2$ is —OC(O)— or —C(O)O—; $R^1$ is selected from:

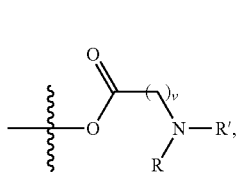 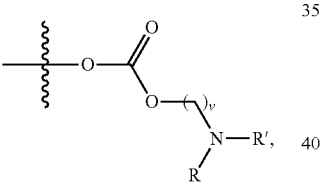

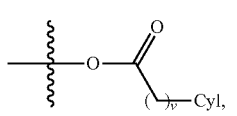 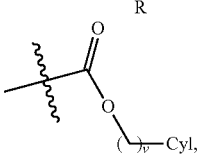

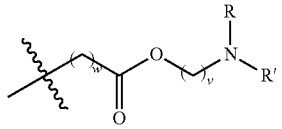

and

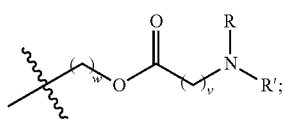

v is 0, 1, 2, 3 or 4; w is 0, 1, 2, or 3; Cy1 is 5-7 membered nitrogen containing heterocycle optionally substituted with one or two alkyl groups; R and R' are each, independently, hydrogen or $C_{1-8}$ alkyl; and $R^2$ is selected from $C_{6-20}$ alkyl optionally substituted with a hydroxyl, $C_{15-19}$ alkenyl, $C_{1-12}$alkyl-OC(O)—$C_{5-20}$alkyl, $C_{1-12}$alkyl-C(O)O—$C_{5-20}$alkyl and

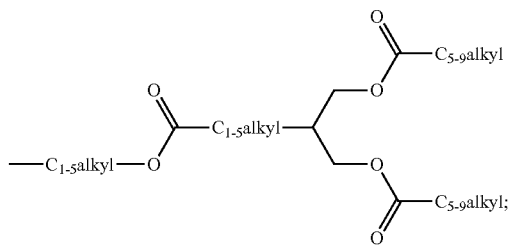

$R^3$ is selected from: $C_{4-22}$ alkyl, $C_{12-22}$ alkenyl,

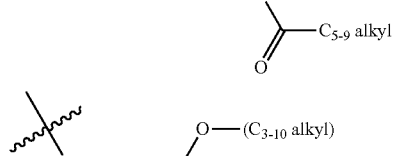

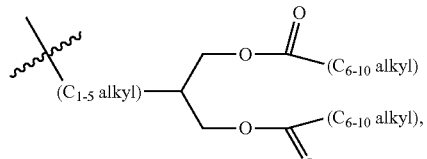

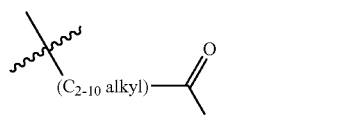

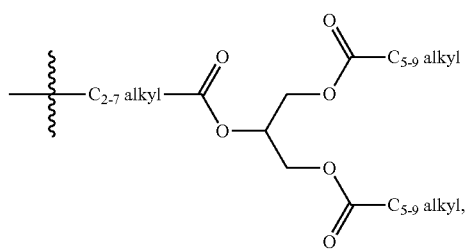

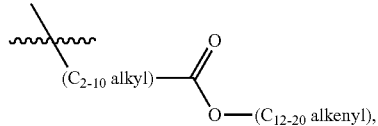

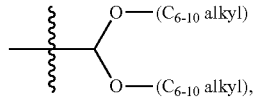

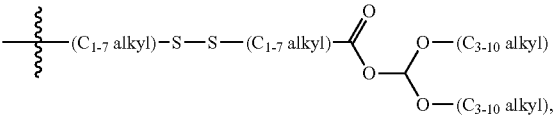

-continued
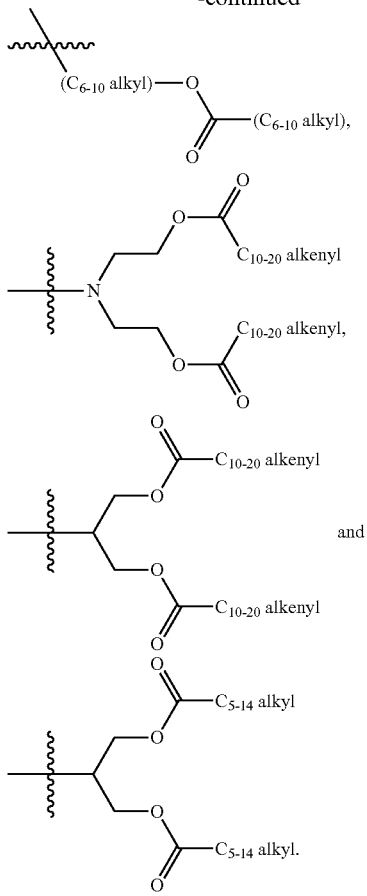
Other suitable cationic lipids include those of formula (IV), or salt thereof:
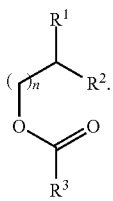
Other suitable cationic lipids include those of formula (V):
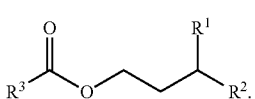
Other suitable cationic lipids include those of formulas (III) to (V), wherein $R^2$ is selected from:
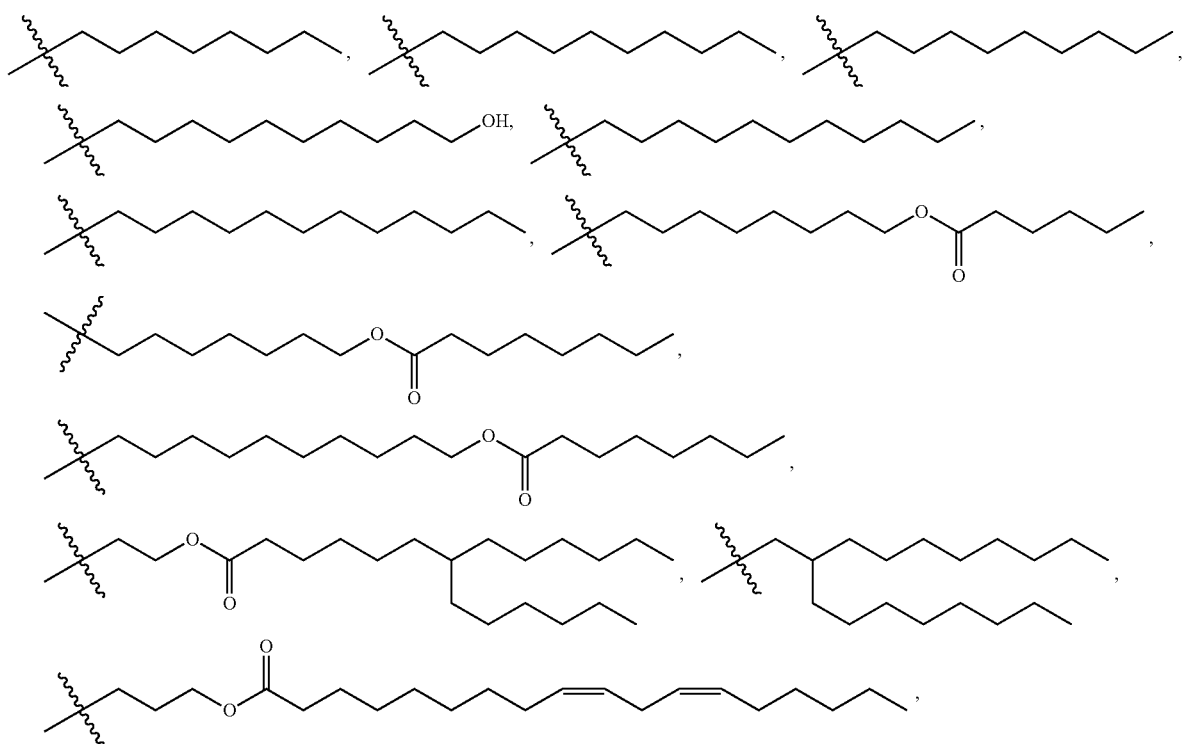

-continued
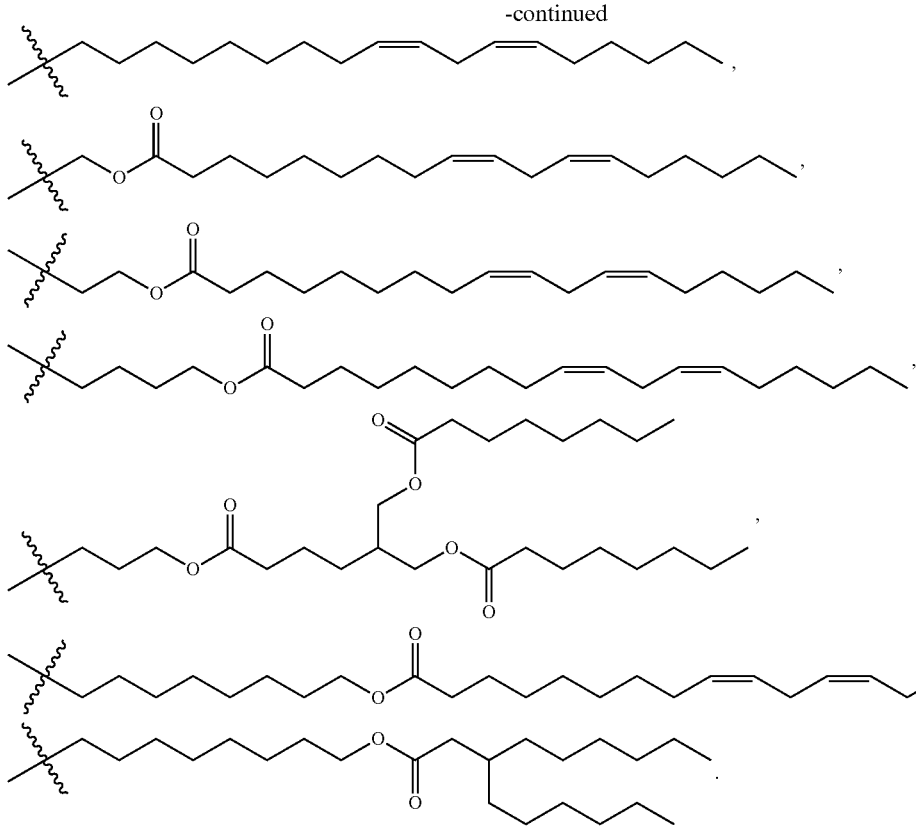
Other suitable cationic lipids include those of formulas (III) to (V), wherein R² is:
Other suitable cationic lipids include those of formulas (III) to (V), wherein the compound is of formula (VI):
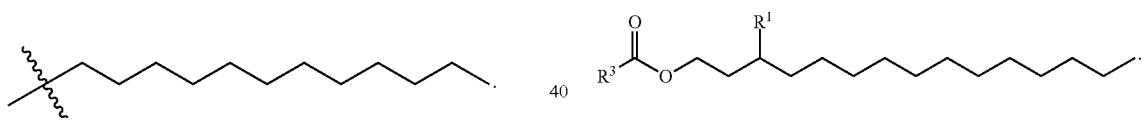
Other suitable cationic lipids include those of formulas (III) to (VI), wherein R³ is selected from:
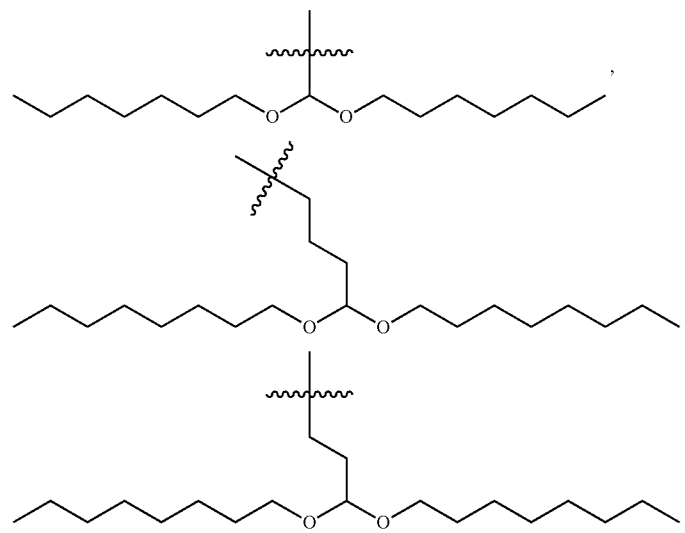

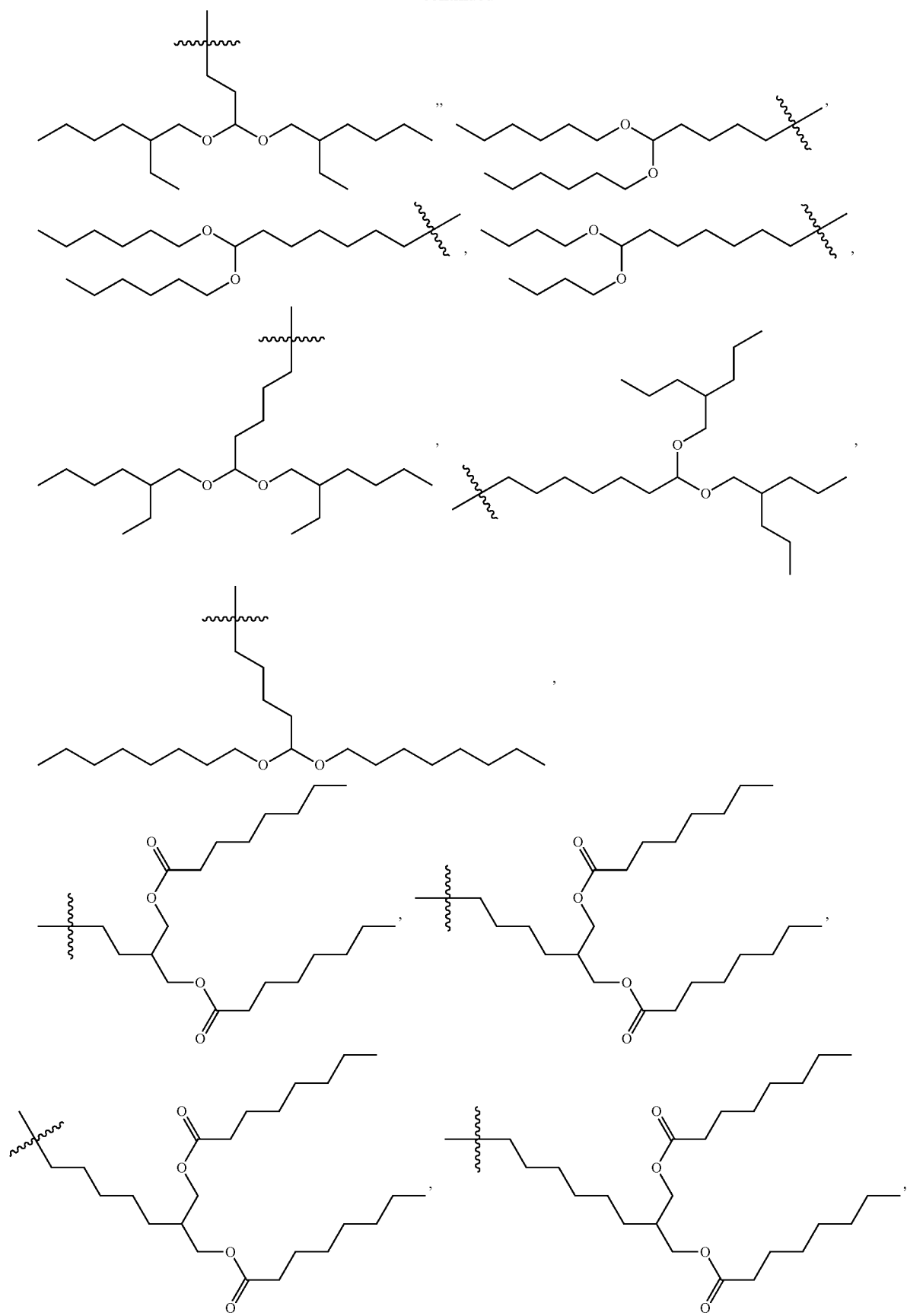

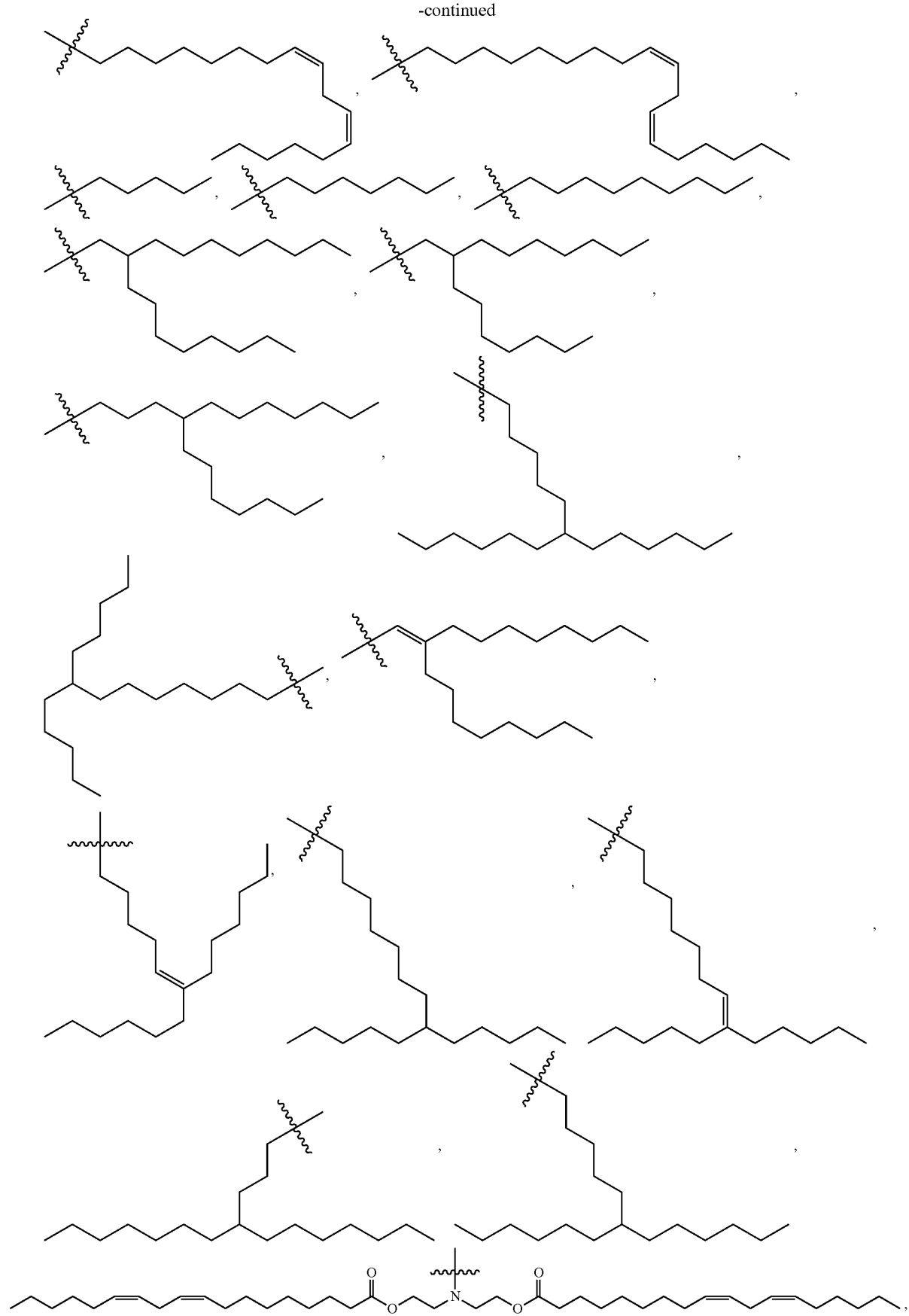

-continued
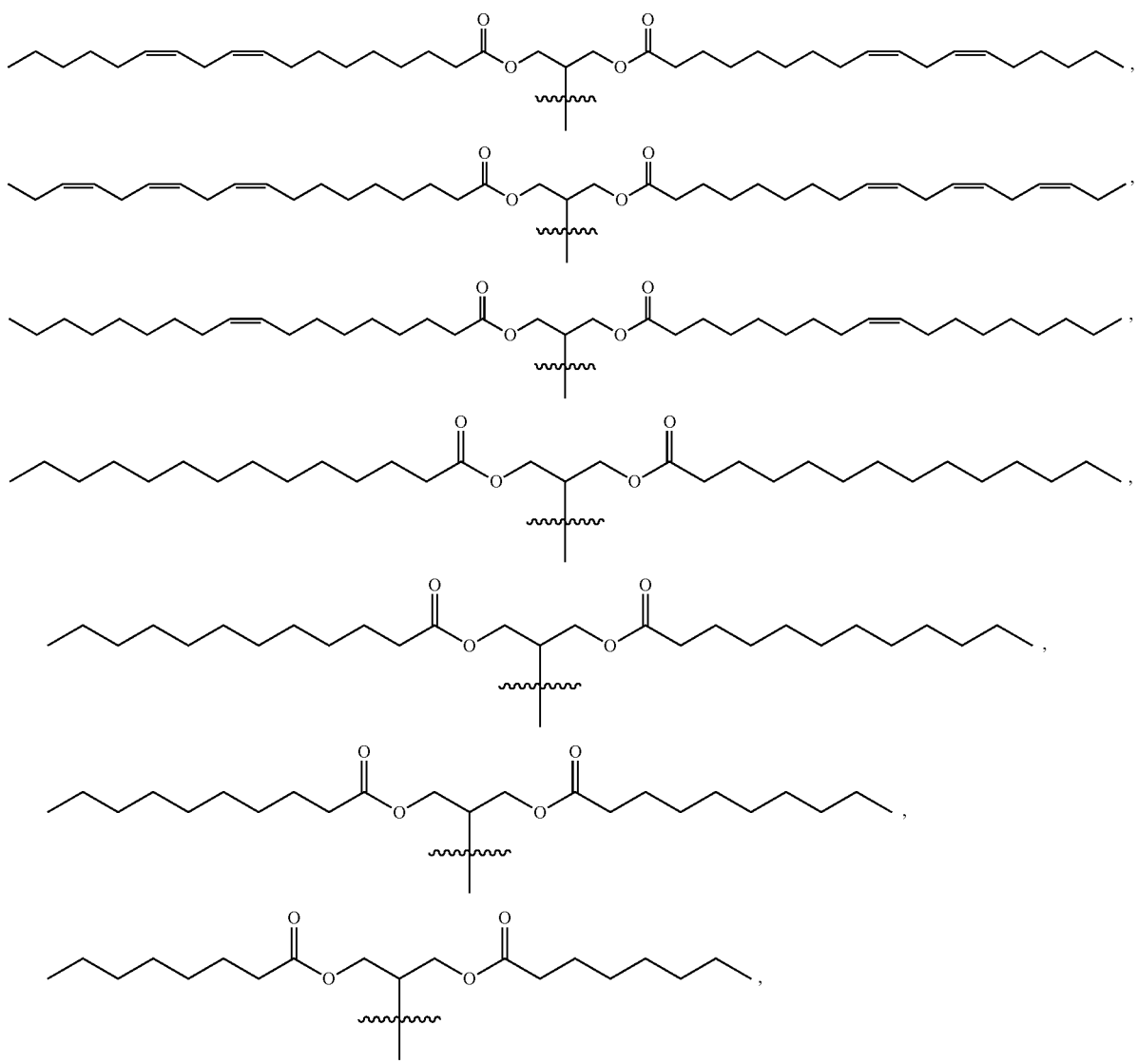
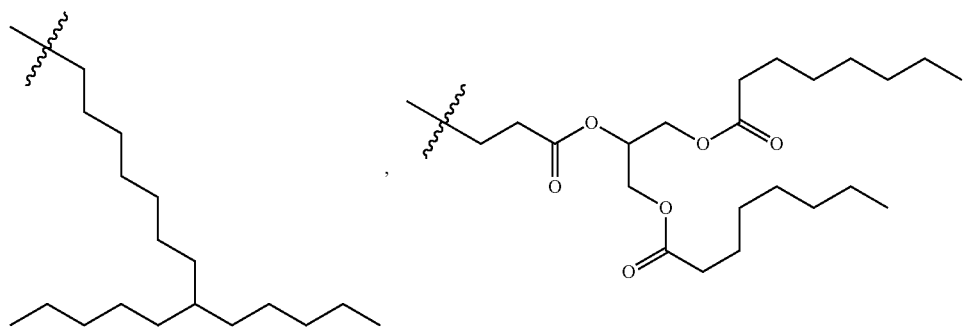
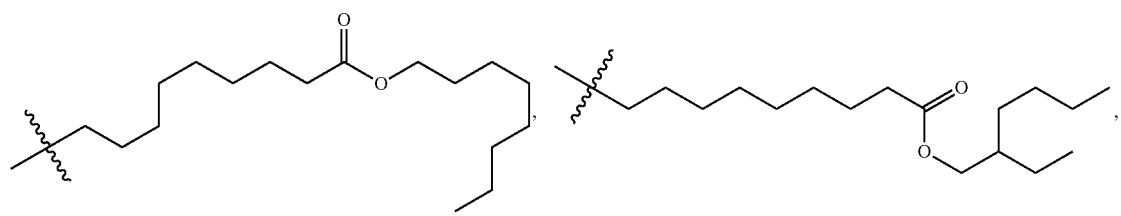

31
32
-continued
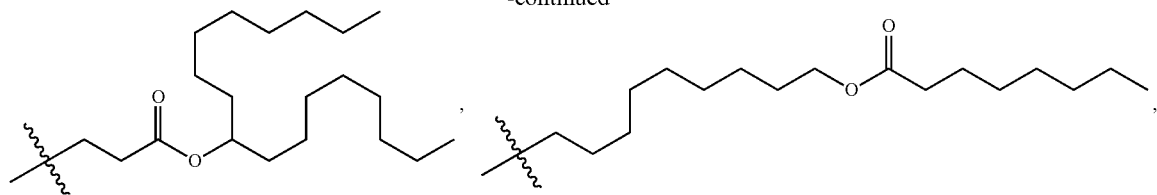
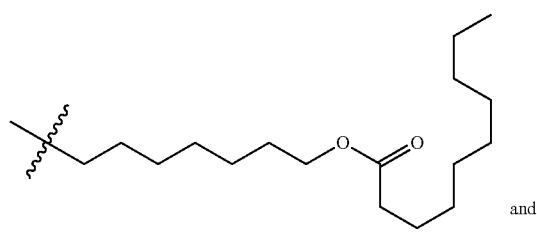
and
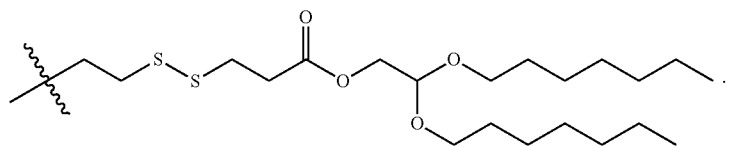
Other suitable cationic lipids include those of formulas (III) to (VI), wherein $R^3$ is
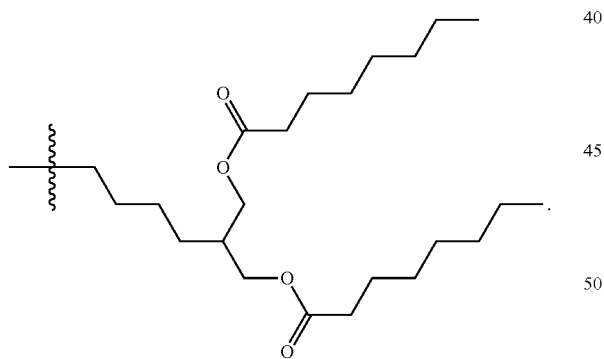
Other suitable cationic lipids include those of formulas (III) to (VI), wherein $R^3$ is
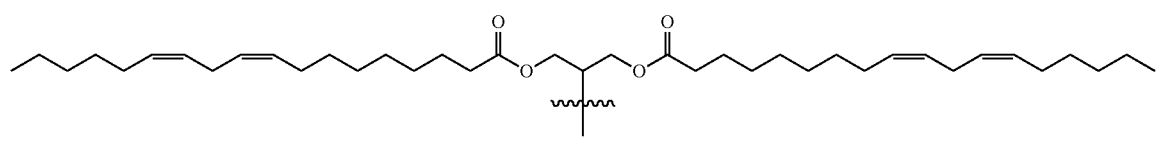 [SMILES: *C(COC(=O)CCCCCCC/C=C\C/C=C\CCCCC)COC(=O)CCCCCCC/C=C\C/C=C\CCCCC]

Other suitable cationic lipids include those of formulas (III) to (VI), wherein the compound is of formula (VII):

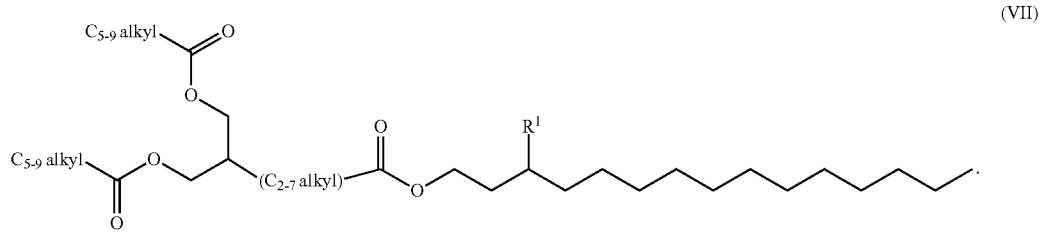

Other suitable cationic lipids include those of formulas (III) to (VII), wherein the compound is of formula (VIII):

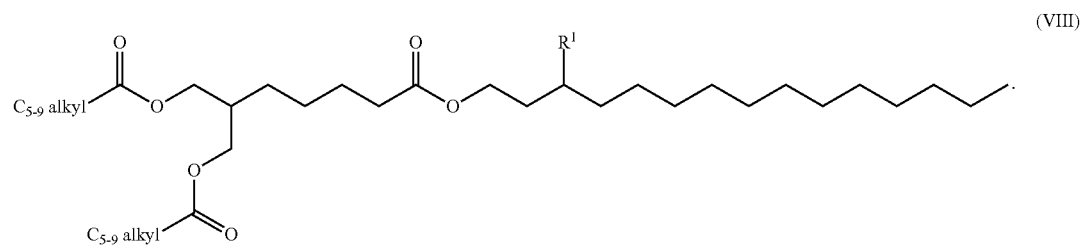

Other suitable cationic lipids include those of formulas (III) to (VIII), wherein the compound is of formula (IX):

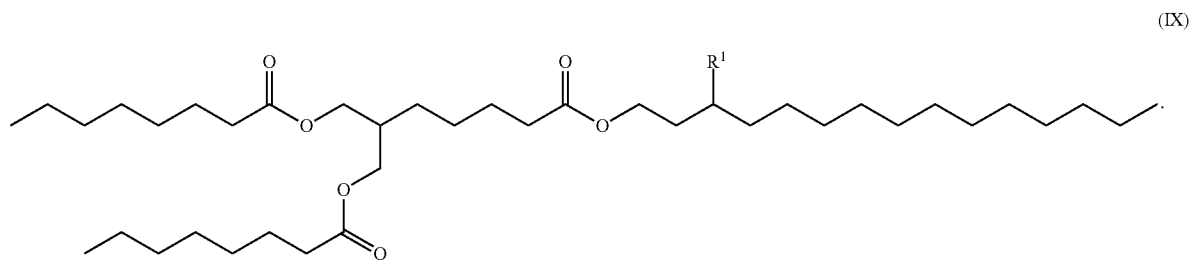

Other suitable cationic lipids include those of formulas (III) to (IX), wherein $R^1$ is selected from:

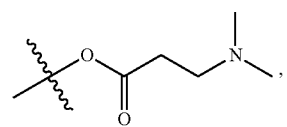

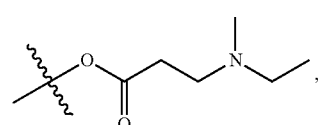

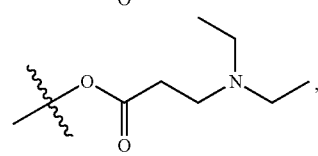

-continued

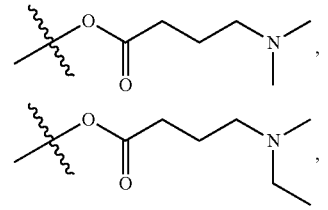

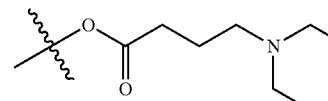

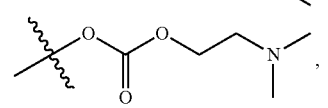

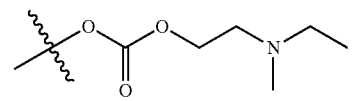

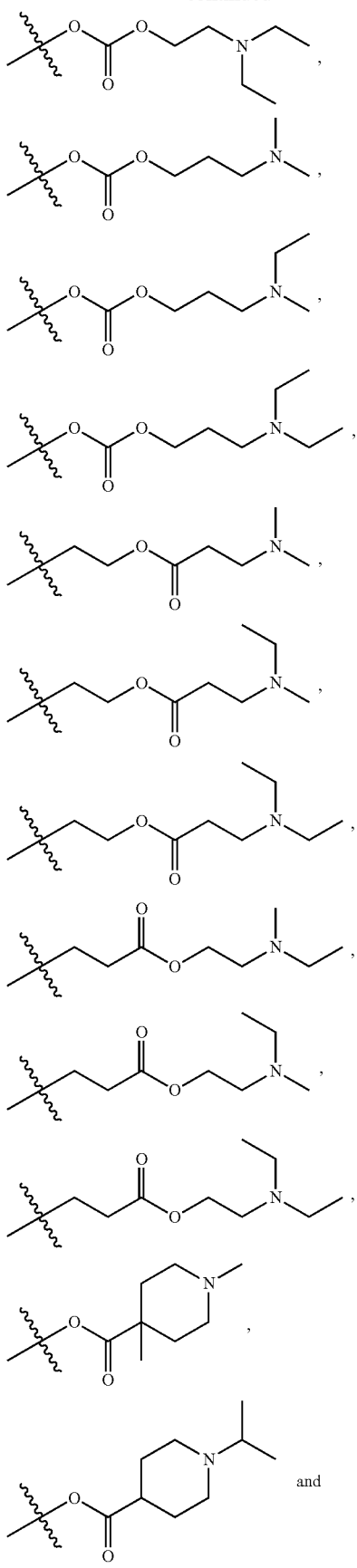

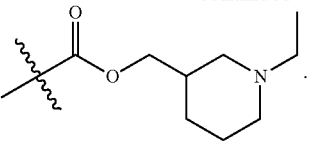

Other suitable cationic lipids include those of formulas (III) to (IX), wherein $R^1$ is

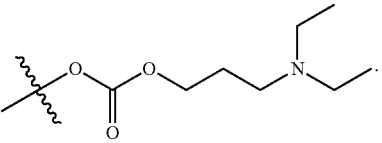 [SMILES: *OC(=O)OCCCN(CC)CC]

Other suitable cationic lipids include those of formulas (III) to (IX), wherein $R^1$ is

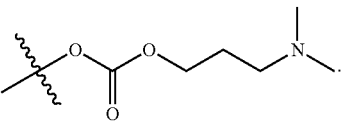 [SMILES: *OC(=O)OCCCN(C)C]

Other suitable cationic lipids are selected from:
2-(10-dodecyl-3-ethyl-8,14-dioxo-7,9,13-trioxa-3-azaoctadecan-18-yl)propane-1,3-diyl dioctanoate;
2-(9-dodecyl-2-methyl-7,13-dioxo-6,8,12-trioxa-2-azaheptadecan-17-yl)propane-1,3-diyl dioctanoate;
2-(9-dodecyl-2-methyl-7,13-dioxo-6,8,12-trioxa-2-azapentadecan-15-yl)propane-1,3-diyl dioctanoate;
2-(10-dodecyl-3-ethyl-8,14-dioxo-7,9,13-trioxa-3-azahexadecan-16-yl)propane-1,3-diyl dioctanoate;
2-(8-dodecyl-2-methyl-6,12-dioxo-5,7,11-trioxa-2-azaheptadecan-17-yl)propane-1,3-diyl dioctanoate;
2-(10-dodecyl-3-ethyl-8,14-dioxo-7,9,13-trioxa-3-azanonadecan-19-yl)propane-1,3-diyl dioctanoate;
2-(9-dodecyl-2-methyl-7,13-dioxo-6,8,12-trioxa-2-azaoctadecan-18-yl)propane-1,3-diyl dioctanoate;
2-(8-dodecyl-2-methyl-6,12-dioxo-5,7,11-trioxa-2-azaoctadecan-18-yl)propane-1,3-diyl dioctanoate;
2-(10-dodecyl-3-ethyl-8,14-dioxo-7,9,13-trioxa-3-aza-icosan-20-yl)propane-1,3-diyl dioctanoate;
2-(9-dodecyl-2-methyl-7,13-dioxo-6,8,12-trioxa-2-azanonadecan-19-yl)propane-1,3-diyl dioctanoate;
3-(((3-(diethylamino)propoxy)carbonyl)oxy)pentadecyl 4,4-bis(octyloxy)butanoate;
3-(((3-(diethylamino)propoxy)carbonyl)oxy)pentadecyl 4,4-bis((2-ethylhexyl)oxy)butanoate;
3-(((3-(diethylamino)propoxy)carbonyl)oxy)pentadecyl 4,4-bis((2-propylpentyl)oxy)butanoate;
3-(((3-(ethyl(methyl)amino)propoxy)carbonyl)oxy)pentadecyl 4,4-bis((2-propylpentyl)oxy)butanoate;
3-(((3-(dimethylamino)propoxy)carbonyl)oxy)pentadecyl 4,4-bis((2-propylpentyl)oxy)butanoate;
3-(((3-(diethylamino)propoxy)carbonyl)oxy)pentadecyl 6,6-bis(octyloxy)hexanoate;
3-(((3-(diethylamino)propoxy)carbonyl)oxy)pentadecyl 6,6-bis(hexyloxy)hexanoate;
3-(((3-(diethylamino)propoxy)carbonyl)oxy)pentadecyl 6,6-bis((2-ethylhexyl)oxy)hexanoate;

3-(((3-(diethylamino)propoxy)carbonyl)oxy)pentadecyl 8,8-bis(hexyloxy)octanoate;
3-(((3-(diethylamino)propoxy)carbonyl)oxy)pentadecyl 8,8-dibutoxyoctanoate;
3-(((3-(diethylamino)propoxy) carbonyl)oxy)pentadecyl 8,8-bis((2-propylpentyl)oxy)octanoate;
3-(((3-(ethyl(methyl)amino)propoxy)carbonyl)oxy)pentadecyl 8,8-bis((2-propylpentyl)oxy)octanoate;
3-(((3-(dimethylamino)propoxy)carbonyl)oxy)pentadecyl 8,8-bis((2-propylpentyl)oxy)octanoate;
3-(((3-(dimethylamino)propoxy)carbonyl)oxy)pentadecyl 3-octylundecanoate;
3-(((3-(dimethylamino)propoxy)carbonyl)oxy)pentadecyl 3-octylundec-2-enoate;
3-(((3-(dimethylamino)propoxy)carbonyl)oxy)pentadecyl 7-hexyltridec-6-enoate;
3-(((3-(dimethylamino)propoxy)carbonyl)oxy)pentadecyl 9-pentyltetradecanoate;
3-(((3-(dimethylamino)propoxy)carbonyl)oxy)pentadecyl 9-pentyltetradec-8-enoate;
3-(((3-(dimethylamino)propoxy)carbonyl)oxy)pentadecyl 5-heptyldodecanoate;
3-(((3-(dimethylamino)propoxy)carbonyl)oxy)tridecyl 5-heptyldodecanoate;
3-(((3-(dimethylamino)propoxy)carbonyl)oxy)undecyl 5-heptyldodecanoate;
1,3-bis(octanoyloxy)propan-2-yl (3-(((2-(dimethylamino)ethoxy)carbonyl)oxy)pentadecyl) succinate;
1,3-bis(octanoyloxy)propan-2-yl (3-(((3-(dimethylamino)propoxy)carbonyl)oxy)pentadecyl) succinate;
1-(3-(((3-(dimethylamino)propoxy)carbonyl)oxy)pentadecyl) 10-octyl decanedioate;
1-(3-(((3-(diethylamino)propoxy)carbonyl)oxy)pentadecyl) 10-octyl decanedioate;
1-(3-(((3-(ethyl(methyl)amino)propoxy)carbonyl)oxy)pentadecyl) 10-octyl decanedioate;
1-(3-(((3-(diethylamino)propoxy)carbonyl)oxy)pentadecyl) 10-(2-ethylhexyl) decanedioate;
1-(3-(((3-(ethyl(methyl)amino)propoxy)carbonyl)oxy)pentadecyl) 10-(2-ethylhexyl) decanedioate;
3-(((3-(dimethylamino)propoxy)carbonyl)oxy)pentadecyl 10-(octanoyloxy)decanoate;
8-dodecyl-2-methyl-6,12-dioxo-5,7,11-trioxa-2-azanonadecan-19-yl decanoate;
3-(((3-(diethylamino)propoxy)carbonyl)oxy)pentadecyl 10-(octanoyloxy)decanoate;
3-(((3-(ethyl(methyl)amino)propoxy)carbonyl)oxy)pentadecyl 10-(octanoyloxy)decanoate;
(9Z,12Z)-3-(((3-(dimethylamino)propoxy)carbonyl)oxy)pentadecyl octadeca-9,12-dienoate;
(9Z,12Z)-3-(((3-(diethylamino)propoxy)carbonyl)oxy)pentadecyl octadeca-9,12-dienoate;
(9Z,12Z)-3-(((3-(ethyl(methyl)amino)propoxy)carbonyl)oxy)pentadecyl octadeca-9,12-dienoate;
(9Z,12Z)-3-(((2-(dimethylamino)ethoxy)carbonyl)oxy)pentadecyl octadeca-9,12-dienoate;
1-((9Z,12Z)-octadeca-9,12-dienoyloxy)pentadecan-3-yl 1,4-dimethylpiperidine-4-carboxylate;
2-(((3-(diethylamino)propoxy)carbonyl)oxy)tetradecyl 4,4-bis((2-ethylhexyl)oxy)butanoate;
(9Z,12Z)-(12Z,15Z)-3-((3-(dimethylamino)propanoyl)oxy) henicosa-12,15-dien-1-yl octadeca-9,12-dienoate;
(12Z,15Z)-3-((4-(dimethylamino)butanoyl)oxy)henicosa-12,15-dien-1-yl 3-octylundecanoate;
(12Z,15Z)-3-((4-(dimethylamino)butanoyl)oxy)henicosa-12,15-dien-1-yl 5-heptyldodecanoate;
(12Z,15Z)-3-((4-(dimethylamino)butanoyl)oxy)henicosa-12,15-dien-1-yl 7-hexyltridecanoate;
(12Z,15Z)-3-((4-(dimethylamino)butanoyl)oxy)henicosa-12,15-dien-1-yl 9-pentyltetradecanoate;
(12Z,15Z)-1-((((9Z,12Z)-octadeca-9,12-dien-1-yloxy)carbonyl)oxy)henicosa-12,15-dien-3-yl 3-(dimethylamino)propanoate;
(13Z,16Z)-4-(((2-(dimethylamino)ethoxy)carbonyl)oxy)docosa-13,16-dien-1-yl 2,2-bis(heptyloxy)acetate;
(13Z,16Z)-4-(((3-(diethylamino)propoxy)carbonyl)oxy)docosa-13,16-dien-1-yl 2,2-bis(heptyloxy)acetate;
2,2-bis(heptyloxy)ethyl 3-((3-ethyl-10-((9Z,12Z)-octadeca-9,12-dien-1-yl)-8,15-dioxo-7,9,14-trioxa-3-azaheptadecan-17-yl)disulfanyl)propanoate;
(13Z,16Z)-4-(((3-(dimethylamino)propoxy)carbonyl)oxy) docosa-13,16-dien-1-yl heptadecan-9-yl succinate;
(9Z,12Z)-2-(((11Z,14Z)-2-((3-(dimethylamino)propanoyl) oxy)icosa-11,14-dien-1-yl)oxy)ethyl octadeca-9,12-dienoate;
(9Z,12Z)-3-(((3-(dimethylamino)propoxy)carbonyl)oxy)-13-(octanoyloxy)tridecyl octadeca-9,12-dienoate;
3-(((3-(dimethylamino)propoxy)carbonyl)oxy)-13-(octanoyloxy)tridecyl 3-octylundecanoate;
3-(((3-(dimethylamino)propoxy)carbonyl)oxy)-13-hydroxytridecyl 5-heptyldodecanoate;
3-(((3-(dimethylamino)propoxy)carbonyl)oxy)-13-(octanoyloxy)tridecyl 5-heptyldodecanoate;
3-(((3-(dimethylamino)propoxy)carbonyl)oxy)-13-(octanoyloxy)tridecyl 7-hexyltridecanoate;
3-(((3-(dimethylamino)propoxy)carbonyl)oxy)-13-hydroxytridecyl 9-pentyltetradecanoate;
3-(((3-(dimethylamino)propoxy)carbonyl)oxy)-13-(octanoyloxy)tridecyl 9-pentyltetradecanoate;
1-(3-(((3-(dimethylamino)propoxy)carbonyl)oxy)-13-(octanoyloxy)tridecyl) 10-octyl decanedioate;
3-(((3-(dimethylamino)propoxy)carbonyl)oxy)-13-(octanoyloxy)tridecyl 10-(octanoyloxy)decanoate;
(9Z,12Z)-3-(((3-(dimethylamino)propoxy)carbonyl)oxy)-5-octyltridecyl octadeca-9,12-dienoate;
3-(((3-(dimethylamino)propoxy)carbonyl)oxy)-5-octyltridecyl decanoate;
5-(((3-(dimethylamino)propoxy)carbonyl)oxy)-7-octylpentadecyl octanoate;
(9Z,12Z)-5-(((3-(dimethylamino)propoxy)carbonyl)oxy)-7-octylpentadecyl octadeca-9,12-dienoate;
9-(((3-(dimethylamino)propoxy)carbonyl)oxy)-11-octylnonadecyl octanoate;
9-(((3-(dimethylamino)propoxy)carbonyl)oxy)-11-octylnonadecyl decanoate;
(9Z,12Z)-9-(((3-(dimethylamino)propoxy)carbonyl)oxy) nonadecyl octadeca-9,12-dienoate;
9-(((3-(dimethylamino)propoxy)carbonyl)oxy)nonadecyl hexanoate;
9-(((3-(dimethylamino)propoxy)carbonyl)oxy)nonadecyl 3-octylundecanoate;
9-((4-(dimethylamino)butanoyl)oxy)nonadecyl hexanoate;
9-((4-(dimethylamino)butanoyl)oxy)nonadecyl 3-octylundecanoate;
(9Z,9'Z,12Z,12'Z)-2-((4-(((3-(dimethylamino)propoxy)carbonyl)oxy)hexadecanoyl)oxy)propane-1,3-diyl bis(octadeca-9,12-dienoate);
(9Z,9'Z,12Z,12'Z)-2-((4-(((3-(diethylamino)propoxy)carbonyl)oxy)hexadecanoyl)oxy)propane-1,3-diyl bis(octadeca-9,12-dienoate);
(9Z,9'Z,12Z,12'Z,15Z,15'Z)-2-((4-(((3-(dimethylamino) propoxy)carbonyl)oxy) hexadecanoyl)oxy)propane-1,3-diyl bis(octadeca-9,12,15-trienoate);

(Z)-2-((4-(((3-(dimethylamino)propoxy)carbonyl)oxy)
hexadecanoyl)oxy)propane-1,3-diyl dioleate;
2-((4-(((3-(diethylamino)propoxy)carbonyl)oxy)hexadecanoyl)oxy)propane-1,3-diyl ditetradecanoate;
2-((4-(((3-(dimethylamino)propoxy)carbonyl)oxy)hexadecanoyl)oxy)propane-1,3-diyl ditetradecanoate;
2-((4-(((3-(ethyl(methyl)amino)propoxy)carbonyl)oxy)
hexadecanoyl)oxy)propane-1,3-diyl ditetradecanoate;
2-((4-(((3-(dimethylamino)propoxy)carbonyl)oxy)hexadecanoyl)oxy)propane-1,3-diyl didodecanoate;
2-((4-(((3-(diethylamino)propoxy)carbonyl)oxy)hexadecanoyl)oxy)propane-1,3-diyl didodecanoate;
2-((4-(((3-(ethyl(methyl)amino)propoxy)carbonyl)oxy)
hexadecanoyl)oxy)propane-1,3-diyl didodecanoate;
2-((4-(((3-(diethylamino)propoxy)carbonyl)oxy)hexadecanoyl)oxy)propane-1,3-diyl bis(decanoate);
2-((4-(((3-(ethyl(methyl)amino)propoxy)carbonyl)oxy)
hexadecanoyl)oxy)propane-1,3-diyl bis(decanoate);
2-((4-(((3-(diethylamino)propoxy)carbonyl)oxy)hexadecanoyl)oxy)propane-1,3-diyl dioctanoate;
2-((4-(((3-(ethyl(methyl)amino)propoxy)carbonyl)oxy)
hexadecanoyl)oxy)propane-1,3-diyl dioctanoate;
2-(((13Z,16Z)-4-(((3-(dimethylamino)propoxy)carbonyl)
oxy)docosa-13,16-dienoyl)oxy)propane-1,3-diyl dioctanoate;
2-(((13Z,16Z)-4-(((3-(diethylamino)propoxy)carbonyl)oxy)
docosa-13,16-dienoyl)oxy)propane-1,3-diyl dioctanoate;
(9Z,9'Z,12Z,12'Z)-2-((2-(((3-(diethylamino)propoxy)carbonyl)oxy)tetradecanoyl)oxy)propane-1,3-diyl bis(octadeca-9,12-dienoate);
(9Z,9'Z,12Z,12'Z)-2-((2-(((3-(dimethylamino)propoxy)carbonyl)oxy)dodecanoyl)oxy)propane-1,3-diyl bis(octadeca-9,12-dienoate);
(9Z,9'Z,12Z,12'Z)-2-((2-(((3-(dimethylamino)propoxy)carbonyl)oxy)tetradecanoyl)oxy)propane-1,3-diyl bis(octadeca-9,12-dienoate);
(9Z,9'Z,12Z,12'Z)-2-((2-(((3-(diethylamino)propoxy)carbonyl)oxy)dodecanoyl)oxy)propane-1,3-diyl bis(octadeca-9,12-dienoate);
2-((2-(((3-(diethylamino)propoxy)carbonyl)oxy)tetradecanoyl)oxy)propane-1,3-diyl dioctanoate;
4,4-bis(octyloxy)butyl 4-(((3-(dimethylamino)propoxy)carbonyl)oxy)hexadecanoate;
4,4-bis(octyloxy)butyl 2-(((3-(diethylamino)propoxy)carbonyl)oxy)dodecanoate;
(9Z,12Z)-10-dodecyl-3-ethyl-14-(2-((9Z,12Z)-octadeca-9,12-dienoyloxy)ethyl)-8,13-dioxo-7,9-dioxa-3,14-diazahexadecan-16-yl octadeca-9,12-dienoate;
2-((4-(((3-(diethylamino)propoxy)carbonyl)oxy)-11-(octanoyloxy)undecanoyl)oxy)propane-1,3-diyl dioctanoate; and
(9Z,9'Z,12Z,12'Z)-2-(9-dodecyl-2-methyl-7,12-dioxo-6,8,13-trioxa-2-azatetradecan-14-yl)propane-1,3-diyl bis(octadeca-9,12-dienoate).

As used herein, the term "alkyl" refers to a fully saturated branched or unbranched hydrocarbon chain having the specified number of carbon atoms. For example, $C_{1-8}$ alkyl refers to an alkyl group having from 1 to 8 carbon atoms. For example, $C_{4-22}$ alkyl refers to an alkyl group having from 4 to 22 carbon atoms. For example, $C_{6-10}$ alkyl refers to an alkyl group having from 6 to 10 carbon atoms. For example, $C_{12-22}$ alkyl refers to an alkyl group having from 12 to 22 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecanyl, n-dodecanyl, n-tridecanyl, 9-methylheptadecanyl, 1-heptyldecyl, 2-octyldecyl, 6-hexyldodecyl, 4-heptylundecyl, and the like.

As used herein, the term "alkylene" refers to divalent alkyl group as defined herein above. Representative examples of alkylene include, but are not limited to, methylene, ethylene, n-propylene, iso-propylene, n-butylene, sec-butylene, iso-butylene, tert-butylene, n-pentylene, iso-pentylene, neopentylene, n-hexylene, 3-methylhexylene, 2,2-dimethylpentylene, 2,3-dimethylpentylene, n-heptylene, n-octylene, n-nonylene, n-decylene, and the like.

As used herein, the term "alkenyl" refers to an unsaturated branched or unbranched hydrocarbon chain having the specified number of carbon atoms and one or more carbon-carbon double bonds within the chain. For example, $C_{12-22}$ alkenyl refers to an alkenyl group having 12 to 22 carbon atoms with one or more carbon-carbon double bonds within the chain. In certain embodiments alkenyl groups have one carbon-carbon double bond within the chain. In other embodiments, alkenyl groups have more than one carbon-carbon double bond within the chain. Alkyenyl groups may be optionally substituted with one or more substituents as defined in formulas (I) or (III). Representative examples of alkenyl include, but are not limited to, ethylenyl, propenyl, butenyl, pentenyl, hexenyl and the like. Other examples of alkenyl include, but are not limited to: Z-octadec-9-enyl, Z-undec-7-enyl, Z-heptadeca-8-enyl, (9Z,12Z)-octadeca-9,12-dienyl, (8Z,11Z)-heptadeca-8,11-dienyl, (8Z,11Z,14Z)-heptadeca-8,11,14-trienyl, linolenyl, 2-octyldeca-1-enyl, linoleyl and olelyl.

As used herein, the term "alkenylene" refers a divalent alkenyl group as defined herein above. Representative examples of alkenylene include, but are not limited to, ethenylene, propenylene, butenylene, pentenylene, hexenylene and the like.

As used herein, the term "alkoxy" refers to refers to any alkyl moiety attached through an oxygen bridge (i.e. a —O—$C_{1-3}$ alkyl group wherein $C_{1-3}$ alkyl is as defined herein). Examples of such groups include, but are not limited to, methoxy, ethoxy, and propoxy.

As used herein, the term "cycloalkyl" refers to a saturated monocyclic, bicyclic or tricyclic hydrocarbon ring having the specified number of carbon atoms. For example, $C_{3-7}$ cycloalkyl refers to a cycloalkyl ring having from 3 to 7 carbon atoms. Cycloalkyl groups may be optionally substituted with one or more substituents as defined in formula (I). Representative examples of cycloalkyl include, but are not limited to, cyclopropyl, cyclobutyl, cyclopentyl, cyclohexyl, bicyclo[2.1.1]hexyl, bicyclo[2.2.1]heptyl, adamantyl and the like.

As used herein, the term "halo" refers to fluoro, chloro, bromo, and iodo.

As used herein, the term "heterocyclic" refers to a 4 to 12 membered saturated or unsaturated monocyclic or bicyclic ring containing from 1 to 4 heteroatoms. Heterocyclic ring systems are not aromatic. Heterocyclic groups containing more than one heteroatom may contain different heteroatoms. Heterocyclic groups are monocyclic, spiro, or fused or bridged bicyclic ring systems. Examples of monocyclic heterocyclic groups include tetrahydrofuranyl, dihydrofuranyl, 1,4-dioxanyl, morpholinyl, 1,4-dithianyl, azetidinyl, piperazinyl, piperidinyl, 1,3-dioxolanyl, imidazolidinyl, imidazolinyl, pyrrolinyl, pyrrolidinyl, tetrahydropyranyl, dihydropyranyl, 1,2,3,6-tetrahydropyridinyl, oxathiolanyl, dithiolanyl, 1,3-dioxanyl, 1,3-dithianyl, oxathianyl, thiomorpholinyl, 1,4,7-trioxa-10-azacyclododecanyl, azapanyl and the like. Examples of spiro heterocyclic rings include, but are not limited to, 1,5-dioxa-9-azaspiro[5.5]undecanyl, 1,4-dioxa-8-azaspiro[4.5]decanyl, 2-oxa-7-azaspiro[3.5]nonanyl, and the like. Fused heterocyclic ring systems have from 8 to 11 ring atoms and include groups wherein a heterocyclic ring is fused to a phenyl ring. Examples of fused heterocyclic rings include, but are not limited to decahydroqunilinyl, (4aS,8aR)-decahydroisoquinolinyl, (4aS,8aS)-decahydroisoquinolinyl, octahydrocyclopenta[c]pyrrolyl, isoinolinyl, (3aR,7aS)-hexahydro-[1,3]dioxolo[4.5-c]pyridinyl, octahydro-1H-pyrrolo[3,4-b]pyridinyl, tetrahydroisoquinolinyl and the like.

As used herein, the term "heterocyclyl$C_{1-8}$alkyl" refers to a heterocyclic ring as defined above which is attached to the rest of the molecule by a single bond or by a $C_{1-8}$alkyl radical as defined above.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heteroaryl$C_{1-8}$alkyl" refers to a heteroaryl ring as defined above which is attached to the rest of the molecule by a single bond or by a $C_{1-8}$alkyl radical as defined above.

3.2 Neutral Lipids

Neutral lipids suitable for use in a lipid composition of the invention include, for example, a variety of neutral, uncharged or zwitterionic lipids. Examples of neutral phospholipids suitable for use in the present invention include, but are not limited to: 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphophatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the neutral phospholipid is selected from the group consisting of distearoylphosphatidylcholine (DSPC) and dimyristoyl phosphatidyl ethanolamine (DMPE).

3.3 Anionic Lipids

Anionic lipids suitable for use in the present invention include, but are not limited to, phosphatidylglycerol, cardiolipin, diacylphosphatidylserine, diacylphosphatidic acid, N-dodecanoyl phosphatidyl ethanoloamine, N-succinyl phosphatidylethanolamine, N-glutaryl phosphatidylethanolamine cholesterol hemisuccinate (CHEMS), and lysylphosphatidylglycerol.

3.4 Helper Lipids

Helper lipids are lipids that enhance transfection (e.g. transfection of the nanoparticle including the biologically active agent) to some extent. The mechanism by which the helper lipid enhances transfection may include, e.g., enhancing particle stability and/or enhancing membrane fusogenicity. Helper lipids include steroids and alkyl resorcinols. Helper lipids suitable for use in the present invention include, but are not limited to, cholesterol, 5-heptadecylresorcinol, and cholesterol hemisuccinate.

3.4 Stealth Lipids

Stealth lipids are lipids that increase the length of time for which the nanoparticles can exist in vivo (e.g. in the blood). Stealth lipids suitable for use in a lipid composition of the invention include, but are not limited to, stealth lipids having a hydrophilic head group linked to a lipid moiety. Examples of such stealth lipids include compounds of formula (XI), as described in WO2011/076807,

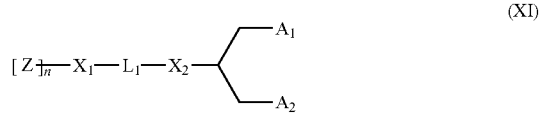

(XI)

or a salt or pharmaceutically acceptable derivative thereof, wherein:

Z is a hydrophilic head group component selected from PEG and polymers based on poly(oxazoline), poly(ethyleneoxide), poly(vinyl alcohol), poly(glycerol), poly(N-vinylpyrrolidone), poly[N-(2-hydroxypropyl)methacrylamide], polysaccharides and poly(amino acid)s, wherein the polymer may be linear or branched, and wherein the polymer may be optionally substituted;

wherein Z is polymerized by n subunits;

n is a number-averaged degree of polymerization between 10 and 200 units of Z, wherein n is optimized for different polymer types;

$L_1$ is an optionally substituted $C_{1-10}$ alkylene or $C_{1-10}$ heteroalkylene linker including zero, one, two or more of an ether (e.g., —O—), ester (e.g., —C(O)O—), succinate (e.g., —O(O)C—CH$_2$—CH$_2$—C(O)O—)), carbamate (e.g., —OC(O)—NR'—), carbonate (e.g., —OC(O)O—), ketone (e.g., —C—C(O)—C—), carbonyl (e.g., —C(O)—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—); any of which may be substituted by zero, one or more Z groups;

wherein R' is independently selected from —H, —NH—, —NH$_2$, —O—, —S—, a phosphate or an optionally substituted $C_{1-10}$ alkylene;

$X_1$ and $X_2$ are independently selected from a carbon or a heteroatom selected from —NH—, —O—, —S— or a phosphate;

$A_1$ and $A_2$ are independently selected from a $C_{6-30}$ alkyl, $C_{6-30}$ alkenyl, and $C_{6-30}$ alkynyl, wherein $A_1$ and $A_2$ may be the same or different, or wherein $A_1$ and $A_2$ together with the carbon atom to which they are attached form an optionally substituted steroid.

Specific stealth lipids include, but are not limited to, those listed in Table 1.

TABLE 1

Stealth Lipids

| Stealth Lipid | Lipid |
|---|---|
| S001 | |
| S002 | |
| S003 | |
| S004 | |
| S005 | |
| S006 | |
| S007 | |
| S008 | |

TABLE 1-continued

Stealth Lipids

| Stealth Lipid | Lipid |
|---|---|
| S009 | |
| S010 | |
| S011 | |
| S012 | |
| S013 | |
| S014 | |
| S015 | |
| S016 | |
| S017 | |
| S018 | |

TABLE 1-continued

Stealth Lipids

| Stealth Lipid | Lipid |
|---|---|
| S019 | |
| S020 | |
| S021 | |
| S022 | |
| S023 | |
| S024 | |
| S025 | |
| S026 | |
| S027 | |
| S028 | |

TABLE 1-continued

Stealth Lipids

| Stealth Lipid | Lipid |
|---|---|
| S029 | 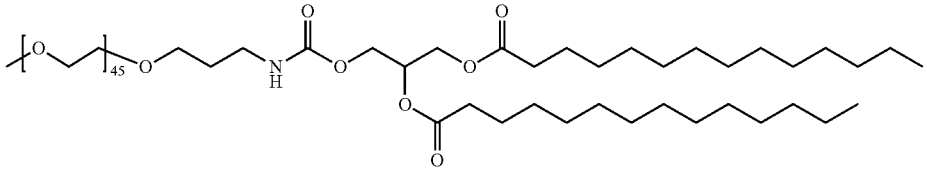 |
| S030 | 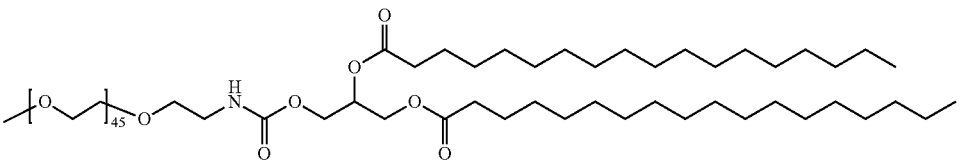 |
| S031 | 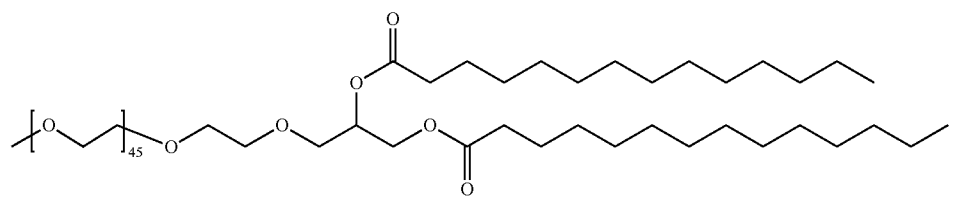 |
| S032 | 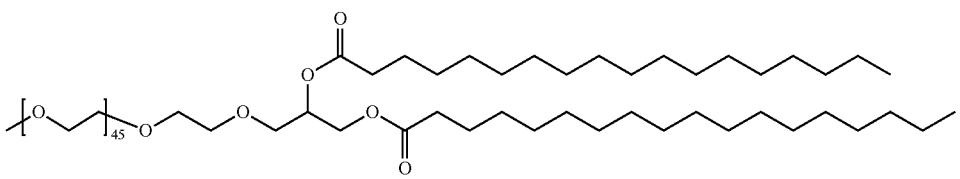 |
| S033 | 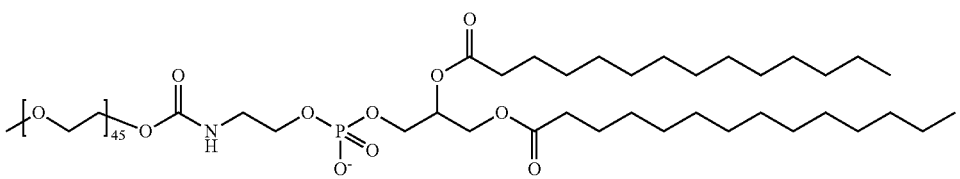 |

Other stealth lipids suitable for use in a lipid composition of the present invention and information about the biochemistry of such lipids can be found in Romberg et al., Pharmaceutical Research, Vol. 25, No. 1, 2008, p. 55-71 and Hoekstra et al., Biochimica et Biophysica Acta 1660 (2004) 41-52.

In one embodiment, the suitable stealth lipid comprises a group selected from PEG (sometimes referred to as poly (ethylene oxide) and polymers based on poly(oxazoline), poly(vinyl alcohol), poly(glycerol), poly(N-vinylpyrrolidone), polyaminoacids and poly[N-(2-hydroxypropyl) methacrylamide]. Additional suitable PEG lipids are disclosed, e.g., in WO 2006/007712.

Specific suitable stealth lipids include polyethyleneglycol-diacylglycerol or polyethyleneglycol-diacylglycamide (PEG-DAG) conjugates including those comprising a dialkylglycerol or dialkylglycamide group having alkyl chain length independently comprising from about $C_4$ to about $C_{40}$ saturated or unsaturated carbon atoms. The dialkylglycerol or dialkylglycamide group can further comprise one or more substituted alkyl groups. In any of the embodiments described herein, the PEG conjugate can be selected from PEG-dilaurylglycerol, PEG-dimyristylglycerol (PEG-DMG) (catalog # GM-020 from NOF, Tokyo, Japan), PEG-dipalmitoylglycerol, PEG-disterylglycerol, PEG-dilaurylglycamide, PEG-dimyristylglycamide, PEG-dipalmitoylglycamide, and PEG-disterylglycamide, PEG-cholesterol (1-[8'-(Cholest-5-en-3 [beta]-oxy)carboxamido-3',6'-dioxaoctanyl]carbamoyl-[omega]-methyl-poly (ethylene glycol), PEG-DMB (3,4-Ditetradecoxylbenzyl-[omega]-methyl-poly(ethylene glycol) ether), 1,2-dimyristoyl-sn-glycero-3-phosphoethanolamine-N-[methoxy(polyethylene glycol)-2000] (catalog #880150P from Avanti Polar Lipids, Alabaster, Ala., USA).

In one embodiment the stealth lipid is S010, S024, S027, S031, or S033.

In another embodiment the stealth lipid is S024.

Unless otherwise indicated, the term "PEG" as used herein means any polyethylene glycol or other polyalkylene ether polymer. In one embodiment, PEG is an optionally substituted linear or branched polymer of ethylene glycol or ethylene oxide. In one embodiment PEG is unsubstituted. In one embodiment the PEG is substituted, e.g., by one or more alkyl, alkoxy, acyl, hydroxy or aryl groups. In one embodiment, the term includes PEG copolymers such as PEG-polyurethane or PEG-polypropylene (see, e.g., J. Milton Harris, Poly(ethylene glycol) chemistry: biotechnical and biomedical applications (1992)); in another embodiment, the term does not include PEG copolymers. In one embodiment, the PEG has a molecular weight of from about 130 to about 50,000, in a sub-embodiment about 150 to about 30,000, in a sub-embodiment about 150 to about 20,000, in a sub-embodiment about 150 to about 15,000, in a sub-embodiment about 150 to about 10,000, in a sub-embodiment about 150 to about 6000, in a sub-embodiment about 150 to about 5000, in a sub-embodiment about 150 to about 4000, in a sub-embodiment about 150 to about 3000, in a sub-embodiment about 300 to about 3000, in a sub-embodiment about 1000 to about 3000, and in a sub-embodiment about 1500 to about 2500.

In certain embodiments the PEG is a "PEG-2K", also termed "PEG 2000", which has an average molecular weight of about 2000 daltons. PEG-2K is represented herein by the following formula (XIIa), wherein n is 45, meaning that the number-averaged degree of polymerization comprises about 45 subunits. However, other PEG embodiments known in the art may be used, including, e.g., those where the number-averaged degree of polymerization comprises about 23 subunits (n=23) and/or 68 subunits (n=68).

(XIIa)

Preferred compounds of formulas (I)-(IX) for use in the processes of the invention are Examples 1-36 below.

4.0 Encapsulated Nucleic Acid Nanoparticles

By "lipid nanoparticle" is meant a particle that comprises a plurality of (i.e. more than one) lipid molecules physically associated with each other by intermolecular forces. The lipid nanoparticles may be, e.g., microspheres (including unilamellar and multilamellar vesicles, e.g. liposomes), a dispersed phase in an emulsion, micelles or an internal phase in a suspension.

The term "lipid nanoparticle host" refers to a plurality of lipid molecules physically associated with each other by intermolecular forces/electrostatic interactions to encapsulate one or more nucleic acid molecules, such as an siRNA.

Certain embodiments provide an encapsulated nucleic acid nanoparticle composition comprising a pharmaceutically acceptable carrier and an encapsulated nucleic acid nanoparticle. The encapsulated nucleic acid nanoparticle includes a lipid nanoparticle host and a nucleic acid that is encapsulated in the lipid nanoparticle host. The term "pharmaceutically acceptable carrier" as used herein, means a non-toxic, inert diluent. Materials which can serve as pharmaceutically acceptable carriers include, but are not limited to, pyrogen-free water, deionized water, isotonic saline, Ringer's solution, and phosphate buffer solutions. In preferred embodiments, the encapsulated nucleic acid nanoparticle has an average size of about 40 to about 70 nm and a polydispersity index of less than about 0.1 as determined by dynamic light scattering, e.g., using a Malvern Zetasizer Nano ZS. The lipid nanoparticle host comprises a degradable cationic lipid, a lipidated polyethylene glycol, cholesterol, and 1,2-distearoyl-sn-glycero-3-phosphocholine components as described elsewhere herein.

Embodiments of the present invention provide methods of preparing an encapsulated nucleic acid nanoparticle composition comprising a cationic lipid and another lipid component. Another embodiment provides a method using a cationic lipid and a helper lipid, for example cholesterol. Another embodiment provides for a method using a cationic lipid, a helper lipid, for example cholesterol, and a neutral lipid, for example DSPC. Another embodiment of the present invention provides a method using a cationic lipid, a helper lipid, for example cholesterol, a neutral lipid, for example DSPC, and a stealth lipid, for example S010, S024, S027, S031, or S033. Another embodiment of the present invention provides for a method of encapsulating a nucleic acid in a lipid nanoparticle host where the nanoparticle comprises a cationic lipid, a helper lipid, for example cholesterol, a neutral lipid, for example DSPC, a stealth lipid, for example S010, S024, S027, S031, or S033, and the nucleic acid is, for example a RNA or DNA. Another embodiment of the present invention provides a method of using a cationic lipid, a helper lipid, for example cholesterol, a neutral lipid, for example DSPC, and a stealth lipid, for example S010, S024, S027, S031, or S033, where the nucleic acid is, for example, mRNA, siRNA or DNA.

In some embodiments of the invention, the lipid solution/stream(s) contain a cationic lipid compound, a helper lipid (cholesterol), an optional neutral lipid (DSPC) and a stealth lipid (e.g., S010, S024, S027, or S031). Where a formulation contains four lipid components, the molar ratios of the lipids may range from 20 to 70 mole percent for the cationic lipid with a target of 40-60, the mole percent of helper lipid ranges from 20 to 70 with a target of 30 to 50, the mole percent of neutral lipid ranges from 0-30, the mole percent of PEG lipid has a range from 1 to 6 with a target of 2 to 5.

In some embodiments, the lipid solution/stream(s) contain 30-60% of a compound of formula (III), 30-60% cholesterol/ 5-10% DSPC, and 1-5% PEG-DMG, S010, S011 or S024.

Another embodiment of the present invention provides a method of encapsulating a nucleic acid in a lipid nanoparticle host using a cationic lipid and a helper lipid, for example cholesterol, in a lipid molar ratio of about 40-55 cationic lipid/about 40-55 helper lipid. Another embodiment provides a method using a cationic lipid, a helper lipid, for example cholesterol, and a neutral lipid, for example DSPC in a lipid molar ratio of about 40-55 a cationic lipid/about 40-55 helper lipid/about 5-15 neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 40-55 cationic lipid/ about 40-55 helper lipid/about 5-15 neutral lipid/about 1-10 stealth lipid.

Another embodiment of the present invention provides a method of encapsulating a nucleic acid in a lipid nanoparticle host using a cationic lipid and a helper lipid, for example cholesterol, in a lipid molar ratio of about 40-50 cationic lipid/about 40-50 helper lipid. Another embodiment provides a method using a cationic lipid, a helper lipid, for example cholesterol, and a neutral lipid, for example DSPC in a lipid molar ratio of about 40-50 cationic lipid/about 40-50 helper lipid/about 5-15 neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 40-50 cationic lipid/ about 40-50 helper lipid/about 5-15 neutral lipid/about 1-5 stealth lipid.

Another embodiment of the present invention provides a method of encapsulating a nucleic acid in a lipid nanoparticle host using a cationic lipid and a helper lipid, for example cholesterol, in a lipid molar ratio of about 43-47 cationic lipid/about 43-47 helper lipid. Another embodiment provides a method using a cationic lipid, a helper lipid, for example cholesterol, and a neutral lipid, for example DSPC in a lipid molar ratio of about 43-47 cationic lipid/about 43-47 helper lipid/about 7-12 neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 43-47 cationic lipid/about 43-47 helper lipid/about 7-12 neutral lipid/about 1-4 stealth lipid.

Another embodiment of the present invention provides a method of encapsulating a nucleic acid in a lipid nanoparticle host using a cationic lipid and a helper lipid, for example cholesterol, in a lipid molar ratio of about 45% cationic lipid and about 44% helper lipid. Another embodiment provides a method using a cationic lipid, a helper lipid, for example cholesterol, and a neutral lipid, for example DSPC in a lipid molar ratio of about 45% cationic lipid, about 44% helper lipid, and about 9% neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 45% cationic lipid, about 44% helper lipid, about 9% neutral lipid, and about 2% stealth lipid.

One embodiment of the present invention provides a method of preparing an encapsulated nucleic acid nanoparticle composition comprising a compound of formula (I) and another lipid component. Another embodiment provides a method using a compound of formula (I) and a helper lipid, for example cholesterol. Another embodiment provides for a method using a compound of formula (I), a helper lipid, for example cholesterol, and a neutral lipid, for example DSPC. Another embodiment of the present invention provides a method using a compound of formula (I), a helper lipid, for example cholesterol, a neutral lipid, for example DSPC, and a stealth lipid, for example S010, S024, S027, S031, or S033. Another embodiment of the present invention provides for a method of encapsulating a nucleic acid in a lipid nanoparticle host where the nanoparticle comprises a compound of formula (I), a helper lipid, for example cholesterol, a neutral lipid, for example DSPC, a stealth lipid, for example S010, S024, S027, S031, or S033, and the nucleic acid is, for example a RNA or DNA. Another embodiment of the present invention provides a method of using a compound of formula (I) a helper lipid, for example cholesterol, a neutral lipid, for example DSPC, and a stealth lipid, for example S010, S024, S027, S031, or S033, where the nucleic acid is, for example, mRNA, siRNA or DNA.

Another embodiment of the present invention provides a method of encapsulating a nucleic acid in a lipid nanoparticle host using a compound of any of formulas (I)-(IX) and a helper lipid, for example cholesterol, in a lipid molar ratio of about 40-55 compound of formula (I)/about 40-55 helper lipid. Another embodiment provides a method using a compound of any of formulas (I)-(IX), a helper lipid, for example cholesterol, and a neutral lipid, for example DSPC in a lipid molar ratio of about 40-55 compound of any of formulas (I)-(IX)/about 40-55 helper lipid/about 5-15 neutral lipid. Another embodiment provides a method using a compound of any of formulas (I)-(IX), a helper lipid, for example cholesterol, a neutral lipid, for example DSPC, and a stealth lipid, for example S010, S024, S027, S031, or S033 in a lipid molar ratio of about 40-55 compound of formula (I)/about 40-55 helper lipid/about 5-15 neutral lipid/about 1-10 stealth lipid.

Another embodiment of the present invention provides a method of encapsulating a nucleic acid in a lipid nanoparticle host using a compound of any of formulas (I)-(IX) and a helper lipid, for example cholesterol, in a lipid molar ratio of about 40-50 compound of any of formulas (I)-(IX)/about 40-50 helper lipid. Another embodiment provides a method using a compound of any of formulas (I)-(IX), a helper lipid, for example cholesterol, and a neutral lipid, for example DSPC in a lipid molar ratio of about 40-50 compound of any of formulas (I)-(IX)/about 40-50 helper lipid/about 5-15 neutral lipid. Another embodiment provides a method using a compound of any of formulas (I)-(IX), a helper lipid, for example cholesterol, a neutral lipid, for example DSPC, and a stealth lipid, for example S010, S024, S027, S031, or S033 in a lipid molar ratio of about 40-50 compound of any of formulas (I)-(IX)/about 40-50 helper lipid/about 5-15 neutral lipid/about 1-5 stealth lipid.

Another embodiment of the present invention provides a method of encapsulating a nucleic acid in a lipid nanoparticle host using a compound of any of formulas (I)-(IX) and a helper lipid, for example cholesterol, in a lipid molar ratio of about 43-47 compound of any of formulas (I)-(IX)/about 43-47 helper lipid. Another embodiment provides a method using a compound of any of formulas (I)-(IX), a helper lipid, for example cholesterol, and a neutral lipid, for example DSPC in a lipid molar ratio of about 43-47 compound of any of formulas (I)-(IX)/about 43-47 helper lipid/about 7-12 neutral lipid. Another embodiment provides a method using a compound of any of formulas (I)-(IX), a helper lipid, for example cholesterol, a neutral lipid, for example DSPC, and a stealth lipid, for example S010, S024, S027, S031, or S033 in a lipid molar ratio of about 43-47 compound of any of formulas (I)-(IX)/about 43-47 helper lipid/about 7-12 neutral lipid/about 1-4 stealth lipid.

Another embodiment of the present invention provides a method of encapsulating a nucleic acid in a lipid nanoparticle host using a compound of any of formulas (I)-(IX) and a helper lipid, for example cholesterol, in a lipid molar ratio of about 45% compound of any of formulas (I)-(IX) and about 44% helper lipid. Another embodiment provides a method using a compound of any of formulas (I)-(IX), a helper lipid, for example cholesterol, and a neutral lipid, for example DSPC in a lipid molar ratio of about 45% compound of any of formulas (I)-(IX), about 44% helper lipid, and about 9% neutral lipid. Another embodiment provides a method using a compound of any of formulas (I)-(IX), a helper lipid, for example cholesterol, a neutral lipid, for example DSPC, and a stealth lipid, for example S010, S024, S027, S031, or S033 in a lipid molar ratio of about 45% compound of any of formulas (I)-(IX), about 44% helper lipid, about 9% neutral lipid, and about 2% stealth lipid.

The ratio of lipids:nucleic acid (e.g. siRNA) in the processes of the invention may be approximately 15-20:1 (wt/wt). In certain embodiments, the ratio of lipids:nucleic acid is about 17-19:1. In other embodiments, the ratio of lipids:nucleic acid is about 18.5:1

The nanoparticles produced by the processes of the invention have an average/mean diameter and a distribution of sizes around the average value. A narrower range of particle sizes corresponds to a more uniform distribution of particle sizes. Particle size may be determined at the time of collection of the nanoparticles, after an incubation time, or after fully processing (e.g., dilution, filtration, dialysis, etc) a nanoparticle formulation. For example, particle size determination is typically done after a 60 min incubation period and/or after full sample processing. Average particle sizes are reported as either a Z-Average or a number average. Z-Averages are measured by dynamic light scattering on a Malvern Zetasizer. The nanoparticle sample is diluted in phosphate buffered saline (PBS) so that the count rate is approximately 200-400 kcts. The data is presented as a weighted average of the intensity measure. Dynamic light scattering also provides a polydispersity index (PDI) that quantifies the width of the particle size distribution. A larger PDI correlates with a larger particle size distribution and vice versa. Number averages, on the other hand, can be determined by measurement under a microscope.

In some embodiments, the encapsulated nucleic acid nanoparticles produced by the processes of the invention have an average diameter of about 30 to about 150 nm. In other embodiments, the particles have an average diameter of about 30 to about 40 nm. In other embodiments, the particles have an average diameter of about 40 to about 70 nm. In other embodiments, the particles have an average diameter of about 65 to about 80 nm. In other embodiments, the particles have a Z-average of about 50 to about 80 nm and/or a number average of about 40 to about 80 nm. In still other embodiments, the particles have a Z-average of about 50 to about 70 nm and/or a number average of about 40 to about 65 nm. In yet other embodiments, the particles have a Z-average of about 70 to about 80 nm and/or a number average of about 60 to about 80 nm. The particular size of the particles obtained may depend on the linear velocity of the nucleic acid and lipid streams, the use of an optional dilution step, and the particular nucleic acid or lipids used. Greater linear velocities and maintaining the organic solvent concentration in the first outlet solution <33% tend to produce smaller particle sizes.

In some embodiments, the encapsulated siRNA nanoparticles produced by the processes of the invention have an average diameter of about 30 to about 150 nm. In other embodiments, the particles have an average diameter of about 30 to about 40 nm. In other embodiments, the particles have an average diameter of about 40 to about 70 nm. In other embodiments, the particles have an average diameter of about 65 to about 80 nm. In other embodiments, the particles have a Z-average of about 50 to about 80 nm and/or a number average of about 40 to about 80 nm. In still other embodiments, the particles have a Z-average of about 50 to about 70 nm and/or a number average of about 40 to about 65 nm. In yet other embodiments, the particles have a Z-average of about 70 to about 80 nm and/or a number average of about 60 to about 80 nm. In still other embodiments, encapsulated siRNA nanoparticles produced by the processes of the invention may have average diameters of about 30, about 35, about 40, about 45, about 50, about 55, about 60, about 65, about 70, about 75, or about 80 nm.

Using dynamic light scattering (e.g., Malvern Zetasizer NanoZS), the polydispersity index (PDI) may range from 0 to 1.0. In certain preferred embodiments, the PDI is less than about 0.2. In other preferred embodiments, the PDI is less than about 0.1.

The processes of the present invention may be further optimized by one skilled in the art by combining cationic lipids with the desired pKa range, stealth lipids, helper lipids, and neutral lipids into formulations, including, e.g., liposome formulations, lipid nanoparticles (LNP) formulations, and the like for delivery to specific cells and tissues in vivo. In one embodiment, further optimization is obtained by adjusting the lipid molar ratio between these various types of lipids. In one embodiment, further optimization is obtained by adjusting one or more of: the desired particle size, N/P ratio, and/or process parameters. The various optimization techniques known to those of skill in the art pertaining to the above listed embodiments are considered as part of this invention.

5.0 Processes for Encapsulating a Nucleic Acid in a Lipid Nanoparticle Host

The following methods can be used to make lipid nanoparticles of the invention. To achieve size reduction and/or to increase the homogeneity of size in the particles, the skilled person may use the method steps set out below, experimenting with different combinations. Additionally, the skilled person could employ sonication, filtration or other sizing techniques which are used in liposomal formulations.

The process for making a composition of the invention typically comprises providing an aqueous solution, such as citrate buffer, comprising a nucleic acid in a first reservoir, providing a second reservoir comprising an organic solution, such as an organic alcohol, for example ethanol, of the lipid(s) and then mixing the aqueous solution with the organic lipid solution. The first reservoir is optionally in fluid communication with the second reservoir. The mixing step is optionally followed by an incubation step, a filtration or dialysis step, and a dilution and/or concentration step. The incubation step comprises allowing the solution from the mixing step to stand in a vessel for about 0 to about 24 hours (preferably about 1 hour) at about room temperature and optionally protected from light. In one embodiment, a dilution step follows the incubation step. The dilution step may involve dilution with aqueous buffer (e.g. citrate buffer or pure water) e.g., using a pumping apparatus (e.g. a peristaltic pump). The filtration step may be ultrafiltration or dialysis. Ultrafiltration comprises concentration of the diluted solution followed by diafiltration, e.g., using a suitable pumping system (e.g. pumping apparatus such as a peristaltic pump or equivalent thereof) in conjunction with a suitable ultrafiltration membrane (e.g. GE Hollow fiber cartridges or equivalent). Dialysis comprises solvent (buffer) exchange through a suitable membrane (e.g. 10,000 mwc snakeskin membrane).

In one embodiment, the mixing step provides a clear single phase.

In one embodiment, after the mixing step, the organic solvent is removed to provide a suspension of particles, wherein the nucleic acid is encapsulated by the lipid(s).

The selection of an organic solvent will typically involve consideration of solvent polarity and the ease with which the solvent can be removed at the later stages of particle formation. The organic solvent, which is also used as a solubilizing agent, is preferably in an amount sufficient to provide a clear single phase mixture of nucleic acid and lipids. Suitable organic solvents include those described by Strickley, *Pharmaceutical Res.* (2004), 21, 201-230 for use as co-solvents for injectable formulations. For example, the organic solvent may be selected from one or more (e.g. two) of ethanol, propylene glycol, polyethylene glycol 300, polyethylene glycol 400, glycerin, dimethylacetamide (DMA), N-methyl-2-pyrrolidone (NMP), and dimethylsulfoxide (DMSO). Preferably, the organic solvent is ethanol.

There is herein disclosed an apparatus for making a composition of the present invention. The apparatus typically includes at least one reservoir for holding an aqueous solution comprising a nucleic acid and another one or more reservoirs for holding an organic lipid solution. The apparatus also typically includes a pump mechanism configured to pump the aqueous and the organic lipid solutions into a mixing region or mixing chamber. In some embodiments, the mixing region or mixing chamber comprises a cross coupling, or equivalent thereof, which allows the aqueous and organic fluid streams to combine as input into the cross connector and the resulting combined aqueous and organic solutions to exit out of the cross connector into a collection reservoir or equivalent thereof. In other embodiments, the mixing region or mixing chamber comprises a T coupling or equivalent thereof, which allows the aqueous and organic fluid streams to combine as input into the T connector and the resulting combined aqueous and organic solutions to exit out of the T connector into a collection reservoir or equivalent thereof.

The processes according to the present invention may be better understood by reference to FIG. 2, which illustrates a system for use in exemplary methods of forming encapsulated nucleic acid nanoparticles. The apparatus 1 contains a cross 16 having passages 12, 22, and 32 for receiving, respectively, a first nucleic acid stream 10, a second nucleic acid stream 20, and a lipid stream 30. The streams 10, 20, and 30 may be delivered to the passages 12, 22, and 32 by pumping the respective streams through a suitable tubing leading from one or more reservoirs containing a nucleic acid solution and one or more reservoirs containing a solution of lipids (tubing and reservoirs not shown). The passages 12, 22, and 32 in FIG. 2 have approximately equal inner diameters. The streams 10, 20, and 30 meet at the intersection point 14 to form a combined stream 40. Because of the geometry of cross 16, the lipid stream 30 flows in a direction orthogonal to the nucleic acid streams 10 and 20, which flow in opposing directions at about 180° relative to each other toward the intersection point 14. The combined stream 40 flows through passage 42 into a process chamber 70, the body of which (72) may have a larger diameter than the passage 42. The process chamber 70 may also have various lengths. For example, the process chamber 70 may have a length about 100-2000 times the diameter of the passages 12, 22, and 32 and a diameter about 4 times the diameter of the passages 12, 22, and 32.

In the embodiment of FIG. 2, the joined stream 40 intersects with a dilution stream 50 entering through passage 52. The dilution stream 50 may be delivered through a tubing from a dilution reservoir containing a dilution solution. In FIG. 2, passage 52 has about 2-fold larger diameter than the passages 12, 22, and 32. The joined stream 40 and the dilution stream 50 intersect in T chamber 54. The stream produced by the intersection of joined stream 40 and dilution stream 50 is the first outlet solution 60 containing encapsulated nucleic acid nanoparticles.

In certain embodiments, the concentration of nucleic acid in the one or more nucleic acid streams is about 0.1 to about 1.5 mg/mL and the concentration of lipids in the one or more lipid streams is about 10 to about 25 mg/mL. In other embodiments, the concentration of nucleic acid in the one or more nucleic acid streams is about 0.2 to about 0.9 mg/mL and the concentration of lipids in the one or more lipid streams is about 15 to about 20 mg/mL. In other embodiments, the concentration of nucleic acid in the one or more nucleic acid streams is from about 0.225, 0.3, 0.33, or 0.45 to about 0.675 mg/mL, and the concentration of lipids in the one or more lipid streams is about 16-18 mg/mL. In other embodiments, the concentration of nucleic acid in the one or more nucleic acid streams is about 0.225, 0.3, 0.33, 0.45, or 0.675 mg/mL and the concentration of lipids in the one or more lipid streams is about 16.7 mg/mL.

The lipid streams comprise a mixture of one or more lipids in an organic solvent. The one or more lipids may be a mixture of a cationic lipid, a neutral lipid, a helper lipid, and a stealth lipid, each of which may be present in about the same relative amounts as described elsewhere hereinabove for the final encapsulated nucleic acid nanoparticle. The organic solvent used in the lipid stream is one capable of solubilizing the lipids and that is also miscible with aqueous media. Suitable organic solvents include ethanol, propylene glycol, polyethylene glycol 300, polyethylene glycol 400, glycerin, dimethylacetamide (DMA), N-methyl-2-pyrrolidone (NMP), and dimethylsulfoxide (DMSO). Preferably the organic solvent comprises about 80% or more ethanol. Preferably, the organic solvent comprises about 90% or more ethanol. More preferably, the organic solvent is ethanol. In certain embodiments, the lipid stream comprises an optional buffer solution, such as a buffer solution of sodium citrate (e.g., 25 mM).

The nucleic acid stream comprises a mixture of a suitable nucleic acid in a first aqueous solution. The first aqueous solution may include no salts or at least one salt. For example, the first aqueous solution may include a suitable nucleic acid in deionized or distilled water without an added salt. In certain embodiments, the first aqueous solution is a first buffer solution that includes at least one salt such as, for example sodium chloride and/or sodium citrate. In the first aqueous solution, sodium chloride may be present in concentrations ranging from about 0 to about 300 mM. In certain embodiments, the concentration of sodium chloride is about 50, 66, 75, 100, or 150 mM. The first aqueous solution may include sodium citrate in a concentration of about 0 mM to about 100 mM. The first buffer solution preferably has a pH of about 4 to about 6.5, more preferably about 4.5-5.5. In some embodiments, the pH of the first buffer solution is about 5 and the sodium citrate concentration is about 25 mM. In other embodiments, the pH of the first buffer solution is about 6 and the concentration of sodium citrate is about 100 mM. Preferably, the first buffer solution has a pH that is less than the pKa of the cationic lipid. For the embodiments of the invention that include no salt in the aqueous solution, the lipid stream includes the optional buffer solution. In the absence of a salt (e.g., sodium citrate) in either the nucleic acid stream or lipid stream, no encapsulation occurs.

Other possible buffers include, but are not limited to, sodium acetate/acetic acid, $Na_2HPO_4$/citric acid, potassium hydrogen phthalate/sodium hydroxide, disodium hydrogen phthalate/sodium dihydrogen orthophosphate, dipotassium hydrogen phthalate/potassium dihydrogen orthophosphate, potassium dihydrogen orthophosphate/sodium hydroxide.

In certain embodiments, the organic solvent comprises ethanol and the first outlet solution comprises about 20-25% ethanol, about 0.15-0.25 mg/mL nucleic acid, and about 3-4.5 mg/mL lipids. In other embodiments, the organic solvent comprises ethanol and the first outlet solution comprises about 20% ethanol, about 0.15-0.2 mg/mL nucleic acid, and about 3-3.5 mg/mL lipids. In yet other embodiments, the organic solvent comprises ethanol and the first outlet solution comprises about 20% ethanol, about 0.18 mg/mL nucleic acid, and about 3.3 mg/mL lipids. In other embodiments, the organic solvent comprises ethanol and the first outlet solution comprises about 25% ethanol, about 0.2-0.25 mg/mL nucleic acid, and about 4-4.5 mg/mL lipids. In still other embodiments, the organic solvent comprises ethanol and the first outlet solution comprises about 25% ethanol, about 0.23 mg/mL nucleic acid, and about 4.2 mg/mL lipids.

In certain embodiments according to FIG. 2, the nucleic acid streams 10 and 20 have a combined linear velocity of about 3 to about 8 meters/second, the lipid stream 30 has a linear velocity of about 1.5 to about 4.5 meters per second, the ratio by mass of lipids:nucleic acid is about 15-20:1, and the concentration of organic solvent in the outlet solution 60 is less than 33%. In particular embodiments, the mass ratio of lipids:nucleic acid is about 15-20:1 or about 17-19:1 and the concentration of the organic solvent in the outlet solution 60 is about 20-25%. In other particular embodiments, the mass ratio of lipids:nucleic acid is about 18.5:1 and the concentration of the organic solvent in the outlet solution 60 is about 25%. It is understood that the selection of linear velocities for the nucleic acid streams and lipid stream from the above ranges is confined by the requirement to maintain the ratio of lipids to nucleic acid as defined herein. Thus, adjustment of other parameters (e.g., nucleic acid concentration (mg/mL)), flow rate (mL/min) may be necessary to achieve the targeted lipid to nucleic acid ratio.

In other embodiments according to FIG. 2, the nucleic acid streams 10 and 20 have a combined linear velocity of about 6 to about 8 meters/second, the lipid stream 30 has a linear velocity of about 3 to about 4 meters per second, the ratio by mass of lipids:nucleic acid is about 15-20:1, and the concentration of organic solvent in the outlet solution 60 is less than 33%. In particular embodiments, the mass ratio of lipids:nucleic acid is about 15-20:1 or about 17-19:1 and the concentration of the organic solvent in the outlet solution 60 is about 20-25%. In other particular embodiments, the mass ratio of lipids:nucleic acid is about 18.5:1 and the concentration of the organic solvent in the outlet solution 60 is about 25%.

In one embodiment according to FIG. 2, the nucleic acid streams 10 and 20 have a combined linear velocity of about 6.8 meters/second, the lipid stream 30 has a linear velocity of about 3.4 meters per second, each stream 10/20/30/50 has about the same flow rate (mL/min), the ratio by mass of lipids:nucleic acid is about 15-20:1, and the concentration of organic solvent in the outlet solution 60 is about 25%. By providing about equal volumes of two nucleic streams, one lipid stream and one dilution stream, the total concentration of organic solvent derived from the lipid stream (lipid in 100% organic solvent) in the first outlet solution is about 25%. In particular embodiments, the mass ratio of lipids:nucleic acid is about 17-19:1. In other particular embodiments, the mass ratio of lipids:nucleic acid is about 18.5:1.

In typical embodiments of the invention, each nucleic acid stream 10/20 may have a nucleic acid concentration of about 0.45 mg/mL and a linear velocity of 3.4 meters/second, the lipid stream 30 may have a total lipid concentration of about 16.7 mg/mL and a linear velocity of about 3.4 meters/second, and the flow rates of the individual streams are about equal. For example, the passages 12, 22, and 32 may have inner diameters of 0.5 mm and the streams 10, 20, and 30 each have a flow rate of about 40 mL/min and a corresponding linear velocity of about 3.4 meters/second. Alternatively, the passages 12, 22, and 32 may have inner diameters of 1.0 mm and the streams 10, 20, and 30 each have a flow rate of about 160 mL/min while the corresponding linear velocities remain about 3.4 meters/second. In a further alternative, the passages 12, 22, and 32 may have inner diameters of about 2.0 mm and the streams 10, 20, and 30 each have a flow rate of about 640 mL/min, while the linear velocities remain about 3.4 meters/second. As is evident from the foregoing examples, a doubling in the diameter of the passageway and stream requires a 4-fold increase in flow rate to maintain a constant linear velocity.

In these examples, the dilution stream 50 has the same flow rate as the streams 10, 20, and 30, although the 2-fold greater diameter of the passage 52 results in a 50% lower linear velocity for the dilution stream at each process scale. It has surprisingly been found that the process of the invention may be scaled as described above while retaining the same high degree of nucleic acid encapsulation and small and uniform particle sizes.

The linear velocity of the combined nucleic acid streams 10/20 relative to the lipid stream 30 is related to the concentrations of nucleic acid and lipids in the respective streams and the flow rates (mL/min) of the individual streams, including the dilution stream 50. The concentrations of nucleic acid and lipids are not, however, limited to the specific values given above and may be adjusted up or down, provided that the flow rates are correspondingly adjusted, as needed, to generally maintain the ratio of lipids:nucleic acid about 15-20:1. For example, a 10% decrease in concentration of nucleic acid from 0.45 mg/mL to 0.405 mg/mL would be accompanied by about 1.11-fold increase in flow rate (mL/min) to keep the overall delivery of nucleic acid constant. Keeping the diameter of the nucleic acid streams constant, the 1.11-fold increase in flow rate in mL/min also results in a 1.11-fold increase in linear velocity in meters/second. Also keeping the dilution stream flow rate constant, the overall concentration of organic solvent from the lipid stream in the outlet solution 60 would decrease to about 23.5%. Of course, the flow rate of the dilution stream 50 could likewise be lowered to keep the organic solvent concentration about 25%, if so desired. Eventually, a sufficient reduction in nucleic acid concentration and corresponding increase in nucleic acid stream flow rate may obviate the necessity of the dilution stream 50 to maintain the organic solvent concentration about 25% in the first outlet solution 60. Conversely, the nucleic acid concentration may be increased (e.g., to 0.9 mg/mL). Such a two-fold increase, however, would require a corresponding decrease in nucleic acid stream flow rate(s) and increase in dilution stream rate to keep the concentration of organic solvent about 25% and the ratio of lipids:nucleic acid about 15-20:1. Further variations in nucleic acid or lipid concentration, flow rates, or linear velocities of streams 10, 20, 30, and 50 may be made in accordance with the foregoing principles.

In other embodiments of the invention, the flow rates and/or linear velocities of the nucleic acid streams 10/20 and the lipid stream 30 may both be lowered or raised together. Thus, keeping a constant diameter and concentration for each stream, the linear velocities of the combined nucleic acid streams may be reduced to 3.4 meters/second and the lipid stream to 1.7 meters/second. In other embodiments, the velocity of the combined nucleic acid streams may be reduced to about 3 meters/second and the lipid stream to about 1.5 meter/second. Likewise, the velocity of the combined nucleic acid streams may be raised to about 14 meters/second and the lipid stream to about 7 meters/second. Generally, the upper range of velocity is subject only to the mechanical limitations of the equipment used to pump the streams. Very high flow rates/velocities may result in back pressure that causes equipment failure. In general, the velocity of the combined nucleic acid streams according to FIG. 2 may range from about 3 meters/second to about 14 meters per second and for the lipid stream from about 1.5 to about 4.5 meters/second. Preferably, the velocity of the combined nucleic acid stream is from about 6-8 meters/second and for the lipid stream about 3-4 meters/second. In certain embodiments, the combined velocity of the combined nucleic acid streams is about 6.8 meters/second and for the lipid stream about 3.4 meters/second.

In some embodiments of the invention, the concentrations of the nucleic acid and the lipids may both be lowered or raised together. For example, although it is generally desirable to keep concentrations as high as possible for a more efficient process, it is possible to lower the concentrations of the nucleic acid to about 0.045 mg/mL and the lipids to about 1.67 mg/mL. At still lower concentrations, however, particle aggregation tends to increase.

In certain embodiments according to FIG. 2, the concentration of nucleic acid in the one or more nucleic acid streams is about 0.1 to about 1.5 mg/mL and the concentration of lipids in the one or more lipid streams is about 10 to about 25 mg/mL. In other embodiments, the concentration of nucleic acid in the one or more nucleic acid streams is about 0.2 to about 0.9 mg/mL and the concentration of lipids in the one or more lipid streams is about 15 to about 20 mg/mL. In other embodiments, the concentration of nucleic acid in the one or more nucleic acid streams is from about 0.225, 0.3, 0.33, or 0.45 to about 0.675 mg/mL, and the concentration of lipids in the one or more lipid streams is about 16-18 mg/mL. In other embodiments, the concentration of nucleic acid in the one or more nucleic acid streams is about 0.225, 0.3, 0.33, 0.45, or 0.675 mg/mL and the concentration of lipids in the one or more lipid streams is about 16.7 mg/mL. Generally, higher nucleic acid concentrations require a correspondingly increased level of dilution from the dilution stream 50 to maintain the nucleic acid concentration in the first outlet stream 60 in a preferred range (e.g., about 0.15-0.25 mg/mL).

In other embodiments, the T junction 54 in FIG. 2 may be replaced with a cross 54a (FIG. 2a) such that two dilution streams 50a and 50b may intersect with the joined stream (e.g., stream 40). The dilution streams 50a and 50b enter through passages 52a and 52b of the cross 54a. Using two dilution streams rather than a single dilution stream allows for a greater dilution factor of the joined stream 40. The resulting greater dilution of the first outlet stream 60 may provide somewhat smaller particle sizes. For example, using the nucleic acid stream/lipid stream flow rates and velocities described above in connection with FIG. 2, but substituting the cross 54a from FIG. 2a, can double the volume of dilution solvent. The resulting greater dilution of the first joined stream 40 produces a first outlet stream 60 with a lower concentration of organic solvent (e.g., ethanol) from the lipid stream. For example, using the cross 54a, the organic solvent concentration in the first outlet solution may be reduced to about 20%. In other respects, the nucleic acid concentrations, lipid concentrations, flow rates, velocities, etc. may be varied using the cross 54a the same as described above in relation to FIG. 2.

Alternatively, the joined stream from any of the foregoing embodiments may simply be diluted in a dilution pool containing an equivalent volume of dilution solvent as that provided by dilution streams 50, 50a, or 50b.

Figure 3C:
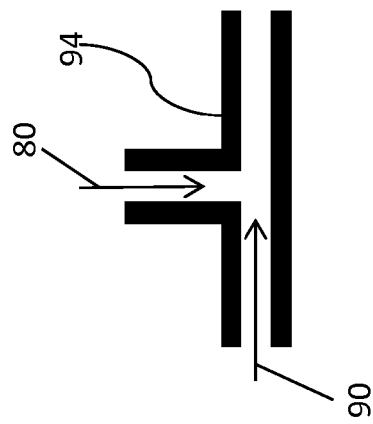
FIGS. 3a, 3b, and 3c illustrate alternate embodiments of a mixing chamber for use in the system of FIG. 2.
Figure 3B:
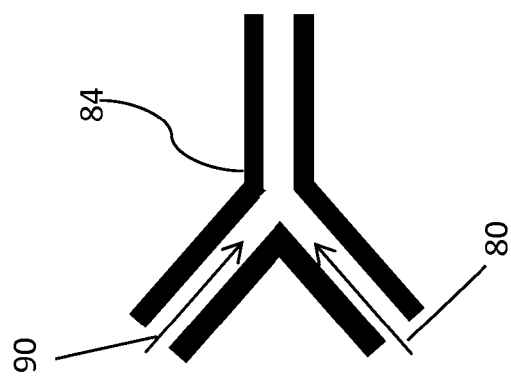
Figure 3A:
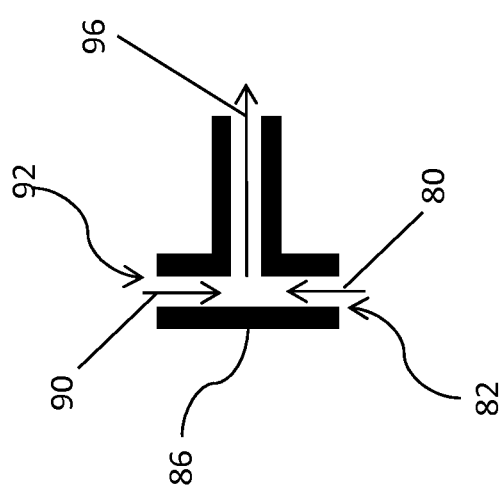

In alternative embodiments, the cross 16 in FIG. 2 may be replaced with a T-shaped chamber 86, as shown in FIG. 3a. Processes using chamber 86 have two entry passages 82 and 92 for one nucleic acid stream 80 and one lipid stream 90. In processes using the mixing chamber 86, the nucleic acid stream and the lipid stream have opposing flows at about 180° relative to each other. Using chamber 86, the flow rate and velocity of the single nucleic acid stream may be double that of the lipid stream in order to maintain the same ratio of lipid:nucleic acid that may be achieved using the cross 16, which utilizes two nucleic acid streams. For example, in one embodiment using T chamber 86 (e.g., 0.5 mm diameter passages 82 and 92) a nucleic acid stream having about 0.45 mg/mL nucleic acid may have a flow rate of about 80 mL/min and linear velocity of 6.8 meters/second and the lipid stream may have a concentration of about 16.7 mg/mL and a linear velocity of 3.4 meters/second. Employing a dilution stream 50 as shown in FIG. 2 at a flow rate of 40 mL/min in the process using chamber 86 results in a concentration of organic solvent in the first outlet solution of about 25%. Surprisingly, the same beneficial properties of small particle size and uniformity may be obtained using T chamber 86 as can be obtained using cross 16. Using T chamber 86 differs by doubling the nucleic acid stream flow rate compared to the individual nucleic acid stream flow rates in FIG. 2. The overall nucleic acid stream flow rates remain the same for both processes, therefore resulting in nanoparticles having substantially equivalent properties.

In certain embodiments using T chamber 86 and a dilution stream 50, the nucleic acid stream 80 has a linear velocity of about 3 to about 8 meters/second, the lipid stream 90 has a linear velocity of about 1.5 to about 4.5 meters per second, the ratio by mass of lipids:nucleic acid is about 15-20:1, and the concentration of organic solvent in the outlet solution is less than 33%. In particular embodiments, the mass ratio of lipids:nucleic acid is about 15-20:1 or about 17-19:1 and the concentration of the organic solvent in the outlet solution is about 20-25%. In other particular embodiments, the mass ratio of lipids:nucleic acid is about 18.5:1 and the concentration of the organic solvent in the outlet solution is about 25%.

In other embodiments using T chamber 86 and a dilution stream 50, the nucleic acid stream 80 has a linear velocity of about 6 to about 8 meters/second, the lipid stream 90 has a linear velocity of about 3 to about 4 meters per second, the ratio by mass of lipids:nucleic acid is about 15-20:1, and the concentration of organic solvent in the outlet solution is less than 33%. In particular embodiments, the mass ratio of lipids:nucleic acid is about 15-20:1 or about 17-19:1 and the concentration of the organic solvent in the outlet solution is about 20-25%. In other particular embodiments, the mass ratio of lipids:nucleic acid is about 18.5:1 and the concentration of the organic solvent in the outlet solution is about 25%.

In one embodiment using T chamber 86 and a dilution stream 50, the nucleic acid stream 80 has a linear velocity of about 6.8 meters/second, the lipid stream 90 has a linear velocity of about 3.4 meters per second, stream 80 has double the flow rate (mL/min) of stream 90 and dilution stream 50, the ratio by mass of lipids:nucleic acid is about 15-20:1, and the concentration of organic solvent in the outlet solution is about 25%. In particular embodiments, the mass ratio of lipids:nucleic acid is about 17-19:1. In other particular embodiments, the mass ratio of lipids:nucleic acid is about 18.5:1.

In certain embodiments using T chamber 86 without a dilution stream 50, the nucleic acid stream 80 has a linear velocity of about 8 to about 14 meters/second, the lipid stream 90 has a linear velocity of about 1.5 to about 4.5 meters per second, the ratio by mass of lipids:nucleic acid is about 15-20:1, and the concentration of organic solvent in the outlet solution is less than 33%. In particular embodiments, the mass ratio of lipids:nucleic acid is about 15-20:1 or about 17-19:1 and the concentration of the organic solvent in the outlet solution is about 20-25%. In other particular embodiments, the mass ratio of lipids:nucleic acid is about 18.5:1 and the concentration of the organic solvent in the outlet solution is about 20 or 25%.

In other embodiments using T chamber 86 without a dilution stream 50, the nucleic acid stream 80 has a linear velocity of about 9 to about 11 meters/second, the lipid stream 90 has a linear velocity of about 3 to about 4 meters per second, the ratio by mass of lipids:nucleic acid is about 15-20:1, and the concentration of organic solvent in the outlet solution is less than 33%. In particular embodiments, the mass ratio of lipids:nucleic acid is about 15-20:1 or about 17-19:1 and the concentration of the organic solvent in the outlet solution is about 20-25%. In other particular embodiments, the mass ratio of lipids:nucleic acid is about 18.5:1 and the concentration of the organic solvent in the outlet solution is about 25%.

In one embodiment using T chamber 86 without a dilution stream 50, the nucleic acid stream 80 has a linear velocity of about 10.2 meters/second, the lipid stream 90 has a linear velocity of about 3.4 meters per second, stream 80 has triple the flow rate (mL/min) of stream 90, the ratio by mass of lipids:nucleic acid is about 15-20:1, and the concentration of organic solvent in the outlet solution is about 25%. In particular embodiments, the mass ratio of lipids:nucleic acid is about 17-19:1. In other particular embodiments, the mass ratio of lipids:nucleic acid is about 18.5:1.

In other embodiments using T chamber 86 without a dilution stream 50, the nucleic acid stream 80 has a linear velocity of about 11 to about 14 meters/second, the lipid stream 90 has a linear velocity of about 3 to about 4 meters per second, the ratio by mass of lipids:nucleic acid is about 15-20:1, and the concentration of organic solvent in the outlet solution is less than 33%. In particular embodiments, the mass ratio of lipids:nucleic acid is about 15-20:1 or about 17-19:1 and the concentration of the organic solvent in the outlet solution is about 20-25%. In other particular embodiments, the mass ratio of lipids:nucleic acid is about 18.5:1 and the concentration of the organic solvent in the outlet solution is about 20%.

In one embodiment using T chamber 86 without a dilution stream 50, the nucleic acid stream 80 has a linear velocity of about 13.6 meters/second, the lipid stream 90 has a linear velocity of about 3.4 meters per second, stream 80 has quadruple the flow rate (mL/min) of stream 90, the ratio by mass of lipids:nucleic acid is about 15-20:1, and the concentration of organic solvent in the outlet solution is about 20%. In particular embodiments, the mass ratio of lipids:nucleic acid is about 17-19:1. In other particular embodiments, the mass ratio of lipids:nucleic acid is about 18.5:1.

As discussed above in connection with FIG. 2, the scale, concentrations, flow rates, and linear velocities of the nucleic acid stream 80 and lipid stream 90 may similarly be varied using the T chamber 86. In particular, the nucleic acid concentrations, lipid concentrations, and ethanol concentrations described hereinabove in connection with FIG. 2 also apply to embodiments of the invention employing the T chamber 86. In one exemplary embodiment, the nucleic acid concentration may be reduced by one-third (e.g., from 0.45 to 0.3 mg/mL) and the flow rate of the nucleic acid stream increased by 50% (e.g., from 80 mL/min to 120 mL/min) to maintain the same overall delivery of nucleic acid (about 36 mg/min). The linear velocity would similarly be increased to about 10.2 meters/second. Because of the greater dilution of the nucleic acid stream, a concentration of about 25% organic solvent in the outlet solution may be obtained without using a supplementary dilution stream. By further increasing the nucleic acid stream flow rate to 160 mL/min (velocity of 13.6 meters/second for 0.5 mm stream), the concentration of organic solvent in the outlet solution is reduced to about 20%. In this latter process, the velocity of the nucleic acid stream may be reduced to about 6.8 meters/second and the velocity of the lipid stream reduced to about 1.7 meters/second without significant change in the particle size and uniformity.

Although the various nucleic acid, lipid, and dilution streams in FIGS. 2 and 3 and generally described above intersect either at right angles or head-on, these angles are not critical. For example, the T chamber 86 in FIG. 3 may be replaced by a Y-shaped chamber 84 (FIG. 3b). Or alternatively, the orientation of the T chamber may be rotated as shown in chamber 94 (FIG. 3c). Although FIG. 3c shows the nucleic acid stream 80 intersecting the forward flow of the lipid stream 90, the positions of the nucleic acid and lipid streams may be reversed in FIG. 3c.

In still other embodiments, the number of nucleic acid and lipid streams may be further varied with appropriate adjustment of concentrations and flow rates. For example, with suitable equipment 2, 3, or 4 lipid streams may be joined with 1, 2, 3, or 4 nucleic acid streams.

The processes of the invention described herein provide for high rates of nucleic acid encapsulation. Generally the encapsulation rate is >70%. In some embodiments of the invention, 75% or more of the nucleic acid is encapsulated. In other embodiments, 80% or 85% of the nucleic acid is encapsulated. In still other embodiments, 90% or more of the nucleic acid is encapsulated. In other embodiments about 91, about 92, about 93, about 94, about 95, about 96, about 97, about 98, about 99, or about 100 of the nucleic acid is encapsulated.

Following formation of the encapsulated nucleic acid nanoparticles as described herein, the first outlet solution may be incubated for about 60 minutes at room temperature. After incubation, the solution may be mixed with a second dilution solvent to dilute the first outlet solution by about 2-fold to provide a second outlet solution. The second dilution solvent may be a third buffer solution or water. The dilution step may be carried out by mixing the incubated first outlet solution with the second dilution solvent (water) in a T connector like the T chamber 86 in FIG. 3a. The incubated first outlet solution and the second dilution solvent may be supplied to the T connector at any suitable flow rate or velocity, such as, for example, about 0.5 to 1 meter/second. Following the dilution step, the concentration of organic solvent in the second outlet solution is reduced by one-half relative to the first outlet solution. Thus, in some embodiments, the concentration of organic solvent (e.g., ethanol) in the second outlet solution is less than 16.5%. In other embodiments, the concentration of organic solvent (e.g., ethanol) in the second outlet solution is about 10-15%, about 10-12.5%, about 12.5%, or about 10%. The second outlet solution may be concentrated by tangential flow filtration and subjected to a 15× diafiltration with phosphate buffered saline (PBS) to remove the starting buffer and ethanol, which are replaced with PBS. After tangential flow filtration, the pool of concentrated encapsulated nucleic acid nanoparticles in PBS may be collected and sterile filtered as described in more detail in the Examples below. Encapsulated nucleic acid nanoparticles present in formulations produced by the foregoing additional process steps may be storage stable at 4° C. for greater than 6 months.

According to each of the embodiments disclosed herein, are further embodiments where the nucleic acid is an siRNA. For example, according to the embodiments described herein are further embodiments where the nucleic stream is an siRNA stream comprising a mixture of one or more siRNA molecules in a buffer solution and having the linear velocities disclosed herein.

6.0 Process Examples

6.1 siRNA Lipid Formulations

The encapsulated siRNA lipid nanoparticles were formed by mixing solutions of lipids dissolved in ethanol with siRNA dissolved in a citrate buffer by the systems and apparatus generally shown in FIGS. 2-3b, and described generally above. Mixing chambers were used having passages with inner diameters of 0.5, 1.0, or 2.0 mm. The processing chambers had lengths of from 50 mm to 1000 mm. The dilution chambers had passages with inner diameters equivalent to or of at least to 2 times that of the mixing chamber about 0.5 or 1.0 or 2.0 or 4.0 mm. The lipid solution contained a cationic lipid, a helper lipid (cholesterol), a neutral lipid (DSPC) and a stealth lipid.

The concentrations of total lipids were either 16.7 mg/mL or 25 mg/mL. The total lipid to siRNA ratio for these experiments was about 18.3:1. The concentration of siRNA solutions were 0.225, 0.3, 0.3375, or 0.45 mg/mL in a sodium citrate:sodium chloride buffer with pH 5. The concentration of NaCl was 50 mM, 66 mM, 75 mM, or 100 mM. The flow rates and linear velocities were varied as described below.

For siRNA encapsulation experiments, the cationic lipids and stealth lipids (i.e., PEG lipid) used are shown in the Table below.

6.2 Process Example 1 Encapsulation of siRNA

6.2.1 Preparation of Lipid Mixture in Ethanol

The following is an example of siRNA encapsulated at a cationic lipid amine to siRNA phosphate (N:P) molar ratio of 4.5:1. Lipids (cationic lipid, DSPC, cholesterol and lipidated PEG) in the amounts shown in Table 4 are dissolved in 150 mL of ethanol. The molar ratios of lipids are 45:9:44:2, respectively. The mixture is sonicated briefly, then gently agitated for 5 minutes and then maintained at 37° C. until use.

TABLE 4

| Lipid mixture components | | | |
|---|---|---|---|
| Reagent | Amount (mg) | MW | Final Concentration (mM) |
| Cationic lipid A1 | 1315.9 | 732.15 | 12 |
| DSPC | 284 | 790.16 | 2.4 |
| Cholesterol | 679.5 | 386.67 | 11.7 |
| PEG lipid B1 | 226.6 | 2837 | 0.53 |

6.2.2 Preparation of siRNA SEQ ID NO. 1 in Citrate Buffer

The buffer for the siRNA streams is 100 mM sodium chloride and 25 mM sodium citrate at a pH of 5. The pH of the citrate buffer is first confirmed to be pH 5.00. If it is not, the pH is adjusted before proceeding. Enough siRNA in water for the encapsulation is thawed from −80° C. storage. The siRNA SEQ ID NO. 1 is added to citrate buffer solution and the concentration of the dissolved siRNA is measured by

TABLE 2

| lipid ID | lipid type | Chemical name |
|---|---|---|
| A1 | cationic lipid | ((5-((dimethylamino)methyl)-1,3-phenylene)bis(oxy))bis(octane-8,1-diyl) bis(decanoate) |
| A2 | cationic lipid | (9Z,9'Z,12Z,12'Z)-2-((4-(((3-(dimethylamino)propoxy)carbonyl)oxy)hexadecanoyl)oxy)propane-1,3-diyl bis(octadeca-9,12-dienoate) |
| A3 | cationic lipid | (9Z,12Z)-3-((4,4-bis(octyloxy)butanoyl)noxy)-2-((((3-(diethylamino)propoxy)carbonyl)oxy)methyl)propyl octadeca-9,12-dienoate |
| A4 | cationic lipid | (9Z,9'Z,12Z,12'Z)-((5-((dimethylamino)methyl)-1,3-phenylene)bis(oxy))bis(butane-4,1-diyl) bis(octadeca-9,12-dienoate) |
| B1 | PEG lipid | PEG-dimyristylglycerol |
| B2 | PEG lipid | 2,3-bis(tetradecyloxy)propyl (158-hydroxy-3,6,9,12,15,18,21,24,27,30,33,36,39,42,45,48,51,54,57,60,63,66,69,72,75,78,81,84,87,90,93,96,99,102,105,108,111,114,117,120,123,126,129,132,135,138,141,144,147,150,153,156-dopentacontaoxaoctapentacontahectyl)carbamate |

The siRNA used for these experiments had sequences and SEQ ID NOs. as shown in Table below.

optical density at 260 nm in a UV spectrophotometer. The final concentration of the siRNA is adjusted to 0.45 mg/ml

TABLE 3

| Position | Location | Antisense generic sequence | Sense generic sequence | Gene |
|---|---|---|---|---|
| 457 | 3'UTR | AGCACTGAGAATACTGTC (SEQ ID NO: 1) | GACAGTATTCTCAGTGCT (SEQ ID NO: 7) | APOC3 |
| 524 | 3'UTR | TTCTTGTCCAGCTTTATT (SEQ ID NO: 2) | AATAAAGCTGGACAAGAA (SEQ ID NO: 8) | APOC3 |
| 72 | CDS | ACAACAAGGAGTACCCGG (SEQ ID NO: 3) | CCGGGTACTCCTTGTTGT (SEQ ID NO: 9) | APOC3 |
| | | UUuAAUUGAAACcAAGAcAuu (SEQ ID NO: 4) | uGucuuGGuuucAAuuAAAuu (SEQ ID NO: 10) | FVII |
| | | UCAuGAAAucGuuAcGuuGuu (SEQ ID NO: 5) | CAACGuAACGAuuuCAuGAuu (SEQ ID NO: 11) | EPAS1 | in 150 ml of citrate buffer in a sterile PETG bottle and is held at room temperature until use.

6.2.3 Encapsulation of siRNA in Lipid Nanoparticles

The siRNA encapsulation is carried out using a system as shown generally in FIG. 2. Sterile syringes are loaded with an equal volume (25 ml) of lipids in ethanol (syringe (a)), siRNA in citrate buffer (syringes (b1) and (b2)), and water alone (syringe (c)). Tubing leading from Luer fittings on the syringe (a) containing 16.7 mg/mL lipids is attached to the center input of a cross junction with a 0.5 mm inner diameter. Tubing leading from Luer fittings on syringes (b1) and (b2) containing siRNA at 0.45 mg/ml are attached to the side inputs of the cross junction. The tubing is fluorinated ethylene propylene (FEP) tubing with 1.55 mm inner diameter. Syringes (a), (b1) and (b2) are installed on syringe pump A. Tubing leading from the center input of the cross opposite the lipid input is attached to a T junction with a 1 mm inner diameter (see e.g., FIG. 2, T junction 54). Tubing leading from a Luer fitting on syringe (c) containing water alone is attached to the T junction to enable in-line dilution of siRNA lipid nanoparticles, and syringe (c) is installed on syringe pump B. Have the output line from the T junction positioned over a sterile PETG bottle for collection of the diluted siRNA lipid nanoparticles. It is important to make sure that all fittings are tight on the syringes. The syringe pumps are set to the appropriate syringe manufacturer and size and a flow rate of 40 ml per minute. Start both pumps simultaneously, and start collecting material after approximately 0.5 seconds. Approximately 90 ml of encapsulated siRNA lipid nanoparticles will be collected and which contains 25% ethanol by volume, 0.23 mg/mL of the siRNA, 4.2 mg/mL of the lipids, and 50 mM NaCl. After a 60 min. post mixing incubation period, particle sizes are determined using a Malvern Zetasizer.

6.2.4 Dilution of siRNA Lipid Nanoparticles

A 1.0 mm inner diameter T junction is set up for further dilution of the siRNA lipid nanoparticle suspension. This dilution step is run with two syringes on one syringe pump. One 140 mL syringe contains the siRNA lipid nanoparticles and a second 140 mL syringe contains water. The flow rate is set to 25 ml per minute. The siRNA stream and the water stream enter the T junction at 180 degrees from each other. The diluted siRNA lipid nanoparticle suspension is collected into a sterile PETG bottle. The final volume will be approximately 280 ml, with an ethanol concentration of 12.5%.

6.2.5 Dialysis and Concentration of siRNA Lipid Nanoparticles by Tangential Flow Filtration For every 50 mg of siRNA in the encapsulation run, use a Vivaflow 50 cartridge. For a 100 mg siRNA encapsulation run, use 2 Vivaflow 50 cartridges attached in series. The regenerated cellulose cartridges must first be rinsed to remove any storage solution from the manufacturer. This is done by filling an empty TFF reservoir with 500 ml of DI water and recirculate with a peristaltic pump at a flow rate of 115 ml/min. The permeate line should not be restricted and the rinsing process is complete when the entire 500 ml of water is flushed through the membrane.

Load the siRNA lipid nanoparticle suspension into the Minimate TFF reservoir. Concentrate the mixture while maintaining an overall pressure of 20-25 psi. The filtrate should elute at approximately 4 ml per minute throughout the concentration step. This rate is achieved by restricting the permeate line with a pinch valve until the proper flow rate is achieved. Concentrate until the liquid level in the reservoir is at the 15 ml graduation. Diafilter the concentrated siRNA lipid nanoparticle suspension against 225 ml of pyrogen-free, nuclease-free 1×PBS. Increase the flow rate to 80 ml/min. After diafiltration, resume concentration of the material to the holdup volume of the TFF system. Collect the siRNA lipid nanoparticle suspension from the reservoir. It is possible to rinse the TFF system with additional 2 ml of 1×PBS and to collect this wash that contains diluted siRNA lipid nanoparticle suspension, but this wash should be collected separately from the concentrated siRNA lipid nanoparticle suspension. Store materials at 4° C. until analysis.

6.2.6 Sterile Filtration Step

The siRNA lipid nanoparticles are filtered by heating approximately 10 ml of the suspension in a glass vial which is placed in a aluminum block heater preheated to 50° C. for 10 min. The vial is then removed and the solution is removed with a syringe and filtered through a 0.22 μm PES syringe filter directly into a sterile vial. This final product is stored at 4° C.

6.2.7 Percent Encapsulation Determination (SYBR GOLD)

To determine the efficiency of the siRNA formulation into lipid nanoparticles, the percent encapsulation of the siRNA can be determined by measuring sybr gold fluorescence. When bound to siRNA, sybr gold fluoresces. The intensity of sybr gold fluorescence is proportional to the amount of siRNA.

A standard solution of siRNA stock at approximately 0.9 mg/mL is prepared in PBS. The concentration of siRNA stock is verified by UV measurement. The siRNA stock is diluted with PBS to 8 μg/mL. Serial dilution is done to prepare 4, 2, 1, 0.5 and 0.25 μg/mL siRNA solutions. 6 μg/mL of siRNA is prepared by mixing equal volumes of 8 μg/mL and 4 μg/mL solutions.

To prepare test samples, 10 μL of siRNA lipid nanoparticle suspension are diluted with 990 μL of PBS (this is now solution A). Note: This first dilution step applies for the formulations with expected siRNA concentration of ~3.6 mg/mL or less. If the concentration is higher than ~3.6 mg/mL, the dilution should be greater. 40 uL of solution A is diluted with 160 μL of PBS (this is now solution 1).

For the measurement of free siRNA in a formulation, a solution of 0.02% sybr gold in PBS is prepared (e.g., 34 of sybr gold in 15 mL of PBS) (solution 2). In a 96-well black, clear-bottom plate 10 μL of solution 1 is mixed with 190 μL of solution 2 to provide sample mixture 1. In this mix, sybr gold will bind only to the nonencapsulated (i.e. free) siRNA. It will not have access to the siRNA encapsulated in the liposome.

For the measurement of total siRNA in a formulation, a solution of 0.02% sybr gold and 0.2% triton-x in PBS is prepared (e.g., 3 μL of sybr gold in 15 mL of 0.2% triton in PBS) (solution 3). In a 96-well black, clear-bottom plate 10 μL of solution 1 is mixed with 190 μL of solution 3 to provide sample mixture 2. In this mix, triton-x disrupts the liposomes and exposes previously encapsulated siRNA to sybr gold binding. Hence, sybr gold will bind to the non-encapsulated (i.e. free) siRNA and to all newly exposed siRNA. The free siRNA+newly exposed siRNA=total siRNA The standard solutions described above (10 μL each) are mixed with either 190 μL solution 2 to provide standard mixtures 1 or 190 μL solution 3 to provide standard mixtures 2.

The fluorescence of all mixes is measured on the SpectraMax MS spectrophotometer using software SoftMax pro 5.2 and the following parameters:

$\lambda_{ex}$=485 nm $\lambda_{em}$=530 nm

Read Mode: Fluorescence, Top read

Wavelengths: Ex 485 nm, Em 530 nm, Auto Cutoff On 530 nm
Sensitivity: Readings 6, PMT: Auto
Automix: Before: Off
Autocalibrate: On
Assay plate type: 96 Well costarblk/clrbtm
Wells to read: Read entire plate
Settling time: Off
Column Way. Priority: Column priority
Carriage Speed: Normal
Auto read: Off The fluorescence intensity values obtained from standard mixtures 1 are used to create the calibration curve for free siRNA. The fluorescence intensity of a sample 1 mixture is then plugged into the equation provided by the calibration curve for free siRNA. The found concentration of the sample is then multiplied by the dilution magnitude to obtain the free siRNA in the lipid nanoparticle formulation.

The fluorescence intensity values obtained from standard mixtures 2 are used to create the calibration curve for total siRNA. The fluorescence intensity of a sample 2 mixture is then plugged into the equation provided by the calibration curve for total siRNA. The found concentration of the sample is then multiplied by the dilution magnitude to obtain the total siRNA in the lipid nanoparticle formulation.

The encapsulated siRNA is calculated by the formula: [(total siRNA−free siRNA)/(total siRNA)]×100%.

6.2.8 Percent Encapsulation Determination Using Size Exclusion Chromatography (SEC)

Because the size of free siRNA (5 nm) is different than the size of a liposome (50-200 nm), they will elute at different times in the size exclusion column. Free siRNA elutes after the liposomes. Retention time for siRNA is ~17 minutes whereas the retention time for liposomes is ~10 minutes. Detection of eluted siRNA is carried out via UV detector with absorption wavelength set at 260 nm.

siRNA stock at approximately 0.9 mg/mL is prepared in PBS. To a 200 μL aliquot of stock, 10 μL of TRITON X-100 are added. The concentration of siRNA stock is verified by UV measurement. Serial dilutions are done to prepare standards at ½, ¼, ⅛, 1/16 and 1/32 concentration of the siRNA stock. 10 μL of TRITON X-100 are added to 200 μL of each standard. The concentration of each standard is verified by UV measurement.

In a HPLC vial, 254 of lipid nanoparticle formula are added to 185 μL of 1×PBS (10×PBS (FISHER, BP399) diluted with deionized water to 1×). The dispersion is gently vortexed until homogeneous (dispersion 1). In another HPLC vial, 254 of lipid nanoparticle formula are added to 185 μL of 20% TRITON-X. The dispersion is gently vortexed until clear and homogeneous (dispersion 2).

The size exclusion chromatography is performed on an AGILENT 1200 HPLC using EMPOWER PRO software. The parameters are:
Column temperature: 30° C.
Mobile Phase rate flow: 1 ml/min for 30 minutes
UV detector wavelength: 260 nm
Injection volume: 20 uL
Number of injections: 2

20 μL of standards and dispersions are injected onto size exclusion column, mobile phase 1×PBS with pH adjusted to 7.7 flowing at 1 mL/min for 30 minutes. The eluted material is detected by UV detector with 260 nm absorption wavelength.

From the siRNA standards, the peak at ~17 minutes represents the siRNA. From dispersion 1, the peak at ~10 minutes represents the lipid nanoparticle containing encapsulated siRNA and the peak at ~17 minutes represents the nonencapsulated (i.e. free) siRNA.

In dispersion 2, TRITON-X disrupts the lipid nanoparticle enabling previously encapsulated siRNA to elute together with already free siRNA at 17 minutes. The peak at ~10 minutes disappears, and only one peak in the chromatogram remains, i.e. the peak at ~17 minutes, representing both nonencapsulated (i.e. free) siRNA and newly free siRNA. Free siRNA+newly free siRNA=total siRNA.

The peak area values obtained from siRNA standards are used to create the siRNA concentration calibration curve. The integrated area of the peak at ~17 minutes in dipersion 1 is plugged into the equation provided by calibration curve for free siRNA to obtain the concentration of the free siRNA in the dispersion. The found concentration of the sample is then multiplied by the dilution magnitude to obtain the free siRNA in the lipid nanoparticle formulation.

The integrated area of the peak at ~17 minutes in dispersion 2 is plugged into the equation provided by calibration curve for free siRNA to obtain the concentration of the total siRNA in the dispersion. The found concentration of sample is then multiplied by the dilution magnitude to obtain the total siRNA in the lipid nanoparticle formulation.

Encapsulated siRNA is calculated by formula: [(total siRNA−free siRNA)/(total siRNA)]×100%.

6.2.9 Particle Analytics

The siRNA lipid nanoparticles are analyzed for size and polydispersity using a Zetasizer Nano ZS from Malvern Instruments. For formulated siRNA at an encapsulated siRNA concentration of >1 mg/ml, dilute 5 μl of sample with 115 μl of 1×PBS. Add to a small volume disposable microcuvette. Insert the cuvette into the Zetasizer Nano ZS. For the machine settings, set material to be polystyrene latex, dispersant to be water, and cell to be ZEN040. Measure the sample at 25° C. with no wait time. Record Z-Ave (set as diameter, in nanometer units) and polydispersity index (PDI).

In Table 5 are shown the results obtained for siRNA and lipid nanoparticle combinations using the procedures described above. Encapsulation percentages were determined using the SEC method.

TABLE 5 siRNA Lipid Nanoparticle Encapsulation Results

| Cationic lipid | PEG lipid | siRNA SEQ ID NO. | Z-Ave (nm) | # Ave | PDI | % Encapsulation |
|---|---|---|---|---|---|---|
| A1 | B1 | 1 | 65.1 | 49.6 | 0.089 | 92.9 |
| A2 | B2 | 1 | 72.9 | 52.2 | 0.092 | 93.1 |
| A3 | B2 | 1 | 81.7 | 66.5 | 0.026 | 97.0 |
| A3 | B1 | 1 | 72.4 | 56.6 | 0.03 | 98.1 |
| A1 | B1 | 2 | 71.0 | 50.5 | 0.145 | 94.7 |

6.3 Process Example 2 Effect of Dilution

Using the system substantially as shown in FIG. 2, two aqueous nucleic acids streams having concentrations of 0.45 mg/mL of siRNA SEQ ID NO:1, 100 mM NaCl, and 25 mM sodium citrate at a pH of 5 were introduced from opposing directions into a cross-shaped mixing chamber having passages with inner diameters of 0.5 mm with flow rates of 40 mL/min each. Simultaneously, a lipid stream was introduced into the cross-shaped mixing chamber from a direction orthogonal to the two nucleic acid streams at a flow rate of 40 mL/min. The lipid stream was made up of 45% cationic lipid A1, 44% cholesterol, 9% DSPC, and 2% PEG-lipid B1 in ethanol. The total concentration of lipids was 16.7 mg/mL. In one run, the joined stream from the cross-shaped mixing chamber was subjected to a dilution step with water using a T-shaped chamber (1.0 mm inner diameter) analogous to chamber 54 in FIG. 2. The water was introduced into the T-shaped chamber at a rate of 40 mL/min. The resultant solution was collected and the encapsulated nucleic acid nanoparticles analyzed for size and uniformity with the results shown in entry 1 in Table 6. The solution obtained from entry 1 included 25% ethanol by volume, 0.23 mg/mL of the siRNA, 4.2 mg/mL of the lipids, and 50 mM NaCl. In a separate experiment using the same concentrations, flow rates, and initial cross-shaped mixing chamber, the joined streams from the mixing chamber were diluted in a volume of water equivalent to the dilution volume used in entry 1. These results are shown in entry 2 in Table 6. The concentrations of the collected solution were the same as in entry 1. For comparison, another experiment was conducted under the same process conditions but without any dilution step. These results are shown in entry 3 in Table 6. Without any dilution step, the collected solution in entry 3 included 33% ethanol, 0.3 mg/mL siRNA, 5.6 mg/mL lipids and 66 mM NaCl. The Z-Avg, #-Avg, and PDI for entries 1 and 2 were less than entry 3, which lacked the dilution step. The Z-Avg, #-Avg, and PDI in Table were determined 60 minutes post-mixing.

TABLE 6

| Entry | Dilution chamber | Dilution flow (mL/min) | Z-Avg | #-Avg | PDI |
|---|---|---|---|---|---|
| 1 | T | 40 | 58 | 46 | 0.063 |
| 2 | pool | — | 58 | 47 | 0.063 |
| 3 | — | — | 82 | 69 | 0.083 |

Figure 4B:
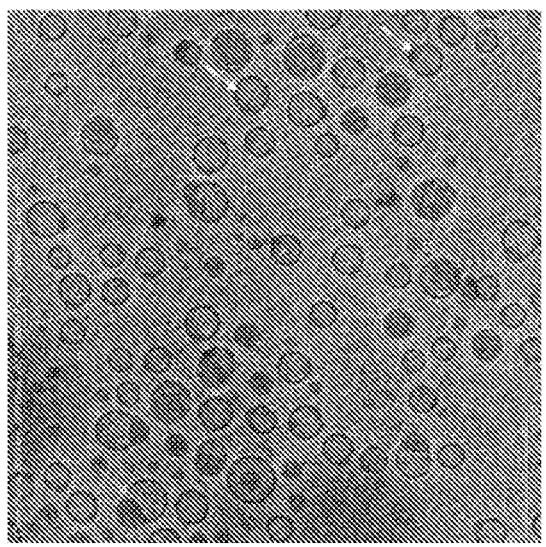
FIG. 4b is an image obtained by cryo-electron microscopy illustrating the particle uniformity for siRNA encapsulated lipid nanoparticles produced using a T-shaped mixing chamber and the process and materials as described in Process Example 2.
Figure 4A:
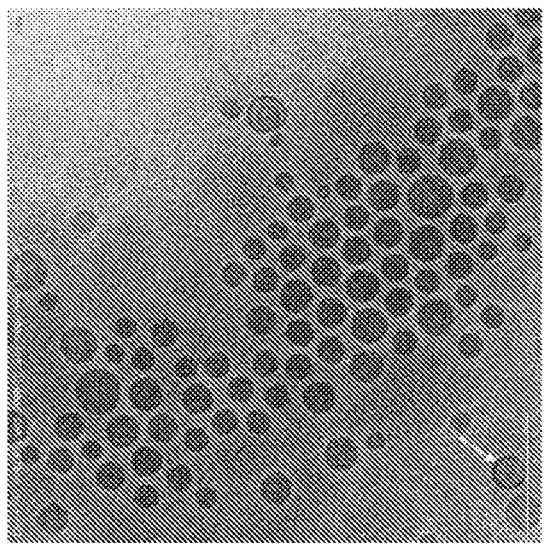
FIG. 4a is an image obtained by cryo-electron microscopy illustrating the particle uniformity for siRNA encapsulated lipid nanoparticles produced using a cross-shaped mixing chamber and the process and materials as described in Process Example 2.

Using the same process and lipid mixture as described for entry 1 in Table 6, but with siRNA SEQ ID NO. 3, the uniformly-sized lipid nanoparticles shown in FIG. 4a were produced. Replacing the cross-shaped mixing chamber with the T-shaped mixing chamber of FIG. 3a (0.5 mm inner diameter) while increasing the concentration of siRNA SEQ ID. NO. 3 to 0.9 mg/mL at a flow rate of 40 mg/mL (same total amount of siRNA in one-half the volume) produced the less uniformly-sized lipid nanoparticles shown in FIG. 4b. Analogous processes using a T-shaped mixing chamber and siRNA at 0.9 mg/mL are described in Process Example 4.

6.4 Process Example 3 Effect of Flow Rates, Velocities, and Solution Concentrations In a series of experiments using a T-shaped mixing chamber analogous to that shown in FIG. 3a and having an inner diameter of 0.5 mm, a single nucleic acid stream and a single lipid stream were mixed at various flow rates/velocities and concentrations. The nucleic acid and lipid streams included the same constituents as described above in Process Example 2. No dilution step was used in these examples since the initial siRNA concentrations were adjusted to obtain a final solution concentration the same as entry 1 in Table 6. The concentration of lipids in ethanol in these experiments was either 16.7 mg/mL (1×) or 25 mg/mL (1.5×). The results are shown in Table 7 below with the Z-Avg, #-Avg, and PDI determined 60 minutes post-mixing.

TABLE 7

| Lipid Flow (mL/min) | Lipid linear velocity (m/s) | [lipid] | Total siRNA Flow (mL/min) | siRNA linear velocity (m/s) | [siRNA] (mg/mL) | NaCl (mM) | Z-Avg | #-Avg | PDI |
|---|---|---|---|---|---|---|---|---|---|
| 40 | 3.4 | 1× | 80 | 6.8 | 0.45 | 100 | 60 | 44 | 0.089 |
| 40 | 3.4 | 1× | 120 | 10.2 | 0.3 | 66 | 58 | 46 | 0.048 |
| 40 | 3.4 | 1× | 160 | 13.6 | 0.225 | 50 | 60 | 42 | 0.110 |
| 20 | 1.7 | 1× | 60 | 5.1 | 0.3 | 66 | 59 | 47 | 0.037 |
| 20 | 1.7 | 1× | 80 | 6.8 | 0.225 | 50 | 59 | 43 | 0.100 |
| 40 | 3.4 | 1.5× | 120 | 10.2 | 0.45 | 100 | 66 | 54 | 0.032 |
| 40 | 3.4 | 1.5× | 160 | 13.6 | 0.3375 | 75 | 64 | 43 | 0.108 |
| 20 | 1.7 | 1.5× | 60 | 5.1 | 0.45 | 100 | 66 | 50 | 0.051 |
| 20 | 1.7 | 1.5× | 80 | 6.8 | 0.3375 | 75 | 67 | 46 | 0.067 |

6.5 Process Example 4 Effect of Flow Rates and Velocities

In a series of experiments using a T-shaped mixing chamber analogous to that shown in FIG. 3a (an inner diameter of 0.5 mm) and used in Process Example 3, a single nucleic acid stream and a single lipid stream were mixed from opposing directions at various flow rates/linear velocities and subsequently diluted with water at a 1 mm inner diameter dilution tee, as shown generally in FIG. 2. The siRNA SEQ ID NO. 4, cationic lipid A1, PEG lipid B1, cholesterol, and DSPC were used in Process Example 4 in amounts as described above. The total concentration of lipids in the ethanol stream was 16.7 mg/mL. The concentration of siRNA in the nucleic acid stream was 0.9 mg/mL. The results in Table 8 show that increasing linear velocity decreases the particle size and the PDI.

TABLE 8

| Lipid Flow (mL/min) | Lipid linear velocity (m/s) | Total siRNA Flow (mL/min) | siRNA linear velocity (m/s) | dilution Flow (mL/min) | Z-Avg | PDI |
|---|---|---|---|---|---|---|
| 5 | 0.43 | 5 | 0.42 | 5 | 168 | 0.118 |
| 10 | 0.85 | 10 | 0.85 | 10 | 130 | 0.137 |
| 20 | 1.7 | 20 | 1.7 | 20 | 97 | 0.070 |
| 30 | 2.6 | 30 | 2.6 | 30 | 95 | 0.047 |
| 40 | 3.4 | 40 | 3.4 | 40 | 85 | 0.039 |

6.6 Process Example 5 Effect of Orientation of T-Shaped Mixing Chamber

Table 9 shows the results from two experiments using an alternate mixing chamber (0.5 mm inner diameter) analogous to that shown in FIG. 3c. In entry 1 are shown the results obtained where the siRNA enters from the branch and in entry 2 are shown the results obtained where the lipids enter from the branch. For both experiments, the siRNA and lipids were the same as those described above in Process Example 2. The flow rate for the siRNA streams was 120 mL/min and the flow rate of the lipid streams was 40 mL/min. The siRNA concentration was 0.3 mg/mL in a buffer solution containing 66 mM NaCl. The concentration of the lipids was 16.7 mg/mL. The Z-Avg, #-Avg, and PDI were determined 60 minutes post-mixing.

TABLE 9

| entry | Initial mixing chamber | Z-Avg | #-Avg | PDI |
|---|---|---|---|---|
| 1 | T, siRNA into branch | 62 | 48 | 0.070 |
| 2 | T, lipid into branch | 66 | 46 | 0.106 |

6.7 Process Example 6 Effect of Mixing Chamber Configurations

A series of experiments were conducted using mixing chambers having various configurations of nucleic acid and lipid streams with the total number of streams ranging from 3 to 6. In each case the mixing chamber had a 1 mm inner diameter chamber and the flow rates were adjusted to maintain the combined flow of 240 mL/min for the siRNA streams and 80 mL/min for the lipid streams. The concentration of siRNA in these experiments was 0.3 mg/mL and the concentration of lipids was 16.7 mg/mL. The linear velocity of the combined siRNA streams was 5.1 meters/second. The linear velocity of the combined lipid streams was 1.7 meters/second. Where the number of streams allows for more than one arrangement of streams, Table 10 indicates the angle between lipid or siRNA streams. For example, in the case of three lipid streams and three siRNA streams, each lipid stream is separated from the next lipid stream by either 60 degrees (i.e., 3 adjacent lipid streams) or 120 degrees (i.e., lipid streams separated by 120 degrees with intervening siRNA streams also separated by 120 degrees). For the experimental results summarized in Table 10, siRNA SEQ ID NO. 5 was used with cationic lipid A4, DSPC, cholesterol, and PEG lipid B1, in a ratio of 45:9:44:2. The results shown in Table 10 indicate that substantially the same results are obtained for the various mixing configurations where the total flow rates/velocities remained constant.

TABLE 10

| #siRNA streams | #Lipid streams | siRNA flow/strm (ml/min) | Lipid flow/strm (ml/min) | lipid or siRNA angle | 60 min Z-avg. (nm) | 60 min #avg. (nm) | % Encap. @60 min |
|---|---|---|---|---|---|---|---|
| 2 | 1 | 120 | 80 | — | 76 | 66 | 90 |
| 3 | 1 | 80 | 80 | — | 78 | 68 | 89 |
| 2 | 2 | 120 | 40 | 90 | 81 | 70 | 90 |
| 2 | 2 | 120 | 40 | 180 | 81 | 70 | 89 |
| 1 | 3 | 240 | 26.6 | — | 90 | 76 | 91 |
| 4 | 2 | 60 | 40 | 60 | 80 | 70 | 83 |
| 4 | 2 | 60 | 40 | 120 | 80 | 70 | 84 |
| 4 | 2 | 60 | 40 | 180 | 81 | 71 | 84 |
| 3 | 3 | 80 | 26.6 | 60 | 81 | 70 | 86 |
| 3 | 3 | 80 | 26.6 | 120 | 78 | 67 | 86 |
| 2 | 4 | 120 | 20 | 60 | 85 | 74 | 85 |
| 2 | 4 | 120 | 20 | 120 | 83 | 72 | 87 |
| 2 | 4 | 120 | 20 | 180 | 82 | 71 | 85 |

6.8 Process Example 7 Encapsulation of mRNA 6.8.1 Materials and Reagents

TABLE 11

General materials and reagents for Leptin mRNA encapsulation in lipid nanoparticles

| Item | Vendor | Catalog or identification number |
|---|---|---|
| Leptin mRNA | | SEQ ID NO: 6 |
| Cationic lipid | | (9Z,9′Z,12Z,12′Z)-2-(((1,3-dimethylpyrrolidine-3-carbonyl)oxy)methyl)propane-1,3-diyl bis(octadeca-9,12-dienoate) |
| 1,2-distearoyl-sn-glycero-3-phosphocholine (DSPC) | Corden | LP-R4-076 |
| Cholesterol | Sigma | C8667 |
| Lipidated polyethylene glycol (PEG lipid) | Novartis | |
| Ethanol | Sigma | 459844 |
| Nuclease-free water | Life Technologies | 10977 |
| 100 mM citrate buffer, pH 6.0 | Teknova | Q2446 |
| Amicon Ultra-15 centrifugal filter unit, 30 kDa molecular weight cut-off | Millipore | UFC903024 |
| RNaseZap | Life Technologies | AM9780 |
| Syringe pump | KD Scientific | KDS200 |
| 10X phosphate buffered saline | Lonza | 51226 |

TABLE 11-continued

General materials and reagents for Leptin mRNA encapsulation in lipid nanoparticles

| Item | Vendor | Catalog or identification number |
|---|---|---|
| Minimate TFF system, 110 volts | PALL Corporation | OAPMP110 |
| Vivaflow 50, 100 kDa molecular weight cut-off, regenerated cellulose | Sartorius | VF05C4 |
| Quant-IT ribogreen RNA assay kit | Life Technologies | R11490 |
| Tris-EDTA buffer | Promega | V6231 |
| Triton X-100 | Sigma | T8787 |
| Zetasizer NanoZS | Malvern | ZEN3600 |
| Masterflex silicone L/S 14 tubing | Cole-Parmer | 96410-14 |
| 60 ml sterile Plastipak syringe | Becton Dickson | 309653 |
| 140 ml sterile syringe | Tyco | 8881114030 |

TEV-hLeptin-GAopt-2xhBG-120A (SEQ ID NO:6)
Sequence Features:

```
Tobacco Etch Virus (TEV) 5' UTR: 14-154

Optimal Kozak sequence: 155-163

Human leptin encoding amino acids 1-167 of Protein
Accession #

NP_000221, sequence codon optimized by GeneArt:
164-664

2 stop codons: 665-670

2 copies of human beta-globin 3'UTR: 689-954

120 nucleotide polyA tail: 961-1080
```

(SEQ ID NO: 6)
GGGAGACGCGUGUUAAAUAACAAAUCUCAACACAACAUAUACAAAAC

AAACGAAUCUCAAGCAAUCAAGCAUUCUACUUCUAUUGCAGCAAUUU

AAAUCAUUUCUUUUAAAGCAAAAGCAAUUUUCUGAAAAUUUUCACCA

UUUACGAACGAUAGCCGCCACCAUGCACUGGGGAACCCUGUGCGGAU

UCCUGUGGCUGUGGCCCUACCUGUUCUAUGUGCAAGCCGUGCCCAUC

CAGAAGGUGCAGGACGACACCAAGACCCUGAUCAAGACCAUCGUGAC

CCGGAUCAACGACAUCAGCCACACCCAGAGCGUGUCCAGCAAGCAGA

AAGUGACCGGCCUGGACUUCAUCCCCGGCCUGCACCCUAUCCUGACC

CUGUCCAAGAUGGACCAGACCCUGGCCGUGUACCAGCAGAUCCUGAC

CAGCAUGCCCAGCCGGAACGUGAUCCAGAUCAGCAACGACCUGGAAA

ACCUGCGGGACCUGCUGCACGUGCUGGCCUUCAGCAAGAGCUGCCAU

CUGCCUUGGGCCAGCGGCCUGGAAACCCUGGAUUCUCUGGGCGGAGU

GCUGGAAGCCAGCGGCUACUCUACAGAGGUGGUGGCCCUGAGCAGAC

UGCAGGGCAGCCUGCAGGAUAUGCUGUGGCAGCUGGAUCUGAGCCCC

GGCUGCUAAUAGCGGACCGGCGAUAGAUGAAGCUCGCUUUCUUGCUG

UCCAAUUUCUAUUAAAGGUUCCUUUGUUCCCUAAGUCCAACUACUAA

ACUGGGGAUAUUAUGAAGGGCCUUGAGCAUCUGGAUUCUGCCUAAU

AAAAAACAUUUAUUUUCAUUGCAGCUCGCUUUCUUGCUGUCCAAUUU

CUAUUAAAGGUUCCUUUGUUCCCUAAGUCCAACUACUAAACUGGGGG

AUAUUAUGAAGGGCCUUGAGCAUCUGGAUUCUGCCUAAUAAAAAACA

UUUAUUUUCAUUGCGGCCGCAAAAAAAAAAAAAAAAAAAAAAAAAAA

AAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAA.

6.8.2 Preparation of Lipid Mixture in Ethanol

The following is an example of mRNA encapsulated at a cationic lipid amine to mRNA phosphate (N:P) molar ratio of 4:1. Lipids (cationic lipid, DSPC, cholesterol and lipidated PEG) are dissolved in ethanol. The molar ratios of lipids are 40:10:48:2, respectively. For example, in Table 12 are the amounts and final concentrations of all components for a 63 ml volume of lipids in ethanol. The 63 ml volume represents 1.05× of the required volume to ensure the target volume is available for loading into syringe. The mixture is weighed out and placed into a sterile polyethylene terephthalate glycol-modified (PETG) 125 ml bottle and ethanol is added. The mixture is sonicated briefly, then gently agitated for 5 minutes and then maintained at 37° C. until use.

TABLE 12

Lipid mixture components

| Reagent | Amount (mg) | Final concentration (mM) |
|---|---|---|
| Cationic lipid (9Z,9'Z,12Z,12'Z)-2-(((1,3-dimethylpyrrolidine-3-carbonyl)oxy)methyl)propane-1,3-diyl bis(octadeca-9,12-dienoate) | 285.82 | 6.0 |
| DSPC | 74.67 | 1.5 |
| Cholesterol | 175.38 | 7.2 |
| PEG lipid | 51.03 | 0.3 |

6.8.3 Preparation of mRNA in Citrate Buffer

The pH of the citrate buffer is first confirmed to be pH 6.00. If it is not, the pH is adjusted before proceeding. Enough mRNA in water for the encapsulation is thawed from −80° C. storage and exchanged from water into citrate buffer pH 6.0 by use of Amicon Ultra-15 centrifugal concentrators. Between 10 and 12 mg of mRNA can be loaded into each concentrator, which is centrifuged for 5 minutes at 4,000 rpm at 4° C. Volume is increased by the addition of citrate buffer pH 6.0. An exchange of ≥10 volumes with citrate buffer pH 6.0 is recommended to achieve the desired buffer condition. The concentration of the mRNA is measured by optical density at 260 nm in a UV spectrophotometer. The final concentration of the mRNA is adjusted to 0.25 mg/ml in 126 ml of citrate buffer in a sterile 250 ml PETG bottle and is held at room temperature until use. The 126 ml volume represents 1.05× of the required volume to ensure the target volume is available for loading into syringe.

6.8.4 Encapsulation of mRNA in Lipid Nanoparticles

The mRNA encapsulation is carried out using a system as shown generally in FIG. 2. Sterile 60 ml syringes are loaded with an equal volume (60 ml) of lipids in ethanol (syringe (a)), mRNA in citrate buffer (syringes (b1) and (b2)), and citrate buffer alone (syringe (c)). Tubing leading from Luer fittings on the syringe (a) containing lipids is attached to the center input of a cross junction with a 0.5 mm inner diameter. Tubing leading from Luer fittings on syringes (b1) and (b2) containing mRNA at 0.25 mg/ml are attached to the side inputs of the cross junction. The tubing is PTFE tubing with 0.8 mm inner diameter. Syringes (a), (b1) and (b2) are installed on syringe pump A. Tubing leading from the center input of the cross opposite the lipid input is attached to a T junction (see e.g., FIG. 2, T junction 54). Tubing leading from a Luer fitting on syringe (c) containing citrate buffer alone is attached to the T junction to enable in-line dilution of mRNA lipid nanoparticles, and syringe (c) is installed on syringe pump B. Have the output line from the T junction positioned over a sterile 500 ml PETG bottle for collection of the diluted mRNA lipid nanoparticles. It is important to make sure that all fittings are tight on the syringes. In this unoptimized pilot experiment, the syringe pumps were set to the appropriate syringe manufacturer and size (BD, Plastipak, 60 ml) and a flow rate of up to 16 ml per minute. Start both pumps simultaneously, and start collecting material after approximately 0.5 seconds. Approximately 220-230 ml of encapsulated mRNA lipid nanoparticles will be collected.

6.8.5 Dilution of mRNA Lipid Nanoparticles

Use a 140 ml syringe to aspirate 135 ml of the mRNA lipid nanoparticle suspension. Transfer the remaining 85-95 ml to a second 140 ml syringe. Prepare 140 ml syringes with the same volumes of citrate buffer. Another T junction for is set up for another dilution of the mRNA lipid nanoparticle suspension. This dilution step is run with both syringes on only one syringe pump. The 140 ml syringes with 135 ml volumes (one containing lipid nanoparticles, the other containing citrate buffer) are run first, and the 140 ml syringes with the smaller volumes are run second. It is important to make sure that all fittings are tight on the syringes. For the first run change the settings on the syringe pump to the correct size and manufacturer (140 ml, Sherwood-Monoject). The flow rate is set to 25 ml per minute. Collect the diluted mRNA lipid nanoparticle suspension into a sterile 500 ml PETG bottles. The final volume will be approximately 440-460 ml.

6.8.6 Dialysis and Concentration of mRNA Lipid Nanoparticles by Tangential Flow Filtration For every 15 mg of mRNA in the encapsulation run, use a Vivaflow 50 cartridge. For a 30 mg mRNA encapsulation run, use 2 Vivaflow 50 cartridges attached in series. The regenerated cellulose cartridges must first be rendered pyrogen-free. This procedure should be started the day before the encapsulation. Using a Minimate TFF system, set up two Vivaflow 50 cartridges in series and attach tubing. Load 500 ml of pyrogen-free, nuclease-free water into the reservoir and run it through cartridges at 20 psi pressure. Load 100 ml of 0.1 M NaOH/1.0 M NaCl into the reservoir and run 50 ml through the cartridges. Let the remaining 50 ml stand in the cartridges overnight. The next morning run the remaining 50 ml through the cartridges at 20 psi. Load more pyrogen-free, nuclease free water into the reservoir and run 50 ml through the cartridges. Repeat this water wash two more times. Test an aliquot of the last water rinse for endotoxin to make sure it is below detectable amounts.

Load the mRNA lipid nanoparticle suspension into the Minimate TFF reservoir. Concentrate the mixture while maintaining an overall pressure of 20-25 psi. The filtrate should elute at approximately 4 ml per minute to start, but will slow down. Concentrate until the liquid level in the reservoir is at the 40 ml graduation. Diafilter the concentrated mRNA lipid nanoparticle suspension against 300 ml of pyrogen-free, nuclease-free 1×PBS. Keep the pressure of 20-25 psi. After diafiltration, resume concentration of the material to just below the 10 ml graduation mark on the reservoir. Collect the mRNA lipid nanoparticle suspension from the reservoir. It is possible to rinse the TFF system with additional 5 ml of 1×PBS and to collect this wash that contains diluted mRNA lipid nanoparticle suspension, but this wash should be collected separately from the concentrated mRNA lipid nanoparticle suspension. Store materials at 4° C. until analysis.

6.8.7 Percent Encapsulation Determined in a 384-Well Plate Assay Format

To determine the efficiency of the mRNA formulation into lipid nanoparticles, the percent encapsulation of the mRNA is measured using a Quant-IT ribogreen RNA assay kit from Life Technologies. The mRNA lipid nanoparticle suspension is assayed in nuclease-free TE buffer to determine the concentration of mRNA outside of the lipid nanoparticles, and also assayed in TE buffer plus 0.75% Triton X-100 detergent to break apart the lipid nanoparticles and determine the concentration of mRNA in the entire lipid nanoparticle suspension. The relation of the two concentrations is used to calculate the percent encapsulation.

In both TE buffer and TE buffer plus 0.75% Triton X-100 detergent, prepare a 1000 ng/ml solution of RNA from the 100 µg/ml stock standard RNA provided in the kit. Use this stock to generate standard curves in both TE buffer and TE buffer plus 0.75% Triton X-100 detergent according to Table 13.

TABLE 13

Standard curve for the Quant-IT ribogreen assay kit

| Sample | Microliters of TE | Microliters of RNA standard | Final ng/ml concentration |
| --- | --- | --- | --- |
| 1 | 975 | 25 of stock | 1000 |
| 2 | 300 | 300 of sample 1 | 500 |
| 3 | 300 | 300 of sample 2 | 250 |
| 4 | 300 | 300 of sample 3 | 125 |
| 5 | 300 | 300 of sample 4 | 62.5 |
| 6 | 300 | 300 of sample 5 | 31.25 |
| 7 | 300 | 300 of sample 6 | 15.63 |
| 8 | 300 | 0 | 0 |

Carefully prepare mRNA lipid nanoparticle samples in both TE buffer and TE buffer plus 0.75% Triton X-100 detergent using dilutions ranging from 400-2,000 fold. For two-step dilutions, make sure to perform the first step in PBS, rather than TE or TE plus Triton. Make two sets of dilutions for each sample in each buffer condition, and assay each set of dilutions in triplicate for a total of 6 wells per buffer condition per mRNA lipid nanoparticle sample. Make the standard curve and diluted mRNA lipid nanoparticle samples in 96 deep-well plates, ensuring thorough mixing of the samples as they are prepared. Larger volumes of the standard curve can be prepared and stored in a sealed 96 deep-well plate at 4° C. for up to 3 days for later use.

Add 40 µl of standards and samples per well to a black 384-well assay plate (Costar non-treated, #3573). Use a 250 µl automated multi-channel pipet to aspirate 85 µl of standard curve and dispense 40 μl into two wells of the assay plate. Aspirate 125 μl of each diluted mRNA lipid nanoparticle sample and dispense 40 μl into three wells of the assay plate.

Dilute the ribogreen reagent in the kit 240-fold in TE buffer and add 60 μl to each well of the assay plate. Use a 125 μl automated multi-channel pipet to aspirate 125 μl of diluted ribogreen reagent and dispense 60 μl in each well of the standard curve so that you are changing your tips between the TE and TE plus detergent standard curve samples. Change tips between each diluted mRNA lipid nanoparticle sample.

Mix the samples in the wells by pipetting up and down. This can be done, for example, by placing the black 384-well assay plate on a Biomek FX robot and using 30 μl XL tips. After mixing, measure the fluorescence using a fluorescence microplate reader with excitation at 480 nm and emission at 520 nm.

Subtract the fluorescence value of the reagent blank from the fluorescence value for each RNA sample to generate a standard curve of fluorescence versus RNA concentration for TE and TE plus Triton X-100 conditions. Subtract the fluorescence value of the reagent blank from that of each of the samples and then determine the RNA concentration of each of the samples from the appropriate standard curve. Determine the percent encapsulation of the sample by dividing the difference in concentrations between sample in TE plus TritonX-100 and sample in TE buffer alone by the concentration of the sample in TE plus Triton X-100 detergent.

6.8.8 Particle Analytics

The mRNA lipid nanoparticles are analyzed for size and polydispersity using a Zetasizer Nano ZS from Malvern Instruments. For formulated mRNA at an encapsulated mRNA concentration of >1 mg/ml, dilute 5 μl of sample with 115 μl of 1×PBS. Add to a small volume disposable micro-cuvette (Brand, #759200). Insert the cuvette into the Zetasizer Nano ZS. For the machine settings, set material to be polystyrene latex, dispersant to be water, and cell to be ZEN040. Measure the sample at 25° C. with no wait time. Record Z-Ave (set as diameter, in nanometer units) and polydispersity index (PDI).

TABLE 14

Results of Leptin mRNA encapsulation in (9Z,9'Z,12Z,12'Z)-2-(((1,3-dimethylpyrrolidine-3-carbonyl)oxy)methyl)propane-1,3-diyl bis(octadeca-9,12-dienoate)

| Process | Cationic lipid | Z-Ave (nm) | PDI | Encapsulation | [mRNA] (μg/mL) |
|---------|----------------|------------|-----|---------------|----------------|
| 4 mg scale | (9Z,9'Z,12Z,12'Z)-2-(((1,3-dimethylpyrrolidine-3-carbonyl)oxy)methyl)propane-1,3-diyl bis(octadeca-9,12-dienoate) | 111.7 | 0.135 | 92.0% | 213 |

The above description of the examples and embodiments of the invention is merely exemplary in nature and, thus, variations thereof are not to be regarded as a departure from the spirit and scope of the invention.

The invention claimed is:

1. A method of encapsulating a nucleic acid in a lipid nanoparticle host to provide an encapsulated nucleic acid nanoparticle, the method comprising:
   providing two nucleic acid streams, each of the streams comprising a mixture of a nucleic acid in a first aqueous solution, and together having a combined linear velocity of greater than or equal to about 3 to about 14 meters/second;
   providing one lipid stream, the lipid stream comprising a mixture of one or more lipids in an organic solvent, and having a linear velocity of about 1.5 to about 4.5 meters/second;
   joining the lipid stream with the two nucleic acid streams at a first intersection point configured as a cross connector, wherein the two nucleic acid streams enter the cross connector from opposing directions at about 180° relative to each other, and the lipid stream enters the cross connector at about 90° relative to the two nucleic acid streams to provide a first joined stream;
   flowing the first joined stream in a first direction out of the cross connector in substantially the same direction as the lipid stream and about 90° relative to the two nucleic acid streams; and
   mixing the components thereof to provide a first outlet solution comprising the encapsulated nucleic acid nanoparticle;
   wherein the first aqueous solution and the organic solvent are miscible, one of the first aqueous solution or first organic solution contains a buffer, and the concentration of the organic solvent in the first outlet solution is in an amount to minimize aggregation.

2. The method of claim 1, wherein:
   the first aqueous solution is a first buffer solution comprising an aqueous solution of an alkali metal salt; and
   the organic solvent comprises an alcoholic solvent.

3. The method of claim 1, further comprising:
   diluting the first joined stream with a dilution solvent selected from a second buffer solution, which second buffer solution contains at least one alkali metal salt, and water, to provide the first outlet stream;
   the alkali metal salt is selected from one or more of NaCl and sodium citrate, and
   the concentration of the organic solvent in the first outlet solution is less than about 33%.

4. The method of claim 1, wherein:
   the combined linear velocity of the one or more lipid streams is between about 3 to about 4 meters/second; and
   the combined linear velocity of the one or more nucleic acid streams is between about 9 to about 14 meters/second.

5. The method of claim 2, wherein diluting the first joined stream with a diluting solvent comprises:
   providing a diluting stream, the diluting stream comprising an aqueous solvent selected from a second buffer solution and water; and
   joining the first joined stream with the diluting stream to provide the first outlet stream;
   wherein the combined linear velocity of the one or more lipid streams is between about 3 to about 4 meters/second; and the combined linear velocity of the one or more nucleic acid streams is between about 6 to about 8 meters/second.

6. The method of claim 1, further comprising incubating the first outlet solution;
   diluting the incubated first outlet solution with a second dilution solvent selected from a third buffer solution and water, to provide a second outlet solution; and
   concentrating and dialyzing the second outlet solution, to provide a concentrated dialyzed solution.

7. The method of claim 6, wherein the concentrating comprises concentrating by tangential flow filtration.

8. The method of claim 7 further comprising sterile filtering the concentrated dialyzed solution.

9. The method of claim 1, wherein the nucleic acid is a siRNA.

10. The method of claim 1, wherein the nucleic acid is an mRNA.

11. The method of claim 1, wherein the lipid nanoparticle host comprises one or more of the lipids selected from Table 2.

12. The method of claim 1, wherein the encapsulated nucleic acid nanoparticle has an average particle size diameter of about 30 nm to about 80 nm.

13. The method of claim 1, wherein the encapsulated nucleic acid nanoparticle has an average particle size diameter of about 40 nm to about 70 nm and a polydispersity index of less than about 0.1 as determined by dynamic light scattering.

14. The method of claim 1, wherein the ratio by mass of lipids:nucleic acid is about 15-20:1; the concentration of nucleic acid in the one or more nucleic acid streams is about 0.1 to about 1.5 mg/mL and the concentration of lipids in the one or more lipid streams is about 10 to about 25 mg/mL; and the concentration of ethanol in the second outlet solution is about 10-15%.

15. The method of claim 5, wherein joining the first joined stream with the diluting stream comprises intersecting the first joined stream with the diluting stream from about 90° relative to the direction of the first joined stream.

16. The method of claim 1, wherein greater than about 90% of the nucleic acid from the nucleic acid stream is encapsulated in the first outlet solution.

17. The method of claim 1, wherein the concentration of the organic solvent in the first outlet solution in an amount to minimize aggregation is less than about 33%.

* * * * *

SEQUENCE LISTING

```
<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: siRNA antisense strand; APOC3 gene

<400> SEQUENCE: 1
agcactgaga atactgtc                                                      18

<210> SEQ ID NO 2
<211> LENGTH: 18
<212> TYPE: DNA
<213> ORGANISM: Artificial Sequence
<220> FEATURE:
<223> OTHER INFORMATION: siRNA antisense strand; APOC3 gene

<400> SEQUENCE: 2
ttcttgtcca gctttatt                                                      18

<210> SEQ ID NO 3
<211> LENGTH: 18
<212> TYPE: DNA
<213> ORGANISM: Artificial Sequence
<220> FEATURE:
<223> OTHER INFORMATION: siRNA antisense strand; APOC3 gene

<400> SEQUENCE: 3
acaacaagga gtacccgg                                                      18
```

```
<210> SEQ ID NO 4
<211> LENGTH: 21
<212> TYPE: DNA
<213> ORGANISM: Artificial Sequence
<220> FEATURE:
<223> OTHER INFORMATION: siRNA antisense strand; FVII gene

<400> SEQUENCE: 4
uuuaauugaa accaagacau u                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA antisense strand; EPAS1 gene

<400> SEQUENCE: 5
ucaugaaauc guuacguugu u                                              21

<210> SEQ ID NO 6
<211> LENGTH: 1080
<212> TYPE: RNA
<213> ORGANISM: Artificial Sequence
<220> FEATURE:
<223> OTHER INFORMATION: TEV-hLeptin-GAopt-2xhBG-120A
<220> FEATURE:
<221> NAME/KEY: 5'UTR
<222> LOCATION: (14)..(154)
<223> OTHER INFORMATION: Tobacco Etch Virus (TEV) 5' UTR: 14-154
<220> FEATURE:
<221> NAME/KEY: misc_feature
<222> LOCATION: (155)..(163)
<223> OTHER INFORMATION: Optimal Kozak sequence
<220> FEATURE:
<221> NAME/KEY: 3'UTR
<222> LOCATION: (689)..(954)
<223> OTHER INFORMATION: 2 copies of human beta-globin 3'UTR: 689-954
<220> FEATURE:
<221> NAME/KEY: polyA_signal
<222> LOCATION: (961)..(1080)

<400> SEQUENCE: 6
gggagacgcg uguuaaauaa caaaucucaa cacaacauau acaaaacaaa cgaaucucaa      60
gcaaucaagc auucuacuuc uauugcagca auuuaaauca uuucuuuuaa agcaaaagca     120
auuuucugaa aauuuucacc auuuacgaac gauagccgcc accaugcacu ggggaacccu     180
gugcggauuc cuguggcugu ggcccuaccu guucuaugug caagccgugc ccauccagaa     240
ggugcaggac gacaccaaga cccugaucaa gaccaucgug acccggauca acgacaucag     300
ccacacccag agcguguccg gcaagcagaa agugaccggc cuggacuuca uccccggccu     360
gcacccuauc cugacccugu ccaagaugga ccagacccug ccguguaccc agcagaauccu     420 gaccagcaug cccagccgga acgugaucca gaucagcaac gaccuggaaa accugcggga     480
ccugcugcac gugcugggccu ucagcaagag cugccaucug ccuugggcca gcggccugga     540
aacccuggau ucucuggggcg gagugcugga agccagcggc uacucuacag agguggcug     600 ccugagcaga cugcagggca gccugcagga uagcugcgug cagcuggauc ugagcccccgg     660 cugcuaauag cggaccggcg auagaugaag cucgcuuucu ugcugccaa uuucuauuaa     720 agguuccuuu guccccuaag uccaacuacu aaacgggggg auauuaugaa gggccuugag     780
caucuggauu cugccuaaua aaaaacauuu auuuucauug cagcucgcuu ucuugcuguc     840
caauuucuau uaaagguucc uuugucccu aagccaacu acuaaacgg gggauauuau     900 gaagggccuu gagcaucugg auucugccua auaaaaaaca uuuauuuuca uugcggccgc     960
```
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080

<210> SEQ ID NO 7
<211> LENGTH: 18
<212> TYPE: DNA
<213> ORGANISM: Artificial Sequence
<220> FEATURE:
<223> OTHER INFORMATION: siRNA sense strand; APOC3 gene

<400> SEQUENCE: 7
gacagtattc tcagtgct                                                  18

<210> SEQ ID NO 8
<211> LENGTH: 18
<212> TYPE: DNA
<213> ORGANISM: Artificial Sequence
<220> FEATURE:
<223> OTHER INFORMATION: siRNA sense strand; APOC3 gene

<400> SEQUENCE: 8
aataaagctg gacaagaa                                                  18

<210> SEQ ID NO 9
<211> LENGTH: 18
<212> TYPE: DNA
<213> ORGANISM: Artificial Sequence
<220> FEATURE:
<223> OTHER INFORMATION: siRNA sense strand; APOC3 gene

<400> SEQUENCE: 9
ccgggtactc cttgttgt                                                  18

<210> SEQ ID NO 10
<211> LENGTH: 21
<212> TYPE: DNA
<213> ORGANISM: Artificial Sequence
<220> FEATURE:
<223> OTHER INFORMATION: siRNA sense strand; FVII gene

<400> SEQUENCE: 10
ugucuugguu ucaauuaaau u                                              21

<210> SEQ ID NO 11
<211> LENGTH: 21
<212> TYPE: DNA
<213> ORGANISM: Artificial Sequence
<220> FEATURE:
<223> OTHER INFORMATION: siRNA sense strand; EPAS1 gene

<400> SEQUENCE: 11
caacguaacg auuucaugau u                                              21